US012380572B2

(12) United States Patent
Dougherty et al.

(10) Patent No.: US 12,380,572 B2
(45) Date of Patent: Aug. 5, 2025

(54) METHODS FOR THE SEGMENTATION OF LUNGS, LUNG VASCULATURE AND LUNG LOBES FROM CT DATA AND CLINICAL APPLICATIONS

(71) Applicant: Veran Medical Technologies, Inc., St. Louis, MO (US)

(72) Inventors: Andrew Dougherty, Denver, CO (US); Mark Hunter, St. Louis, MO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 677 days.

(21) Appl. No.: 17/543,472

(22) Filed: Dec. 6, 2021

(65) Prior Publication Data

US 2022/0092791 A1 Mar. 24, 2022

Related U.S. Application Data

(63) Continuation-in-part of application No. 16/865,929, filed on May 4, 2020, now Pat. No. 11,699,238, (Continued)

(51) Int. Cl.
*G06T 7/187* (2017.01)
*G06T 7/00* (2017.01)
(Continued)

(52) U.S. Cl.
CPC ............ *G06T 7/187* (2017.01); *G06T 7/0012* (2013.01); *G06T 7/11* (2017.01); *G06T 7/155* (2017.01);
(Continued)

(58) Field of Classification Search
CPC .......... G06T 7/187; G06T 7/64; G06T 7/215; G06T 7/62; G06T 7/11; G06T 7/73;
(Continued)

(56) References Cited

U.S. PATENT DOCUMENTS 6,083,162 A * 7/2000 Vining .................. G06T 19/003
600/407
7,623,900 B2 11/2009 Graham et al.
(Continued)

FOREIGN PATENT DOCUMENTS

WO WO-2019199625 A1 10/2019

OTHER PUBLICATIONS

Deniz Aykac Segmentation and Analysis of the Human Airway Tree From Three-Dimensional X-Ray CT Images, Aug. 2003 (Year: 2003).*
(Continued)

*Primary Examiner* — Stephen S Hong
*Assistant Examiner* — Carl E Barnes, Jr.
(74) *Attorney, Agent, or Firm* — Schwegman Lundberg & Woessner, P.A.

(57) ABSTRACT

Method and processes for segmentation of lungs lobes from CT image data are disclosed. Lobe segmentation relies on other segmentations, including the lungs, the lung airways and vasculature. Segmentation methods and processes begin with the acquisition of 3-D image data such as from a high resolution CT scan of a patient's lungs or at least a region thereof. The image is then processed to provide a segmentation mask from which the components are extracted to identify the lungs and airway. Lung vasculature and lobes are identified by similar processes.

12 Claims, 20 Drawing Sheets

Related U.S. Application Data which is a continuation of application No. 15/952,189, filed on Apr. 12, 2018, now Pat. No. 10,643,333.

(60) Provisional application No. 63/257,766, filed on Oct. 20, 2021.

(51) Int. Cl.
| | |
|---|---|
| *G06T 7/11* | (2017.01) |
| *G06T 7/155* | (2017.01) |
| *G06T 7/215* | (2017.01) |
| *G06T 7/62* | (2017.01) |
| *G06T 7/64* | (2017.01) |
| *G06T 7/73* | (2017.01) |
| *G06T 15/08* | (2011.01) |
| *G06T 17/00* | (2006.01) |

(52) U.S. Cl.
CPC ............... *G06T 7/215* (2017.01); *G06T 7/62* (2017.01); *G06T 7/64* (2017.01); *G06T 7/73* (2017.01); *G06T 15/08* (2013.01); *G06T 17/005* (2013.01); *G06T 2200/04* (2013.01); *G06T 2207/10028* (2013.01); *G06T 2207/10132* (2013.01); *G06T 2207/20104* (2013.01); *G06T 2207/30061* (2013.01); *G06T 2207/30064* (2013.01); *G06T 2207/30096* (2013.01); *G06T 2207/30204* (2013.01); *G06T 2207/30241* (2013.01); *G06T 2210/41* (2013.01)

(58) Field of Classification Search
CPC ....... G06T 7/155; G06T 7/0012; G06T 15/08; G06T 17/005; G06T 2200/04; G06T 2207/10028; G06T 2207/10132; G06T 2207/20104; G06T 2207/30061; G06T 2207/30064; G06T 2207/30096; G06T 2207/30204; G06T 2207/30241; G06T 2210/41; G06T 2210/04

See application file for complete search history.

(56) References Cited

U.S. PATENT DOCUMENTS

| | | | |
|---|---|---|---|
| 8,705,817 | B2 | 4/2014 | Saint Felix et al. |
| 10,573,008 | B2 | 2/2020 | Dougherty et al. |
| 10,643,333 | B2 | 5/2020 | Dougherty et al. |
| 10,869,647 | B2 | 12/2020 | Radhakrishnan |
| 10,878,573 | B2 * | 12/2020 | Markov ............ G06T 7/13 |
| 11,699,238 | B2 | 7/2023 | Hunter et al. |
| 2002/0009215 | A1 * | 1/2002 | Armato, III ............ G06T 7/187 |
| | | | 382/131 |
| 2005/0182295 | A1 | 8/2005 | Soper et al. |
| 2007/0053562 | A1 * | 3/2007 | Reinhardt ............... G06T 5/30 |
| | | | 382/128 |
| 2007/0127800 | A1 * | 6/2007 | Coenen .................. G06T 7/11 |
| | | | 382/128 |
| 2007/0165917 | A1 | 7/2007 | Cao et al. |
| 2008/0192887 | A1 | 8/2008 | Weese et al. |
| 2010/0265251 | A1 | 10/2010 | Vining et al. |
| 2012/0059248 | A1 | 3/2012 | Holsing et al. |
| 2013/0223702 | A1 | 8/2013 | Holsing et al. |
| 2013/0321583 | A1 | 12/2013 | Hager et al. |
| 2014/0210821 | A1 | 7/2014 | Kapoor et al. |
| 2015/0305612 | A1 * | 10/2015 | Hunter ............... A61B 1/00057 |
| | | | 600/109 |
| 2015/0320514 | A1 | 11/2015 | Ahn et al. |
| 2017/0084027 | A1 | 3/2017 | Mintz et al. |
| 2017/0228868 | A1 | 8/2017 | Song et al. |
| 2019/0110839 | A1 | 4/2019 | Rafii-tari et al. |
| 2019/0318483 | A1 | 10/2019 | Dougherty et al. |
| 2019/0318484 | A1 | 10/2019 | Dougherty et al. |
| 2020/0265584 | A1 | 8/2020 | Hunter et al. |

OTHER PUBLICATIONS

Jinzhu Yang Improved Hessian multiscale enhancement filter, 2014, (Year: 2014).*
Shikata, Hidenori , Automated segmentation of pulmonary vascular tree from 3D CT images (Year: 2004).*
Min Li, Color image segmentation using adaptive hierarchical-histogram thresholding (Year: 2020).*
Shivam Sharma, Introduction to DICOM Coordinate Systems (Year: 2022).*
Thorsten Schlathölter Simultaneous Segmentation and Tree Reconstruction of the Airways for Virtual Bronchoscopy (Year: 2002).*
Jul. 9, 2019 PCT Search Report (Serial No. PCT/US19/26244)—Our Matter 5915.
Sep. 10, 2019 USPTO Office Action (U.S. Appl. No. 15/953,150)—Our Matter 5746.
Oct. 1, 2019 USPTO Office Action (U.S. Appl. No. 15/952,189)—Our Matter 5745.
Venetianer, Werblin, Roska, and Chua; Analogic CNN Algorithms for Some Image Compression and Restoration, Tasks; IEEE Transaction on Circuits and Systems—I: Fundamental Theory and Applications, vol. 42, No. 5.
Dec. 6, 2021 USPTO Office Action (U.S. Appl. No. 16/865,929)—Our Matter 6096.
"U.S. Appl. No. 15/952,189, Notice of Allowance mailed Mar. 27, 2020", 9 pgs.
"U.S. Appl. No. 15/952,189, Preliminary Amendment filed Apr. 12, 2018", 6 pgs.
"U.S. Appl. No. 15/952,189, Response filed Mar. 2, 2020 to Non Final Office Action mailed Oct. 1, 2019", 8 pgs.
"U.S. Appl. No. 15/953,150, Notice of Allowance mailed Oct. 17, 2019", 8 pgs.
"U.S. Appl. No. 15/953,150, Response filed Sep. 10, 2019 to Non Final Office Action mailed Sep. 10, 2019", 7 pgs.
"U.S. Appl. No. 16/865,929, Final Office Action mailed Aug. 30, 2022", 15 pgs.
"U.S. Appl. No. 16/865,929, Final Office Action mailed Dec. 7, 2022", 16 pgs.
"U.S. Appl. No. 16/865,929, Non Final Office Action mailed Mar. 15, 2022", 13 pgs.
"U.S. Appl. No. 16/865,929, Notice of Allowance mailed Mar. 13, 2023", 7 pgs.
"U.S. Appl. No. 16/865,929, Response filed Mar. 3, 2023 to Final Office Action mailed Dec. 7, 2022", 9 pgs.
"U.S. Appl. No. 16/865,929, Response filed Mar. 7, 2022 to Non Final Office Action mailed Dec. 6, 2021", 9 pgs.
"U.S. Appl. No. 16/865,929, Response filed May 30, 2022 to Non Final Office Action mailed Mar. 15, 2022", 9 pgs.
"U.S. Appl. No. 16/865,929, Response filed Nov. 30, 2022 to Final Office Action mailed Aug. 30, 2022", 9 pgs.
"European Application Serial No. 19784334.5, Communication Pursuant to Article 94(3) EPC mailed Aug. 7, 2024", 5 pgs.
"European Application Serial No. 19784334.5, Extended European Search Report mailed Feb. 11, 2022", 12 pgs.
"European Application Serial No. 19784334.5, Invitation pursuant to Rule 62a(1) EPC mailed Nov. 22, 2021", 3 pgs.
"European Application Serial No. 19784334.5, Response filed Dec. 1, 2022 to Rule 112(1) EPC mailed Oct. 13, 2022", 13 pgs.
"European Application Serial No. 19784334.5, Response filed Dec. 31, 2020 to Communication pursuant to Rules 161(2) and 162 EPC mailed Nov. 19, 2020", 8 pgs.
"International Application Serial No. PCT/US2019/026244, International Preliminary Report on Patentability mailed Oct. 22, 2020", 8 pgs.
Fabijanska, et al., "Two-pass region growing algorithm for segmenting airway tree from MDCT chest scans", Computerized Medical Imaging and Graphics, Pergamon Press, New York, NY, US, vol. 33, No. 7, (Oct. 1, 2009), 537-546.
Stephen, R. Aylward, et al., "Initialization, Noise, Singularities, and Scale in Height Ridge Traversal for Tubular Object Centerline Extraction", IEEE Transactions on Medical Imaging, IEEE, USA, vol. 21, No. 2, (Feb. 1, 2002), 100-114.

(56) References Cited

OTHER PUBLICATIONS

Tschirren, J., et al., "Intrathoracic Airway Trees: Segmentation and Airway Morphology Analysis from Low-Dose CT Scans", IEEE Transactions on Medical Imaging, IEEE, USA, vol. 24, No. 12, pp. 1529-1539, (Dec. 1, 2005), 31 pgs.
U.S. Appl. No. 15/952,189 U.S. Pat. No. 10,643,333, filed Apr. 12, 2018, Apparatuses and Methods for Navigation in and Local Segmentation Extension of Anatomical Treelike Structures.
U.S. Appl. No. 15/953,150 U.S. Pat. No. 10,573,008, filed Apr. 13, 2018, Apparatuses and Methods for Navigation in and Local Segmentation Extension of Anatomical Treelike Structures.
U.S. Appl. No. 16/865,929 U.S. Pat. No. 11,699,238, filed May 4, 2020, Apparatuses and Methods for Navigation in and Local Segmentation Extension of Anatomical Treelike Structures.

\* cited by examiner

INSPIRATION

DEFORMATION VECTORS CALCULATED FROM INSPIRATION TO EXPIRATION

EXPIRATION

HYBRID INSPIRATION-EXPIRATION

Lung Lobe Segmentation Diagram

METHODS FOR THE SEGMENTATION OF LUNGS, LUNG VASCULATURE AND LUNG LOBES FROM CT DATA AND CLINICAL APPLICATIONS

CROSS-REFERENCE TO RELATED APPLICATIONS

This application is a utility application claiming priority to U.S. provisional application No. 63/257,766, filed on Oct. 20, 2021. This application is also continuation-in-part application claiming priority to U.S. application Ser. No. 16/865,929, filed on May 4, 2020; which is a continuation application claiming priority to application Ser. No. 15/952,189, filed on Apr. 12, 2018 and issued as U.S. Pat. No. 10,643,333 on May 5, 2020; the entire contents of which are incorporated herein by reference.

FIELD

The present disclosure relates generally to medical devices, and particularly to apparatuses and methods associated with a range of image-guided medical procedures for detecting, sampling, staging, and/or treating target tissues, including medical imaging and image processing methods used therefore.

BACKGROUND

Image-guided surgery, also known as image-guided intervention, enhances a physician's ability to locate instruments within anatomy during a medical procedure. Image-guided surgery can include 2-dimensional (2D), 3-dimensional (3D), and 4-dimensional (4D) applications. The fourth dimension of image-guided surgery can include multiple parameters either individually or together such as time, motion, electrical signals, pressure, airflow, blood flow, respiration, heartbeat, and other patient measured parameters.

Practitioners often use 3D medical imaging (e.g., CT, MRI) methods to assess a patient's anatomy and for use during treatment (e.g., during image-guided surgery). In order to access a target area (such as a node, nodule, tumor, or other target), the practitioner must navigate through the patient's anatomy to the target area. As disclosed and described in U.S. Ser. Nos. 13/817,730 and 15/290,822, the entireties of which are incorporated herein by reference, the medical images are segmented (e.g., to locate boundaries and objects within the images) to provide non-invasive information for use during a procedure, including but not limited to navigating to the target area, determining the best anatomical path to reach the target area, and localizing the medical instrument within the anatomy.

In the case of segmenting the lung lobes from CT data, segmentation depends on various other pulmonary segmentations, including the lungs, lung vasculature, and airways. Various algorithms have been proposed for use in lung lobe segmentation. The existing algorithms perform with a varying degree of accuracy and processing time. A common problem encountered by many of these algorithms is the occurrence of incomplete fissures, or lobar boundaries which are either not visible on the CT image or only as diffuse clouds of slightly elevated Hounsfield Unit (HU) voxels in relation to the surrounding parenchyma. In these cases, imaging filters intended to isolate or amplify bright sheet-like structures in the image (like for instance Hessian based response filters) or even the reliance on Hounsfield values, fail to give any useful information, and other approaches must be relied upon.

Once segmentation of the lobes is accomplished there are several ways the segmentation can be useful clinically, some of which will be described.

Although significant improvements have been made in these fields, a need remains for improved medical devices and procedures, including improved segmentation and image processing, for visualizing, accessing, locating, real-time confirming, sampling, and manipulating a target tissue or area.

SUMMARY

One aspect of the disclosure is directed to a local extension method for segmentation of anatomical treelike structures. Methods for segmenting the lungs and lung vasculature are also presented, including a method for segmenting lobes specifically on lower quality expiration datasets.

The methods include receiving an initial segmentation of 3D image data including an initial treelike structure and defining a target point in the 3D image data. A region of interest is extracted based on the target point to create a sub-image. Highly tubular voxels are detected in the sub-image, and a spillage-constrained region growing is performed using the highly tubular voxels as seed points. Connected components are extracted from the region growing step. The extracted components are pruned to discard components not likely to be connected to the initial treelike structure and keep only candidate components likely to be a valid sub-tree of the initial treelike structure. The candidate components are connected to the initial treelike structure to extend the initial segmentation.

Another aspect of the disclosure is directed to a method including receiving 3D image data and segmenting an initial treelike structure in the 3D image data to create an initial segmentation. A skeletonization of the initial segmentation is created and voxels in the initial segmentation are mask-labeled according to the skeletonization. A target point in the initial segmentation is defined, and a region of interest is extracted based on the target point to create a sub-image. The sub-image is smoothed, and the contrast in the sub-image is enhanced. Highly tubular voxels are detected in the sub-image, and a spillage-constrained region growing is performed using the highly tubular voxels as seed points. Connected components are extracted from the region growing results. A skeletonization of the extracted components is created, and voxels in the extracted components are mask-labeled according to the skeletonization. The extracted components are pruned to discard components not likely to be connected to the initial treelike structure and keep only candidate components likely to be a valid sub-tree of the initial treelike structure. The candidate components are connected to the initial treelike structure to extend the initial segmentation.

Another aspect of the disclosure is directed to a local extension method for segmentation of anatomical treelike structures. The method includes receiving an initial segmentation of 3D image data including an initial treelike structure and defining a target point in the 3D image data. A region of interest is extracted based on the target point to create a sub-image. Highly tubular voxels are detected in the sub-image, and a spillage-constrained region growing is performed using the highly tubular voxels as seed points. Connected components are extracted from the region growing step. The extracted components are pruned to discard components not likely to be connected to the initial treelike structure and keep only candidate components likely to be a valid sub-tree of the initial treelike structure. The candidate components are connected to the initial treelike structure to extend the initial segmentation.

Yet another aspect of the disclosure is directed to a local extension method for segmentation of anatomical treelike structures. The method includes receiving an initial segmentation of image data including an initial treelike structure and extracting a region of interest from the initial segmentation to create a sub-image. Highly tubular voxels are detected in the sub-image, and a spillage-constrained region growing is performed using the highly tubular voxels as seed points. Connected components are extracted from the results of the region growing step. The extracted components are pruned to discard components not likely to be connected to the initial treelike structure and keep only candidate components likely to be a valid sub-tree of the initial treelike structure. The candidate components are connected to the initial treelike structure to extend the initial segmentation.

Still another aspect of the disclosure is directed to a method of extending a segmentation of an image using information from a navigation system. The method includes tracking, with the navigation system, at least one of a traveled path and a position of an imaging device relative to an initial segmentation of 3D image data including an initial treelike structure. 2D image data comprising at least one 2D image is captured with the imaging device. A point from the 2D image data corresponding to a potential airway structure is obtained by the navigation system. The initial segmentation of 3D image data is extended by the navigation system using the point obtained from the 2D image data.

Another aspect of the disclosure is directed to a method of extending a segmentation of an image using information from a navigation system. The method includes tracking, with the navigation system, at least one of a traveled path, a position, and a trajectory of a navigated instrument relative to an initial segmentation of 3D image data including an initial treelike structure. The initial segmentation of the 3D image data is extended using the tracked traveled path, position, or trajectory of the navigated instrument. Extending the initial segmentation includes extracting a region of interest from the 3D image data to create a sub-image. Connected components based on spillage-constrained region growing using seed points from the sub-image are extracted. The extracted components are pruned to discard components not likely to be connected to the initial treelike structure and keep only candidate components likely to be a valid sub-tree of the initial treelike structure. The candidate components are connected to the initial treelike structure to extend the segmentation.

In another aspect of the disclosure an approach is used which relies on segmentations of the lung vasculature and the lung airways. Because the airway branches into major subtrees that supply each of the lobes, knowledge of the tree-like topology of the airway derived from the airway segmentation mask and the airway mask itself provide good indications of the general lobe positions. Similarly, the lung vasculature tends to have large branches and a higher density of vessels inside each of the lobes and a decreasing density of vessels near lobar boundaries. The vasculature mask is therefore useful in more finely indicating the positions of lobar boundaries, especially in the case of incomplete fissures.

Other objects and features will be in part apparent and in part pointed out hereinafter.

BRIEF DESCRIPTION OF THE DRAWINGS

Like reference numerals indicate corresponding parts throughout the several views of the drawings.

DETAILED DESCRIPTION

Figure 1:
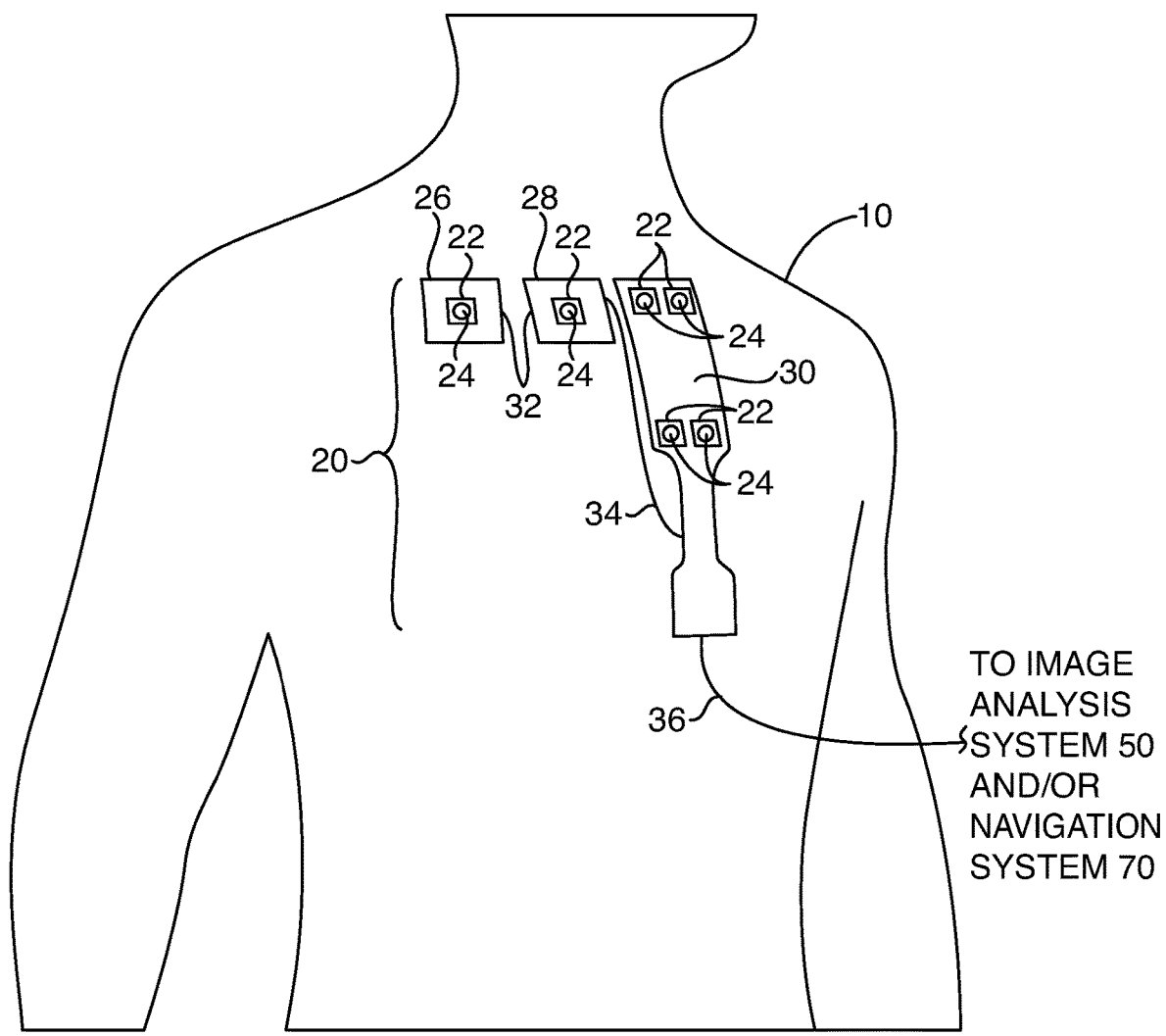
FIG. 1 is a left perspective view of a patient tracking device on a patient according to an embodiment of the invention.

The accompanying Figures and this description depict and describe embodiments of a navigation system (and related methods and devices) in accordance with the present invention, and features and components thereof. It should also be noted that any references herein to front and back, right and left, top and bottom and upper and lower are intended for convenience of description, not to limit the present invention or its components to any one positional or spatial orientation.

Those of skill in the art will appreciate that in the detailed description below, certain well known components and assembly techniques have been omitted so that the present methods, apparatuses, and systems are not obscured in unnecessary detail.

Embodiments of the present disclosure are directed to extending branches of segmented anatomical treelike structures in 3D image data. As used herein, the term 3D image data refers to any type of 3-dimensional imaging modalities, including but not limited to computed tomography, fused computed tomography/positron emission tomography, magnetic resonance imaging, positron emission tomography, single photon emission computed tomography, 3D ultrasound, 3D fluoroscopy, or any other 3D imaging modality.

With larger volumes of patients expected to obtain lung cancer screening, obtaining definitive diagnoses may avoid numerous unneeded lung resections as about only 4% of patients from lung cancer screening are typically found to have a malignancy. However, peripheral target tissues (e.g., nodule, lesion, lymph node, tumor, etc.) that are smaller than 2 cm in size still present a difficult problem to solve. Typical bronchoscopes that are designed mainly for central airway inspection will be limited to the extent they can travel due to their large diameters before becoming wedged in the airway of the patient. Thus, to affect the 5 and 10 year survival rate of patient's that have target tissues which may be less than 2 cm in size, the apparatuses and methods as described herein allow for enhanced target tissue analysis for staging, intercepting target tissues in the periphery of the lungs that may not be accessible via airways, obtaining larger and higher quality tissue samples for testing, and provide a streamlined patient flow. Accordingly, the apparatuses and methods described herein enable a physician or other healthcare professional to initially determine the location of a target tissue and to confirm the location of the target tissue. In one embodiment, a hybrid "Inspiration-Expiration" 3D model may be used to provide patient specific 4D respiratory models which address peripheral respiratory motion. In certain patients, portions of the lungs including the upper lobes may move, on average, 15 mm between inspiration and expiration. Using a steerable catheter with an imaging device, such as a radial endobronchial ultrasound (EBUS) device inserted therein, a physician or other healthcare professional can determine a confirmed location of the target tissue. Additionally, apparatuses and methods described herein enable a physician or other healthcare professional to transition to a percutaneous approach to the target tissue, if needed, or to access the target tissue endobronchially if possible. If the physician or other healthcare professional is unable to reach the target tissue for any reason, including but not limited to, the target tissue being below the surface of the airway (i.e., sub-surface target tissue), no airway proximate the target tissue, the pathway to the target tissue is very tortuous, or larger or additional tissue sample from a core biopsy is desired, the physician or other healthcare professional may insert navigated percutaneous needles to the confirmed location of the target tissue. Thus, it will be understood that the apparatuses and methods described herein may be used to intercept target tissue(s) in the airway, on the wall of the airway, in the wall of the airway, and/or beyond the wall of the airway. That is, the apparatuses and methods described herein may be used to intercept target tissue(s) not only inside the airway, but may intercept target tissue(s) and other anatomical structures inside and/or beyond the wall of the airway. Thus, in certain embodiments, sub-surface target tissue(s) may be intercepted.

As shown in FIG. 1, an apparatus according to an embodiment of the invention includes patient tracking device (PTD) 20 comprising two or more markers 22 and two or more localization elements 24 proximate markers 22. Markers 22 are visible in images captured by an imaging device and the position and orientation (POSE) of localization elements 24 may be tracked by a localization device in an image analysis system and/or a navigation system. PTD 20 comprises a population of separate pads 26, 28, 30, each of which may include one or more markers 22 and localization elements 24 proximate markers 22. First and second pads 26, 28 may each include one marker 22 and one localization element 24. Third pad 30 may include four markers 22 and four localization elements 24 located proximate the periphery of third pad 30. Additionally, wires 32, 34, 36 are used to connect localization elements 24 in each of first, second, and third pads 26, 28, 30 to image analysis system 50 (see FIG. 2) and/or navigation system 70 (see FIG. 3). In alternative embodiments, localization elements 24 may be wirelessly connected to navigation system 70. FIG. 1 illustrates PTD 20 having six markers 22 and six localization elements 24, but any number of two or more markers 22 and localization elements 24 can be used. Patient tracking device (PTD) 20 can be coupled to a dynamic body such as, for example, a selected dynamic portion of the anatomy of a patient 10.

Markers 22 are constructed of a material that can be viewed on an image, such as, for example, X-ray images or CT images. In certain embodiments, markers 22 can be, for example, radiopaque such that they are visible via fluoroscopic imaging. In other embodiments, for example, markers 22 may be echogenic such that they are visible via ultrasonic imaging. In yet other embodiments, markers 22 may be both radiopaque and echogenic. In certain embodiments, for example, localization elements 24 comprise six (6) degree of freedom (6 DOF) electromagnetic coil sensors. In other embodiments, localization elements 24 comprise five (5) degree of freedom (5 DOF) electromagnetic coil sensors. In other embodiments, localization elements 24 comprise other localization devices such as radiopaque markers that are visible via fluoroscopic imaging and echogenic patterns that are visible via ultrasonic imaging. In yet other embodiments, localization elements 24 can be, for example, infrared light emitting diodes, and/or optical passive reflective markers. Localization elements 24 can also be, or be integrated with, one or more fiber optic localization (FDL) devices.

While PTD 20 is shown comprising a population of separate pads containing markers 22 and localization elements 24, in certain embodiments, PTD 20 may comprise one pad containing markers 22 and localization elements 24. In another embodiment, for example, PTD 20 may include markers 22 but not localization elements 24. In another embodiment, for example, PTD 20 may include localization elements 24 but not markers 22. In various embodiments, markers 22 and localization elements 24 can be the same device. In certain embodiments, for example, localization elements 24 may function or serve as markers 22. PTD 20 can be a variety of different shapes and sizes. For example, in one embodiment PTD 20 is substantially planar, such as in the form of a pad that can be disposed at a variety of locations on a patient's 10 body. PTD 20 can be coupled to patient 10 with adhesive, straps, hook and pile, snaps, or any other suitable coupling method. In another embodiment the PTD can be a catheter type device with a pigtail or anchoring mechanism that allows it to be attached to an internal organ or along a vessel.

As described more fully elsewhere herein, an image analysis system is configured to receive image data associated with the dynamic body generated during a pre-surgical or pre-procedural first time interval. The image data can include an indication of a position of each of markers 22 for multiple instants in time during the first time interval. Then a navigation system can also receive position data associated with localization elements 24 during a second time interval in which a surgical procedure or other medical procedure is being performed. The navigation system can use the position data received from localization elements 24 to determine a distance between the localization elements 24 for a given instant in time during the second time interval. The navigation system can also use the image data to determine the distance between markers 22 for a given instant in time during the first time interval. The navigation system can then find a match between an image where the distance between markers 22 at a given instant in time during the first time interval is the same or substantially the same as the distance between localization elements 24 associated with those markers 22 at a given instant in time during the medical procedure, or second time interval. Additionally, the navigation system can determine a sequence of motion of the markers and match this sequence of motion to the recorded motion of the markers over the complete procedure or significant period of time. Distance alone between the markers may not be sufficient to match the patient space to image space in many instances, the system may also determine the direction the markers are moving and the range and speed of this motion to find the appropriate sequence of motion for a complex signal or sequence of motion by the patient.

A physician or other healthcare professional can use the images selected by the navigation system during a medical procedure performed during the second time interval. For example, when a medical procedure is performed on a targeted anatomy of a patient, such as a heart or lung, the physician may not be able to utilize an imaging device during the medical procedure to guide him to the targeted area within the patient. Accordingly, PTD 20 can be positioned or coupled to the patient proximate the targeted anatomy prior to the medical procedure, and pre-procedural images can be taken of the targeted area during a first time interval. Markers 22 of PTD 20 can be viewed with the image data, which can include an indication of the position of markers 22 during a given path of motion of the targeted anatomy (e.g., the heart) during the first time interval. Such motion can be due, for example, to inspiration (i.e., inhaling) and expiration (i.e., exhaling) of the patient, or due to the heart beating. During a medical procedure, performed during a second time interval, such as a procedure on a heart or lung, the navigation system receives data from localization elements 24 associated with a position of localization elements 24 at a given instant in time during the medical procedure (or second time interval). The distance between selected pairs of markers 22 can be determined from the image data and the distance, range, acceleration, and speed between corresponding selected pairs of localization elements 24 can be determined based on the position and orientation (POSE) data for given instants in time. Accordingly, the range of motion and speed of markers 22 can be calculated.

Because localization elements 24 are proximate the location of markers 22, the distance between a selected pair of localization elements 24 can be used to determine an intra-procedural distance between the pair of corresponding markers 22. An image from the pre-procedural image data taken during the first time interval can then be selected where the distance between the pair of selected markers 22 in that image corresponds with or closely approximates the same distance determined using localization elements 24 at a given instant in time during the second time interval. This process can be done continuously during the medical procedure, producing simulated real-time, intra-procedural images illustrating the orientation and shape of the targeted anatomy as a catheter, sheath, needle, forceps, guidewire, fiducial delivery devices, therapy device, or similar medical device(s) is/are navigated to the targeted anatomy. Thus, during the medical procedure, the physician can view selected image(s) of the targeted anatomy that correspond to and simulate real-time movement of the anatomy. In addition, during a medical procedure being performed during the second time interval, such as navigating a catheter or other medical device or component thereof to a targeted anatomy, the location(s) of a localization element (e.g., an electromagnetic coil sensor) coupled to the catheter during the second time interval can be superimposed on an image of a catheter. The superimposed image(s) of the catheter can then be superimposed on the selected image(s) from the first time interval, providing simulated real-time images of the catheter location relative to the targeted anatomy. This process and other related methods are described in U.S. Pat. No. 7,398,116, entitled Methods, Apparatuses, and Systems Useful in Conducting Image Guided Interventions, filed Aug. 26, 2003, the entire contents of which is hereby incorporated by reference.

Figure 2:
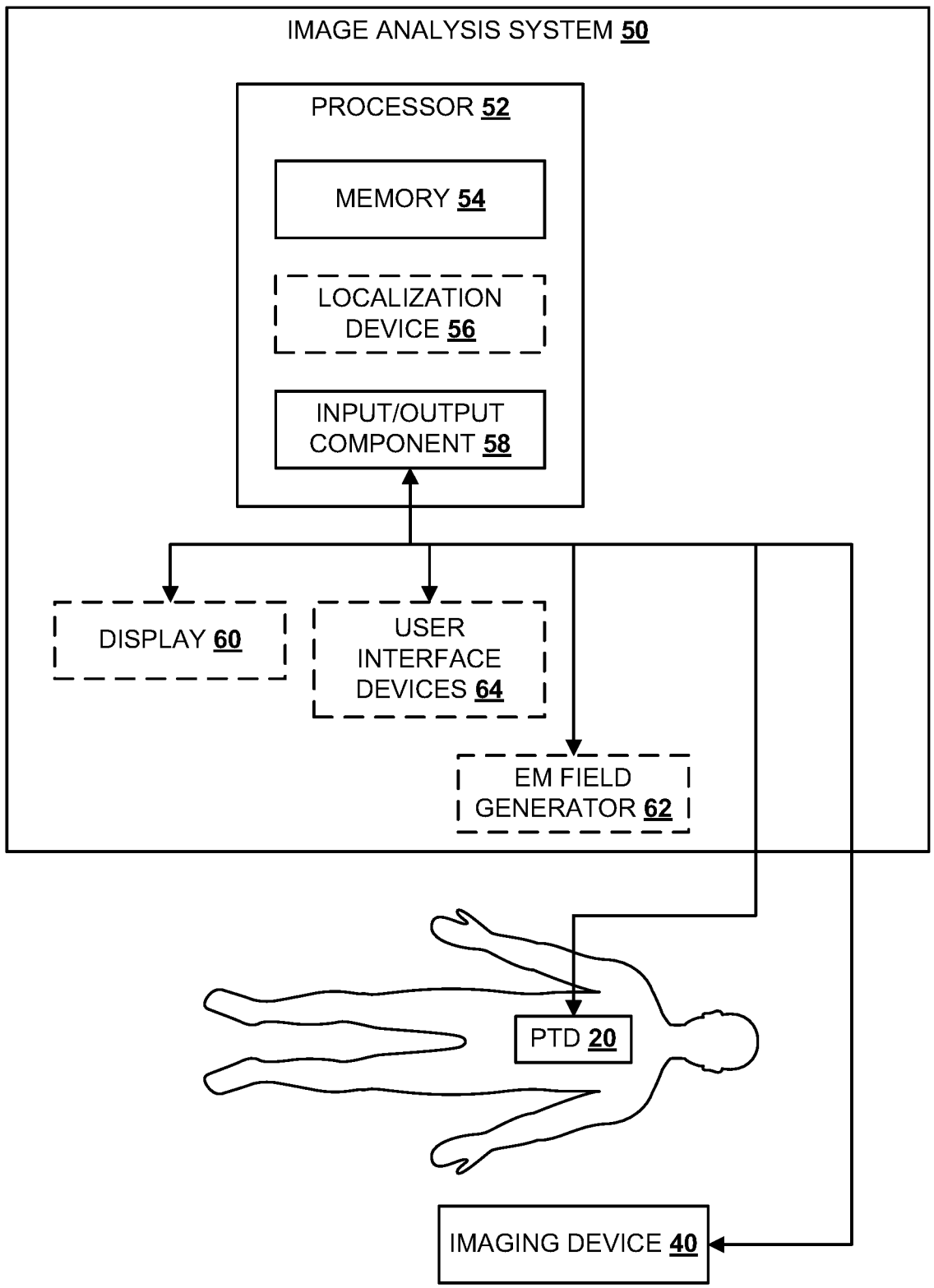
FIG. 2 is a schematic illustration of an image analysis system according to an embodiment of the invention.
Figure 3:
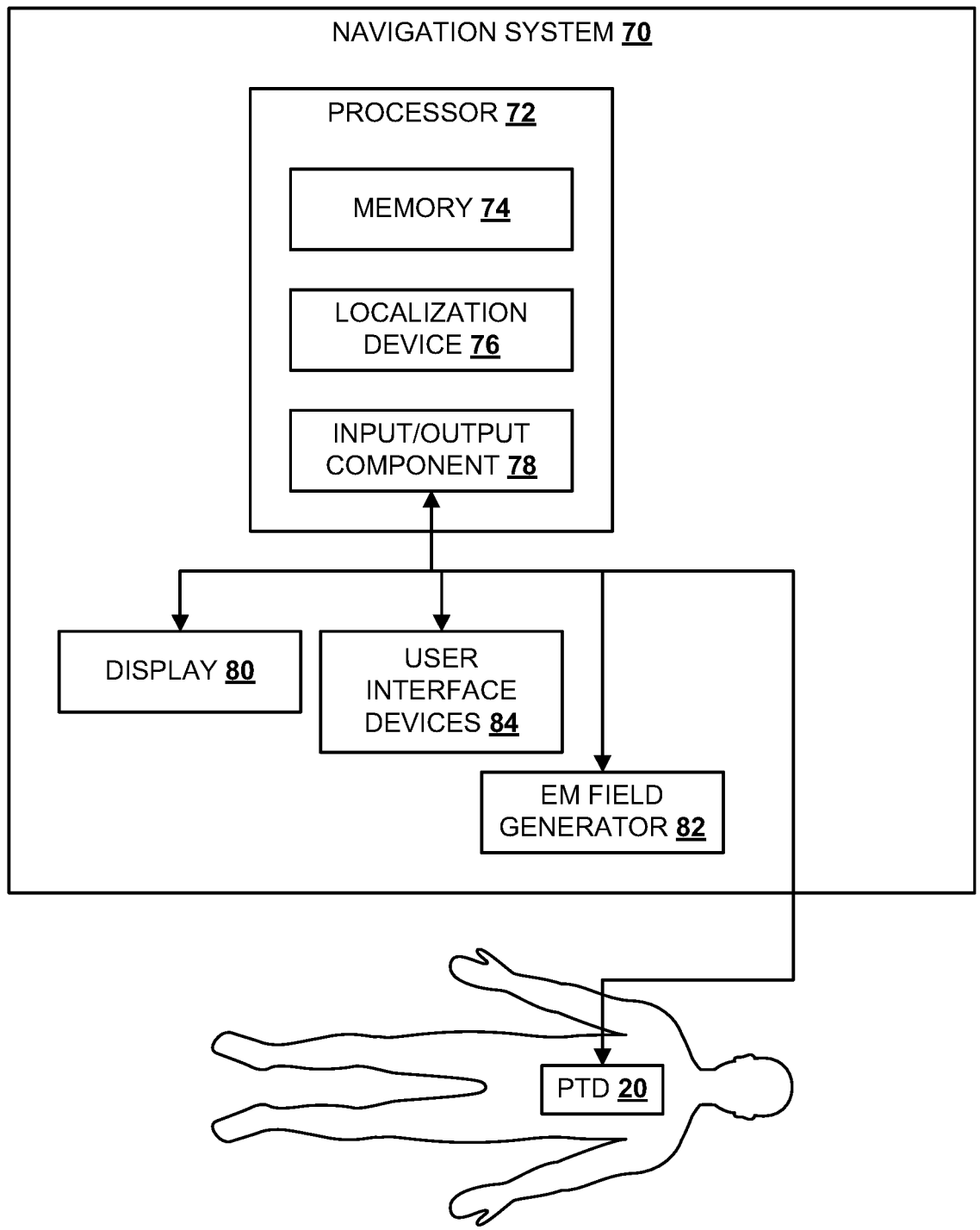
FIG. 3 is a schematic illustration of a navigation system according to an embodiment of the invention.

Referring now to FIGS. 2 and 3, two systems which may be used during image guided surgery are described in detail. The first system illustrated in FIG. 2, is image analysis system 50. Image analysis system 50 is used during generation of a population of images of patient 10 during a first time interval, prior to a medical procedure being performed on patient 10. The second system, illustrated in FIG. 3, is navigation system 70. Navigation system 70 is used during a medical procedure performed on patient 10 during a second time interval. As will be described, imaging system 50 and navigation system 70 may include, in various embodiments, substantially similar or identical components. Accordingly, image analysis system 50 and navigation system 70 may be able to carry out substantially similar or identical functions. In certain embodiments, image analysis system 50 and navigation system 70 and may comprise a single system. In certain embodiments, for example, image analysis system 50 may also function or serve as a navigation system. In certain embodiments, for example, navigation system 70 may also function or serve as an image analysis system.

As shown in FIG. 2, image analysis system 50 comprises a processor 52 having memory component 54, input/output (I/O) component 58, and optional localization device 56. Image analysis system 50 may also optionally include display 60, electromagnetic field generator 62, and/or user interface device(s) 64 (e.g., keyboard, mouse).

Image analysis system 50 further includes and/or is in data communication with imaging device 40. Imaging device 40 can be, for example, a computed tomography (CT) device (e.g., respiratory-gated CT device, ECG-gated CT device), a magnetic resonance imaging (MRI) device (e.g., respiratory-gated MRI device, ECG-gated MRI device), an X-ray device, a 2D or 3D fluoroscopic imaging device, and 2D, 3D or 4D ultrasound imaging devices, or any other suitable medical imaging device. In one embodiment, for example, imaging device 40 is a computed tomography—positron emission tomography (CT/PET) device that produces a fused computed tomography—positron emission tomography (CT/PET) image dataset. In the case of a two-dimensional imaging device, a population of two-dimensional images may be acquired and then assembled into volumetric data (e.g., three-dimensional (3D) image dataset) as is known in the art using a two-dimensional to three-dimensional conversion. Pre-procedurally during a first time interval, imaging device 40 can be used to generate a population of images of patient 10 while PTD 20 is coupled to patient 10; wherein the population of images depict the anatomy of patient 10. The anatomy, may include, but is not limited to, the lungs, heart, liver, kidneys, and/or other organs of patient 10. The population of images can be compiled into an image dataset. As stated above, some or all markers 22 of PTD 20 are visible on the population of images and provide an indication of a position of some or all of markers 22 during the first time interval. The position of markers 22 at given instants in time through a path of motion of patient 10 can be illustrated with the images.

Processor 52 of image analysis system 50 includes a processor-readable medium storing code representing instructions to cause the processor 52 to perform a process. Processor 52 can be, for example, a commercially available personal computer, or a less complex computing or processing device that is dedicated to performing one or more specific tasks. For example, processor 52 can be a terminal dedicated to providing an interactive graphical user interface (GUI) on optional display 60. Processor 52, according to one or more embodiments of the invention, can be a commercially available microprocessor. Alternatively, processor 52 can be an application-specific integrated circuit (ASIC) or a combination of ASICs, which are designed to achieve one or more specific functions, or enable one or more specific devices or applications. In yet another embodiment, processor 52 can be an analog or digital circuit, or a combination of multiple circuits.

Additionally, processor 52 can include memory component 54. Memory component 54 can include one or more types of memory. For example, memory component 54 can include a read only memory (ROM) component and a random access memory (RAM) component. Memory component 54 can also include other types of memory that are suitable for storing data in a form retrievable by processor 52. For example, electronically programmable read only memory (EPROM), erasable electronically programmable read only memory (EEPROM), flash memory, as well as other suitable forms of memory can be included within the memory component. Processor 52 can also include a variety of other components, such as for example, coprocessors, graphic processors, etc., depending upon the desired functionality of the code.

Processor 52 can store data in memory component 54 or retrieve data previously stored in memory component 54. The components of processor 52 can communicate with devices external to processor 52 by way of input/output (I/O) component 58. According to one or more embodiments of the invention, I/O component 58 includes a variety of suitable communication interfaces. For example, I/O component 58 can include, for example, wired connections, such as standard serial ports, parallel ports, universal serial bus (USB) ports, S-video ports, local area network (LAN) ports, small computer system interface (SCSI) ports, and so forth. Additionally, I/O component 58 can include, for example, wireless connections, such as infrared ports, optical ports, Bluetooth® wireless ports, wireless LAN ports, or the like. Embodiments of image analysis system 50 which include display 60, electromagnetic field generator 62, and/or user interface device(s) 64, such components communicate with processor 52 via I/O component 58.

Processor 52 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

As stated above, processor 52 receives the population of images from imaging device 40. Processor 52 identifies the position of selected markers 22 within the image data or voxel space using various segmentation techniques, such as Hounsfield unit thresholding, convolution, connected component, or other combinatory image processing and segmentation techniques. Segmentation methods for identifying anatomical structure and for use during navigation are described in detail herein below. Processor 52 determines a distance and direction between the position of any two markers 22 during multiple instants in time during the first time interval, and stores the image data, as well as the position and distance data, within memory component 54. Multiple images can be produced providing a visual image at multiple instants in time through the path of motion of the dynamic body.

As stated above, processor 52 can optionally include a receiving device or localization device 56 for tracking the location of localization elements 24 of PTD 20, as described more fully elsewhere herein. By tracking localization elements 24 associated with PTD 20 when the population of images are generated by imaging device 40, the population of images may be gated. That is, image analysis system 50 determines the respiratory phase at which the population of images were generated, and this information may be stored in an image dataset and/or in another data store in memory component 54.

In general, image analysis system 50 may comprise any tracking system typically employed in image guided surgery, including but not limited to, an electromagnetic tracking system. An example of a suitable electromagnetic tracking subsystem is the AURORA electromagnetic tracking system, commercially available from Northern Digital Inc. (Waterloo, Ontario Canada). In one embodiment, image analysis system 50 may include an electromagnetic tracking system, typically comprising an electromagnetic (EM) field generator 62 that emits a series of electromagnetic fields designed to engulf patient 10, and localization elements 24 coupled to PTD 20. In certain embodiments, for example, localization elements 24 are electromagnetic coils that receive an induced voltage from electromagnetic (EM) field generator 62, wherein the induced voltage is monitored and translated by localization device 56 into a coordinate position of localization elements 24. In certain embodiments, localization elements 24 are electrically coupled to twisted pair conductors to provide electromagnetic shielding of the conductors. This shielding prevents voltage induction along the conductors when exposed to the magnetic flux produced by the electromagnetic field generator.

Accordingly, localization device 56 can be, for example, an analog to digital converter that measures voltages induced onto localization elements 24 in the field generated by EM field generator 62; creates a digital voltage reading; and maps that voltage reading to a metric positional measurement based on a characterized volume of voltages to millimeters from electromagnetic field generator 62. Position data associated with localization elements 24 can be transmitted or sent to localization device 56 continuously during imaging of patient 10 during the first time interval. Thus, the position of localization elements 24 can be captured at given instants in time during the first time interval. Because localization elements 24 are proximate markers 22, localization device 56 uses the position data of localization elements 24 to deduce coordinates or positions associated with markers 22 during the first time interval. The distance, range, acceleration, and speed between one or more selected pairs of localization elements 24 (and corresponding markers 22) is then determined and various algorithms are used to analyze and compare the distance between selected elements 24 at given instants in time, to the distances between and orientation among corresponding markers 22 observed in a population of pre-procedural images.

As shown in FIG. 3, navigation system 70 comprises a processor 72 having memory component 74, input/output (I/O) component 78, and localization device 76. Navigation system 70 also includes display 80, electromagnetic field generator 82, and/or user interface device(s) 84 (e.g., keyboard, mouse). In certain embodiments, navigation system 50 further includes and/or is in data communication with imaging device 40 (see FIG. 2).

Processor 72 of navigation system 70 includes a processor-readable medium storing code representing instructions to cause the processor 72 to perform a process. Processor 72 can be, for example, a commercially available personal computer, or a less complex computing or processing device that is dedicated to performing one or more specific tasks. For example, processor 72 can be a terminal dedicated to providing an interactive graphical user interface (GUI) on optional display 80. Processor 72, according to one or more embodiments of the invention, can be a commercially available microprocessor. Alternatively, processor 72 can be an application-specific integrated circuit (ASIC) or a combination of ASICs, which are designed to achieve one or more specific functions, or enable one or more specific devices or applications. In yet another embodiment, processor 72 can be an analog or digital circuit, or a combination of multiple circuits.

Additionally, processor 72 can include memory component 74. Memory component 74 can include one or more types of memory. For example, memory component 74 can include a read only memory (ROM) component and a random access memory (RAM) component. Memory component 74 can also include other types of memory that are suitable for storing data in a form retrievable by processor 72. For example, electronically programmable read only memory (EPROM), erasable electronically programmable read only memory (EEPROM), flash memory, as well as other suitable forms of memory can be included within the memory component. Processor 72 can also include a variety of other components, such as for example, coprocessors, graphic processors, etc., depending upon the desired functionality of the code.

Processor 72 can store data in memory component 74 or retrieve data previously stored in memory component 74. The components of processor 72 can communicate with devices external to processor 72 by way of input/output (I/O) component 78. According to one or more embodiments of the invention, I/O component 78 includes a variety of suitable communication interfaces. For example, I/O component 78 can include, for example, wired connections, such as standard serial ports, parallel ports, universal serial bus (USB) ports, S-video ports, local area network (LAN) ports, small computer system interface (SCSI) ports, and so forth. Additionally, I/O component 78 can include, for example, wireless connections, such as infrared ports, optical ports, Bluetooth® wireless ports, wireless LAN ports, or the like. Additionally, display 80, electromagnetic field generator 82, and/or user interface device(s) 84, communicate with processor 72 via I/O component 78.

Processor 72 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

In general, navigation system 70 may comprise any tracking system typically employed in image guided surgery, including but not limited to, an electromagnetic tracking system. An example of a suitable electromagnetic tracking subsystem is the AURORA electromagnetic tracking system, commercially available from Northern Digital Inc. (Waterloo, Ontario Canada). In one embodiment, navigation system 70 may include an electromagnetic tracking system, typically comprising an electromagnetic (EM) field generator 82 that emits a series of electromagnetic fields designed to engulf patient 10, and localization elements 24 coupled to PTD 20. In certain embodiments, for example, localization elements 24 are electromagnetic coils that receive an induced voltage from electromagnetic (EM) field generator 82, wherein the induced voltage is monitored and translated by localization device 76 into a coordinate position of localization elements 24. In certain embodiments, localization elements 24 are electrically coupled to twisted pair conductors to provide electromagnetic shielding of the conductors. This shielding prevents voltage induction along the conductors when exposed to the magnetic flux produced by the electromagnetic field generator.

Accordingly, localization device 76 may be, for example, an analog to digital converter that measures voltages induced onto localization elements 24 in the field generated by EM field generator 82; creates a digital voltage reading; and maps that voltage reading to a metric positional measurement based on a characterized volume of voltages to millimeters from electromagnetic field generator 82. Position data associated with localization elements 24 may be transmitted or sent to localization device 76 continuously during the medical procedure performed during the second time interval. Thus, the position of localization elements 24 may be captured at given instants in time during the second time interval. Because localization elements 24 are proximate markers 22, localization device 76 uses the position data of localization elements 24 to deduce coordinates or positions associated with markers 22 during the second time interval. The distance, range, acceleration, and speed between one or more selected pairs of localization elements 24 (and corresponding markers 22) is then determined and various algorithms are used to analyze and compare the distance between selected elements 24 at given instants in time, to the distances between and orientation among corresponding markers 22 observed in a population of pre-procedural images.

Because localization elements 24 of PTD 20 may be tracked continuously during the first and/or second time intervals, a sequence of motion of PTD 20 that represents the motion of an organ of patient 10 or the patient's 10 respiratory cycle may be collected. As patient 10 inhales and exhales, the individual localization elements 24 of PTD 20 will move relative to one another. That is, as patient 10 inhales, the distance between some or all of localization elements 24 of PTD 20 may increase. Conversely, as patient 10 exhales, the distance between some or all of localization elements 24 of PTD 20 may decrease. The sequence of motion of localization elements 24 is tracked by image analysis system 50 and/or navigation system 70 and image analysis system 50 and/or navigation system 70 derives a respiratory signal based on the positions of localization elements 24 during the respiratory cycle of patient 10. The sequence of motion may then be analyzed to find unique similar points within the image dataset and images within the image dataset may be grouped.

According to one particular embodiment, the respiratory signal derived from PTD 20 is used to gate the localization information of a medical device in the airway of patient 10. In other embodiments, the respiratory signal derived from PTD 20 is used during the first time interval to gate the population of images generated by imaging device 40. Using PTD 20 to derive a respiratory signal may assist in determining multiple airway models, for example, by performing a best fit of the real-time patient airway model to the image dataset to derive the optimal registration and gated period in the patient's respiratory cycle. Additionally or alternatively, the respiratory signal may be derived from devices other than PTD 20 that are known in the art for measuring the respiratory cycle of a patient. In certain embodiments, for example, a device that records the resistance between two locations on the patient may be used to measure the respiratory cycle. For example, such a device is similar to a variable potentiometer in that the resistance of the patient changes between two fixed points as the patient inhales and exhales. Thus, the resistance may be measured to create a respiratory signal. In other embodiments, a spirometer may be used to measure the respiratory cycle. In yet other embodiments, a cardiac signal may be used to gate the localization information of a medical device in the airway of patient 10. It will be understood that any type of device for generating a cardiac signal may be used, including, but not limited to an ECG device, PTD 20, etc.

Figure 4:
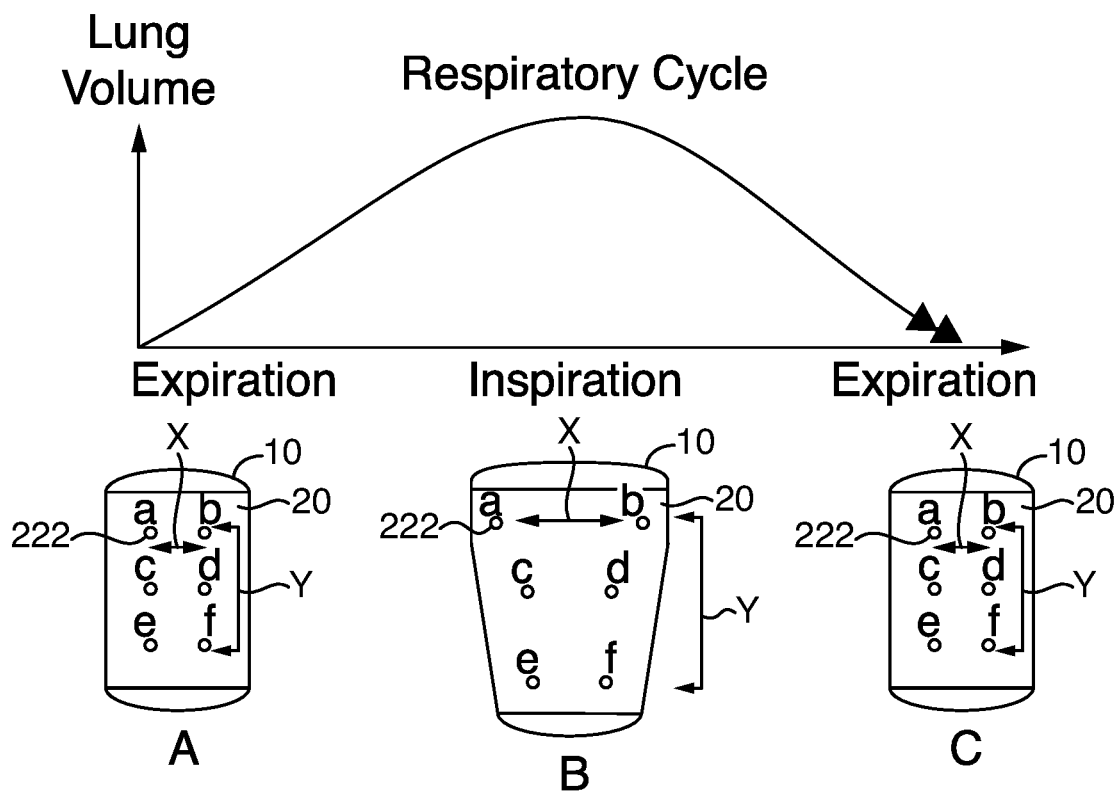
FIG. 4 is a graphical representation illustrating the function of the patient tracking device according to an embodiment of the invention.

FIG. 4 is a schematic illustration indicating how markers 22 of PTD 20 can move and change orientation and shape during movement of patient 10. The graph is one example of how the lung volume can change during inhalation (inspiration) and exhalation (expiration) of patient 10. The corresponding changes in shape and orientation of PTD 20 during inhalation and exhalation are also illustrated. The six markers 22 shown in FIG. 1 are schematically represented and labeled a, b, c, d, e, and f. As described above, a population of images of PTD 20 may be taken during a first time interval. The population of images include an indication of relative position of one or more markers 22; that is, one or more markers 22 are visible in the images, and the position of each marker 22 is then observed over a period of time. A distance between any two markers 22 may then be determined for any given instant of time during the first time interval. For example, a distance X between markers a and b is illustrated, and a distance Y between markers b and f is illustrated. These distances may be determined for any given instant in time during the first time interval from an associated image that illustrates the position and orientation of markers 22. As illustrated, during expiration of patient 10 at times indicated as A and C, the distance X is smaller than during inspiration of patient 10, at the time indicated as B. Likewise, the distance Y is greater during inspiration than during expiration. The distance between any pair of markers 22 may be determined and used in the processes described herein. Thus, the above embodiments are merely examples of possible pair selections. For example, a distance between a position of marker e and a position of marker b may be determined. In addition, multiple pairs or only one pair may be selected for a given procedure.

Figure 5A:
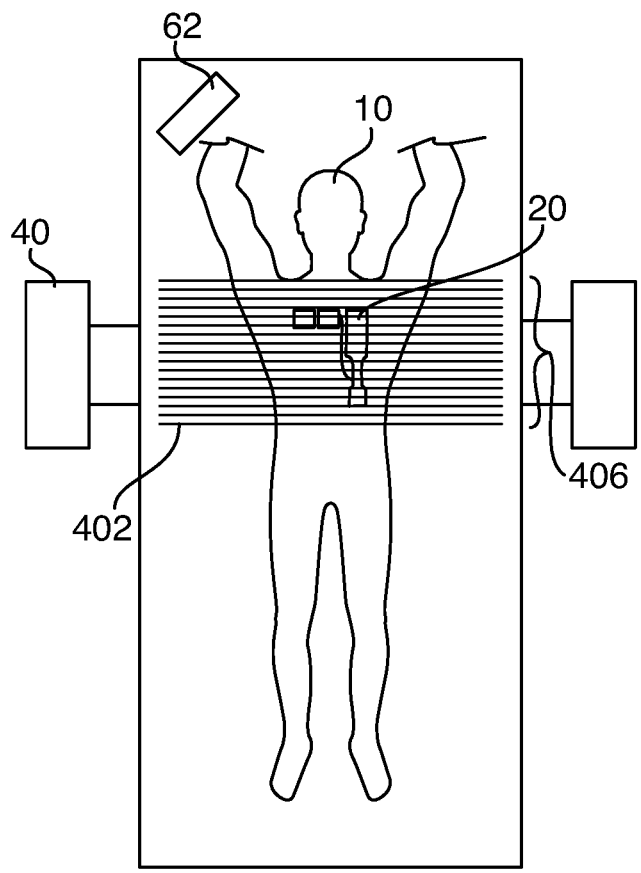
FIG. 5A is an illustration of a patient being imaged using an imaging device according to an embodiment of the invention.
Figure 5B:
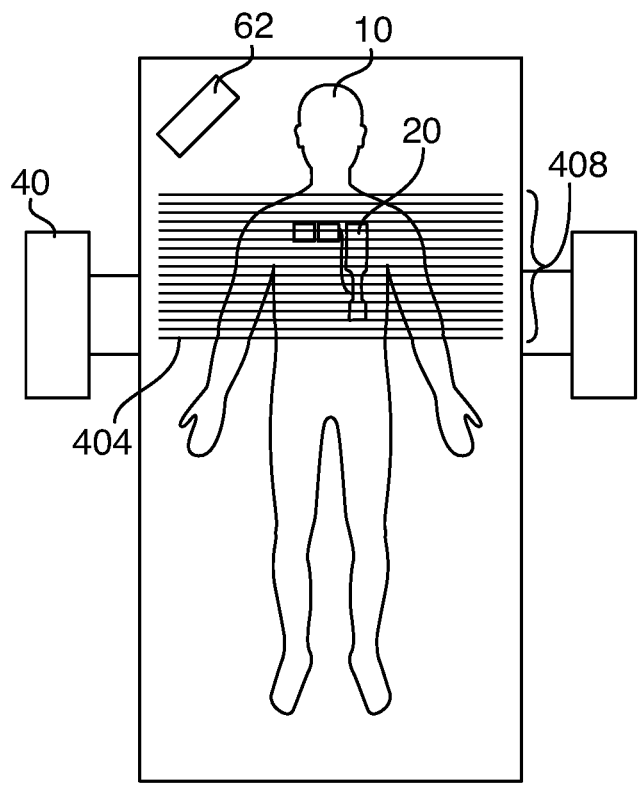
FIG. 5B is an illustration of a patient being imaged using an imaging device according to an embodiment of the invention.

FIGS. 5A and 5B illustrate the generation of a population of images during a first time interval using imaging device 40, PTD 20, and optionally electromagnetic field generator 62 of image analysis system 50. In FIG. 5A, patient 10 inhales and patient 10 is scanned using imaging device 40 which generates a population of images 402 of the anatomy of patient 10 and markers 22 at inspiration. As shown, patient 10 may place their arms above their head as they inhale, and this may be considered a total lung capacity (TLC) scan. In FIG. 5B, patient 10 exhales and patient 10 is scanned using imaging device 40 which generates a population of images 404 of the anatomy of patient 10 and markers 22 at expiration. As shown, patient 10 may place their arms below their head, and this may be considered a functional residual capacity (FRC) scan. The Functional Residual Capacity is the lung volume at the end of a normal expiration, when the muscles of respiration are completely relaxed. At FRC (and typically at FRC only), the tendency of the lungs to collapse is exactly balanced by the tendency of the chest wall to expand. In various embodiments, the population of images 402, 404 may be two-dimensional (2D) images. In other embodiments, for example, the population of images 402, 404 may be three-dimensional (3D) images. Additionally, the population of images 402, 404 may be respiratory gated by tracking the location of localization elements 24 of PTD 20 by image analysis system 50 and/or navigation system 70 using EM field generator 62, 82 during image generation. In other embodiments, for example, the population of images 402, 404 may be gated using any type of device known for generating a physiological signal for gating.

In various embodiments, for example, instead of patient 10 holding an inspiration or expiration state, a cine loop of images may be generated in conjunction with the patient's respiratory cycle information from PTD 20. Thus, the cine loop comprises a population of images generated from inspiration to expiration where the population of images are gated to the respiratory cycle of patient 10 using PTD 20. This can serve to limit registration point selection, in order to be consistent with the patient's respiratory cycle that a 3D dataset such as CT, MR, or PET has acquired. This technique advantageously maximizes registration accuracy, a major flaw in conventional systems in the prior art.

Figure 5C:
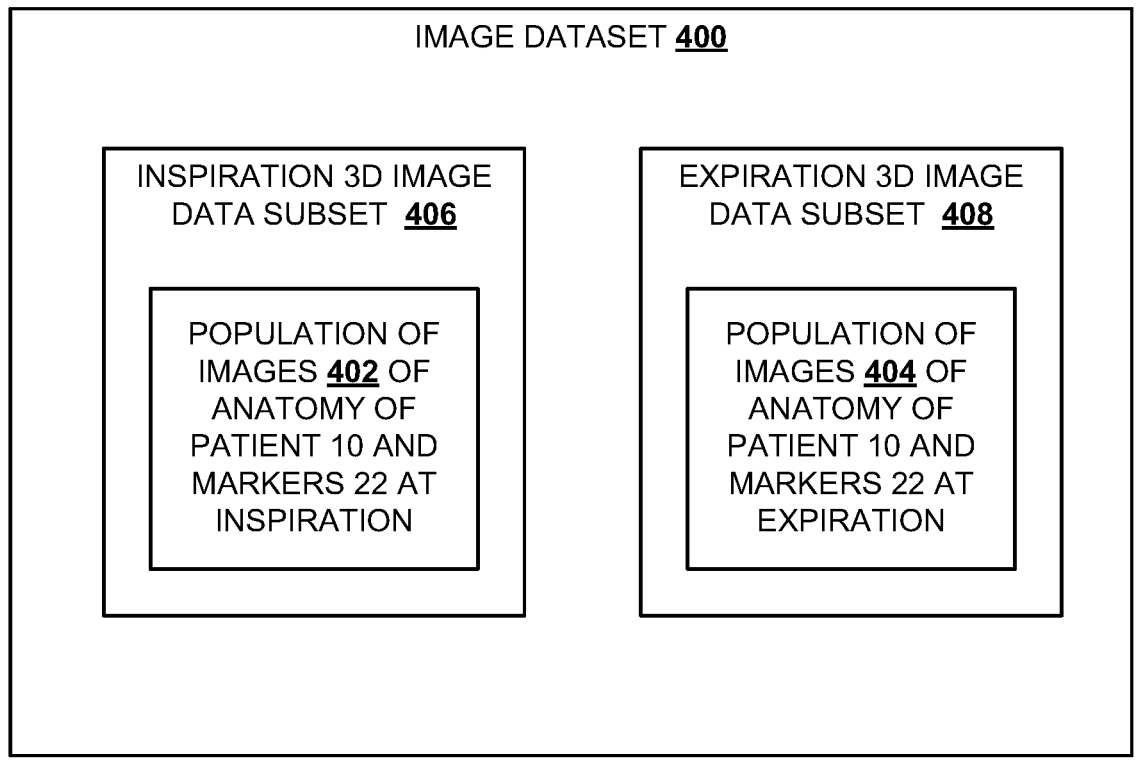
FIG. 5C is a schematic illustration of an image dataset according to an embodiment of the invention.

As described above, imaging device 40 is in data communication with image analysis system 50 and/or navigation system 70 and sends, transfers, copies and/or provides the population of images 402, 404 taken during the first time interval associated with patient 10 to image analysis system 50 and/or navigation system 70. As shown in FIG. 5C, image analysis system 50 and/or navigation system 70 compiles the population of images 402 at inspiration into a 3D image data subset 406 of the anatomy of patient 10 and markers 22 at inspiration (referred to herein as inspiration 3D image data subset 406). Additionally, image analysis system 50 and/or navigation system 70 compiles the population of images 404 at expiration into a 3D image data subset 408 of the anatomy of patient 10 at expiration (referred to herein as expiration 3D image data subset 408). The inspiration 3D image data subset 406 and the expiration 3D image data subset 408 are then stored in an image dataset 400 in memory component 54, 74 of image analysis system 50 and/or navigation system 70.

Figure 6A:
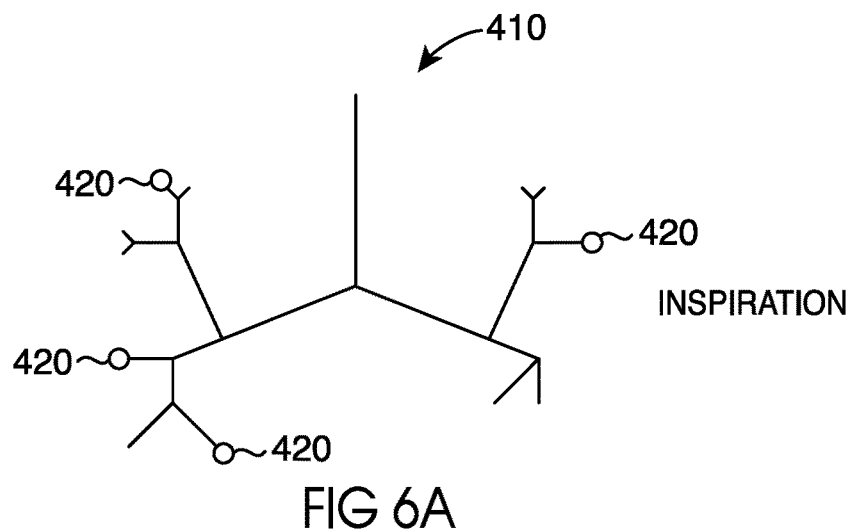
FIG. 6A is a schematic illustration of an inspiration 3D airway model according to an embodiment of the invention.
Figure 6B:
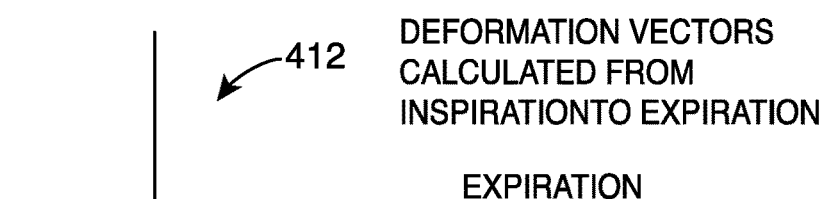
FIG. 6B is a schematic illustration of an expiration 3D airway model according to an embodiment of the invention.
Figure 6C:
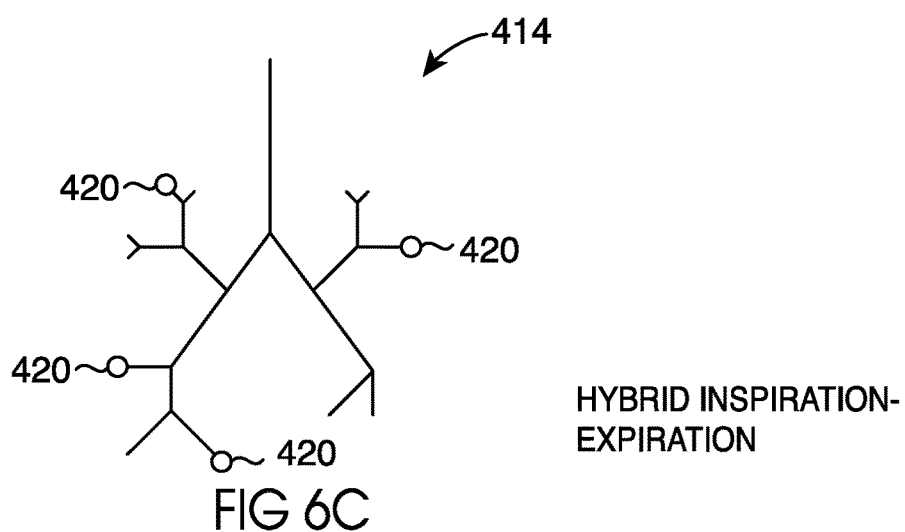
FIG. 6C is a schematic illustration of a hybrid "Inspiration-Expiration" 3D airway model according to an embodiment of the invention.

Additionally, acquiring a population of images at both inspiration and expiration may assist navigation of a steerable catheter during a second time interval. Referring now to FIGS. 6A-6C, in addition to segmenting the markers 22 of PTD 20 from the population of images 402, 404 generated during the first time interval, processor 52 of image analysis workstation 50 generates three-dimensional models of the airway of patient 10 by segmenting the 3D image data subsets 406, 408. In various embodiments, segmentation of the airway may be accomplished using an iterative region growing technique wherein a seed voxel in the airway is selected as an initialization parameter. Voxels neighboring the seed voxel are then evaluated to determine whether they are a part of the airway, form the wall surrounding the airway, or form other tissue. Following segmentation, a surface mesh of the airway may be generated to produce a surface skeleton. The surface of the airway may then be rendered. Other segmentation methods are described herein below, including methods for localized segmentation extension in a region of interest.

As shown in FIG. 6A, a three-dimensional model of the airway of patient 10 at inspiration ("inspiration 3D airway model 410") is generated by segmenting the inspiration 3D image data subset 406. FIG. 6A shows an Inspiration/arms-up pathway registration; this is, generally speaking, the preferred image scan acquisition state for automatic segmentation of the tracheo-bronchial tree. Processor 52 may also segment one or more target tissues 420 (e.g., lesions, lymph nodes, blood vessels, tumors, etc.) which may be navigated to during a second time interval using a variety of medical devices as described more fully elsewhere herein. The segmentation of the target tissue(s) 420 may be refined to define different characteristics of the target tissue, such as, for example, density of the target tissue. Additional image data formats may also be loaded into processor 52, such as, for example, PET or MR and processor 52 may be able to map the CT, PET, and/or MR data to one another. As described herein below, an initial segmentation of an image(s) or image dataset(s) can be extended in a region of interest to aid in navigation or for other use.

As shown at FIG. 6B, a three-dimensional model of the airway of patient 10 at expiration ("expiration 3D airway model 412") is generated by segmenting the expiration 3D image data subset 408. As discussed above, a variety of segmentation algorithms known in the art may be used to generate the initial inspiration and expiration 3D airway models 410, 412. Methods for extending the initial segmentation are described herein below. FIG. 6B shows, in contrast to FIG. 6A, an FRC/arms-down segmentation. Because the patient's 10 lungs are more full of air at inspiration than at expiration, the inspiration 3D airway model 410 includes more structure than the expiration 3D airway model 412. Accordingly, as shown in FIG. 6B, expiration 3D airway model 412 includes fewer structure(s) and the structure(s) are in different locations and/or orientations than at inspiration. However, during a procedure such as directing a navigated steerable catheter to a target tissue within the airway of patient 10 (e.g., during a second time interval), the breathing cycle of patient 10 may be closer to tidal breathing. That is, patient 10 usually never reaches full inspiration during the procedure and thus if the segmentation of the airways of patient 10 at inspiration is used for navigation purposes, there will be significant error in the registration of the segmented airway to patient 10.

In certain embodiments, a hybrid "Inspiration-Expiration" 3D airway model 414 is constructed as shown in FIG. 6C using the inspiration 3D airway model 410 and the expiration 3D airway model 412. The hybrid "Inspiration-Expiration" 3D airway model 414 may be used to reduce or eliminate the errors in registration. To construct the hybrid "Inspiration-Expiration" 3D airway model 414, a population of deformation vector fields is calculated by processor 52, 72 of image analysis system 50 and/or navigation system 70. The deformation vector field comprises vectors from one or more voxels in the inspiration 3D airway model 410 to one or more corresponding voxels in the expiration 3D airway model 412. After the deformation vector field is calculated, the inspiration 3D airway model 410 is deformed to the expiration state of patient 10 using the deformation vector field. Accordingly, the voxels in the inspiration 3D airway model 410 are deformed to match the location, shape, and orientation of the airways of patient 10 at expiration. This results in the hybrid "Inspiration-Expiration" 3D airway model 414, wherein the hybrid "Inspiration-Expiration" 3D airway model 414 contains all of the structural information of the airways of patient 10 depicted in inspiration 3D airway model 410. However, this structural information is now more closely matched to the location, shape, and orientation of the airways of patient 10 depicted in expiration 3D airway model 412. Accordingly, the deformation vectors represent not only a change in location of the structure of the airway but a change in shape of the structure of the airway from inspiration to expiration.

Figure 7:
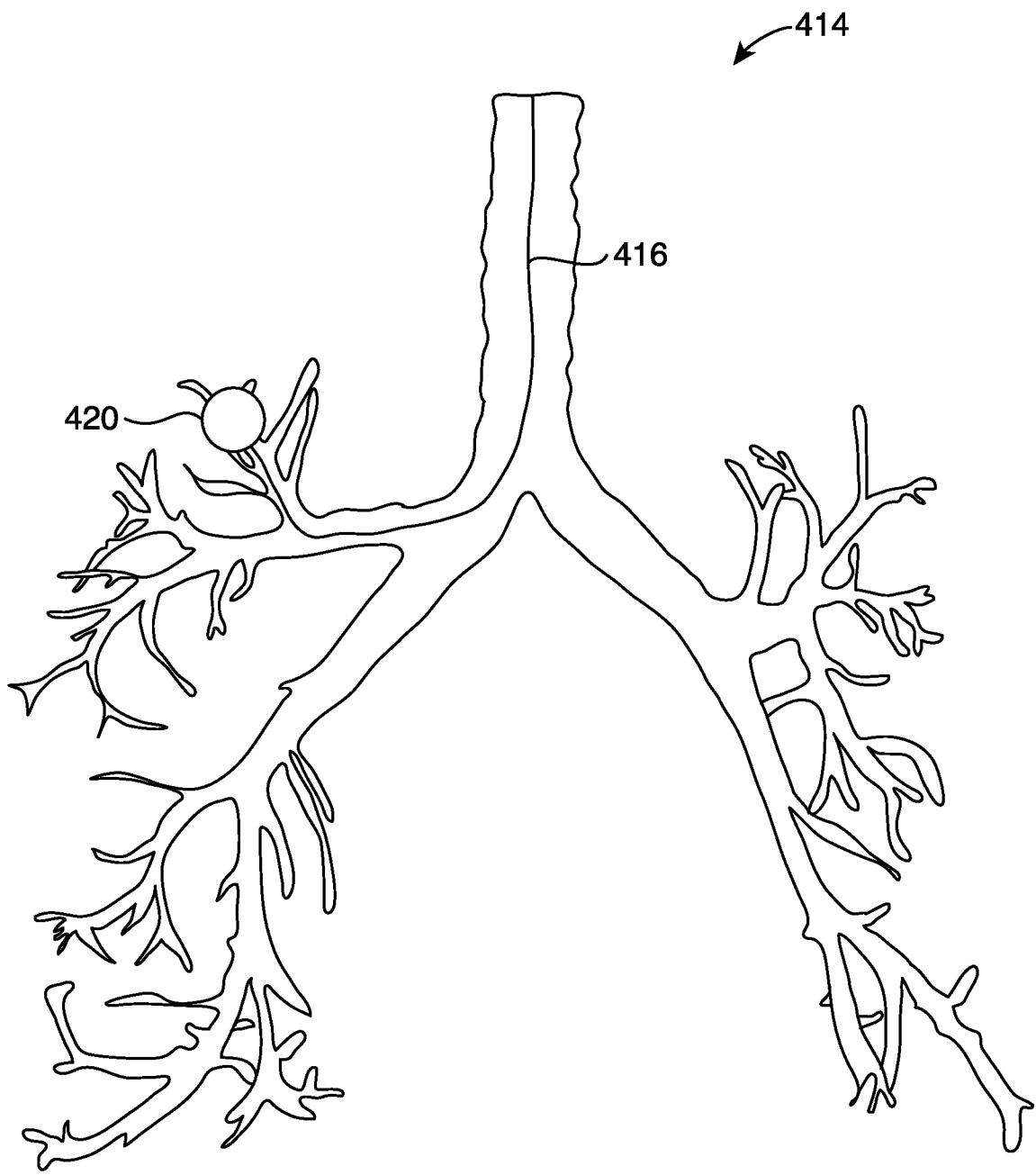
FIG. 7 is a front perspective view of a hybrid "Inspiration-Expiration" 3D airway model according to an embodiment of the invention.

FIG. 7, illustrates a 3D representation of hybrid "Inspiration-Expiration" 3D airway model 414 which includes a target tissue 420 segmented by processor 52, 72. This 3D representation of hybrid "Inspiration-Expiration" 3D airway model 414 may include surface information. Hybrid "Inspiration-Expiration" 3D airway model 414 may additionally include navigation pathway 416. Image analysis system 50 and/or navigation system 70 may calculate navigation pathway 416 from the entry of the airway to the location of target tissue 420. In certain embodiments, navigation pathway 416 may be an optimal endobronchial path to a target tissue. For example, navigation pathway 416 may represent the closest distance and/or closest angle to the target tissue. A physician or other healthcare professional may follow navigation pathway 416 during an image guided intervention to reach the location of target tissue 420.

Although target tissue 420 locations and navigation pathway(s) 416 may be automatically calculated by image analysis system 50 and/or navigation system 70, a physician or other healthcare professional may manually adjust target tissue 420 locations and/or navigation pathway(s) 416. As described herein with reference to FIGS. 14-19, the navigation pathway 416 can be improved based on additional information obtained during localized segmentation extension methods according to embodiments set forth below.

In general, the embodiments described herein have applicability in "Inspiration to Expiration"-type CT scan fusion. According to various methods, the user navigates on the expiration 3D image data subset 408 for optimal accuracy, while using the inspiration 3D image data subset 406 to obtain maximum airway segmentation. In one embodiment, for example, a user could complete planning and pathway segmentation on the inspiration 3D image data subset 406 of patient 10. Preferably, a deformation vector field is created between at least two datasets (e.g., from inspiration 3D image data subset 406 to expiration 3D image data subset 408). The deformation or vector field may then be applied to the segmented vessels and/or airways and navigation pathway 416 and target tissue 420 locations. In these and other embodiments, the deformation or vector field may also be applied to multiple image datasets or in a progressive way to create a moving underlying image dataset that matches the respiratory or cardiac motion of patient 10.

By way of example, in certain embodiments, "Inspiration to Expiration" CT fusion using the lung lobe centroid and vector change to modify an airway model may also be applicable. In accordance with various embodiments, this technique is used to translate and scale each airway based on the lung lobe change between inspiration images and expiration images. The lung is constructed of multiple lobes and these lobes are commonly analyzed for volume, shape, and translation change. Each lobe changes in a very different way during the patient's breathing cycle. Using this information to scale and translate the airways that are located in each lobe, it is possible to adapt for airway movement. This scaled airway model may then be linked to the 4D tracking of the patient as described herein.

In various aspects, the systems and methods described herein involve modifying inspiration images generated by imaging device 40 (e.g., CT, CT/PET, MRI, etc.) to the expiration cycle for navigation. It is well understood that the patient's airways are contained within multiple lobes of the lung. It is also understood that airways significantly change between inspiration and expiration. In certain embodiments, to increase the accuracy of the map for navigation, it may be beneficial to include the detail of the inspiration images, coupled with the ability to navigate it accurately during expiration. For many patients, the expiration state may be the most repeatable point in a patient's breath cycle. In preferred embodiments, this modification may be carried out in accordance with the following steps:

1) Generate a population of images of patient 10 at both inspiration and expiration using imaging device 40;
2) Segment the airways in both the inspiration and expiration images;
3) Segment the lung lobes in both the inspiration and expiration images (as the lung lobes are identifiable in both the inspiration and expiration images with a high degree of accuracy);
4) Determine a volume difference for each lung lobe between inspiration and expiration, use this change to shrink the airway size from the inspiration to the expiration cycle. Preferably, this is done for each individual lobe, as the percentage change will typically be different for each lobe.
5) Determine the centroid for each lung lobe and the vector change in motion from the main carina in both inspiration images and expiration images. This vector may then be used to shift the airways that are associated with each lung lobe. A centroid for the airway may be calculated based on the segmented branches. For each airway branch in the segmentation, it includes a tag that associates it with the respective lung lobe. The central airway including the main carina and initial airway branches for each lobe that is linked according to the expiration scan location of these points. Next, a plane may be defined using the main carina and initial airway branch exits to determine the vector change for each lobe.

Among the lobes to modify, for example:
left inferior lobe—the bottom lobe of the lung on the left side of patient 10;
left superior lobe—the top lobe of the lung on the left side of patient 10.
right inferior lobe—the bottom lobe of the lung on the right side of patient 10;
right middle lobe—the middle lobe of the lung on the right side of patient 10;
right superior lobe—the top lobe of the lung on the right side of patient 10.

Exemplary calculations are as follows:
Inspiration Airway—Left Inferior Lobe (LIL)×70% (reduction in volume Inspiration to Expiration calculated) =ExAirwayLIL;
Determine Expiration Central Airway points (Main Carina and Initial Airway branches) based upon segmentation;
Shift ExAirwayLIL by vector distance (3 cm, 45 degrees up and back from main carina) that LIL centroid moved from inspiration to expiration.

Preferably, this process is repeated for each lobe. In certain embodiments, the completion of 5 lobes will result in a hybrid "Inspiration-Expiration" 3D airway model for patient 10.

In various embodiments, the target location for the patient may be selected in the expiration images and applied to the hybrid "Inspiration-Expiration" 3D airway model 414. Alternatively, it may be selected in the inspiration images and adjusted based on the same or similar criteria as the inspiration airways. In either case, it may be adjusted individually or linked to the airway via a 3D network and moved in the same transformation.

A deformation field may also be included in the analysis in various other embodiments described herein. For example, the deformation field may be applied to fuse 3D fluoroscopic images to CT images to compensate for different patient orientations, patient position, respiration, deformation induced by the catheter or other instrument, and/or other changes or perturbations that occur due to therapy delivery or resection or ablation of tissue.

Following the generation of hybrid "Inspiration-Expiration" 3D airway model 414, during a second time interval, a medical procedure is then performed on patient 10 with PTD 20 coupled to patient 10 at the same location as during the first time interval when the population of pre-procedural images were taken. Preferably, the second time interval immediately follows the first time interval. However, in certain embodiments, second time interval may occur several hours, days, weeks or months after the first time interval. After hybrid "Inspiration-Expiration" 3D airway model 414 is generated and one or more target tissues 420 are identified and one or more navigation pathways 416 are calculated, this information is transferred from image analysis system 50 to navigation system 70. This transfer may be done according to the DICOM (Digital Imaging and Communications in Medicine) standard as known in the art. It will be understood that the transfer may be done using any method and according to any standard without departing from the scope of the invention. For example, this transfer may be accomplished between image analysis system 50 to navigation system 70 using a variety of methods, including, but not limited to, a wired connection, a wireless connection, via CD, via a USB device, via disk, etc.

It should be noted that image dataset 400 may be supplemented, replaced or fused with an additional image dataset. In one embodiment, for example, during the second time interval an additional population of images may be taken. In other embodiments, for example, after the second time interval an additional population of images may be taken. By generating one or more additional image datasets, potential changed physical parameters of patient such as patient 10 movement, anatomical changes due to resection, ablation, general anesthesia, pneumothorax, and/or other organ shift may be accounted for during the procedure. Accordingly, images from CT-Fluoro, fluoroscopic, ultrasound or 3D fluoroscopy may be imported into image analysis system 50 and/or navigation system 70.

Using the respiratory signal derived from PTD 20, navigation system 70 selects an image from the population of pre-procedural images 402, 404 taken during the first time interval that indicates a distance or is grouped in a similar sequence of motion between corresponding markers 22 at a given instant in time, that most closely approximates or matches the distance or similar sequence of motion between the selected localization elements 24. The process of comparing the distances is described in more detail below. Thus, navigation system 70 displays images corresponding to the actual movement of the targeted anatomy during the medical procedure being performed during the second time interval. The images illustrate the orientation and shape of the targeted anatomy during a path of motion of the anatomy, for example, during inhaling and exhaling.

Figure 8:
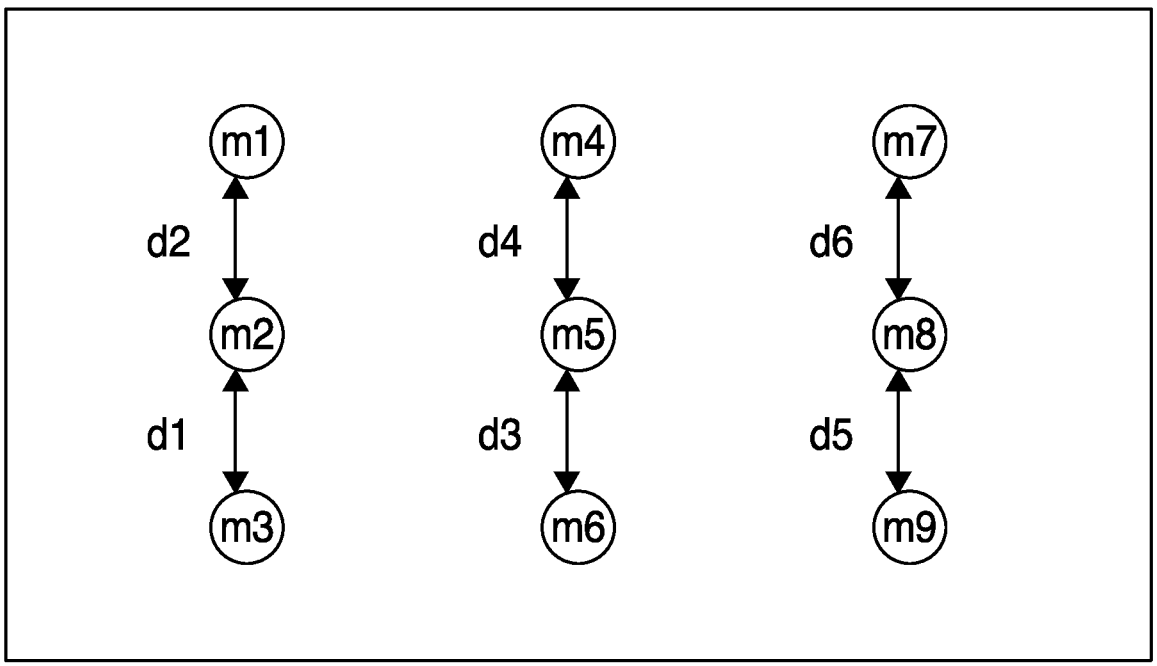
FIG. 8 is a schematic illustrating vector distances of the patient tracking device according to an embodiment of the invention.

FIG. 8 illustrates an example set of distances or vectors d1 through d6 between a set of markers 22, labeled m1 through m9 that are disposed at spaced locations on PTD 20. As described above, a population of pre-procedural images is taken of a patient 10 to which PTD 20 is coupled during a first time interval. The distances between markers 22 are determined for multiple instants in time through the path of motion of the dynamic body (e.g., the respiratory cycle of the patient). Then, during a medical procedure, performed during a second time interval, localization elements 24 (not shown in FIG. 8) proximate the location of markers 22 provide position data for localization elements 24 to localization device 76 (not shown in FIG. 8). Navigation system 70 uses the position data to determine distances or vectors between localization elements 24 for multiple instants in time during the medical procedure or second time interval.

Figure 9A:
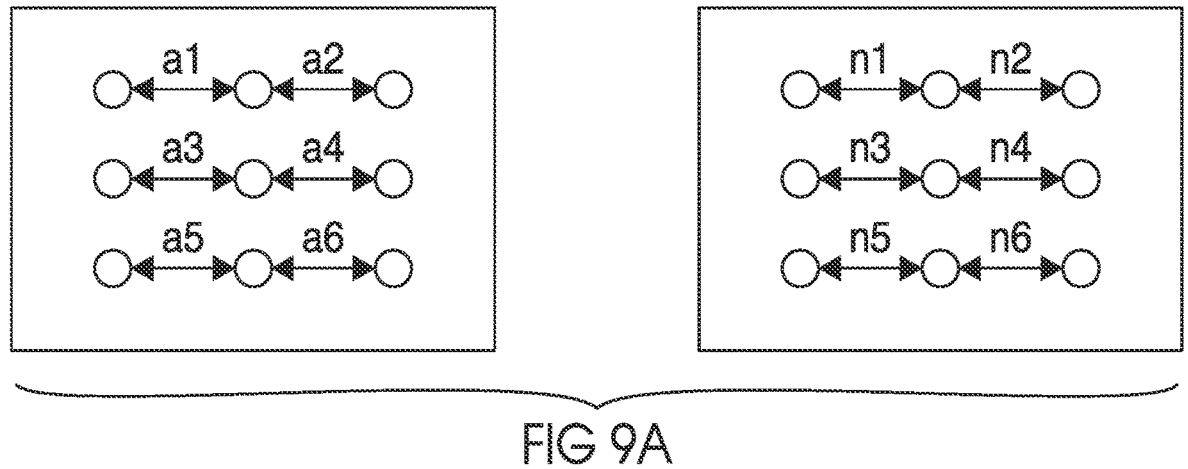
FIG. 9A is a schematic illustrating vector distances from a localization element on the patient tracking device according to an embodiment of the invention.

FIG. 9A shows an example of distance or vector data from localization device 76. Vectors a1 through a6 represent distance data for one instant in time and vectors n1 through n6 for another instant in time, during a time interval from a to n. As previously described, the vector data may be used to select an image from the population of pre-procedural images that includes distances between the markers m1 through m9 that correspond to or closely approximate the distances a1 through a6 for time a, for example, between the localization elements. The same process may be performed for the vectors n1 through n6 captured during time n.

Figure 9B:
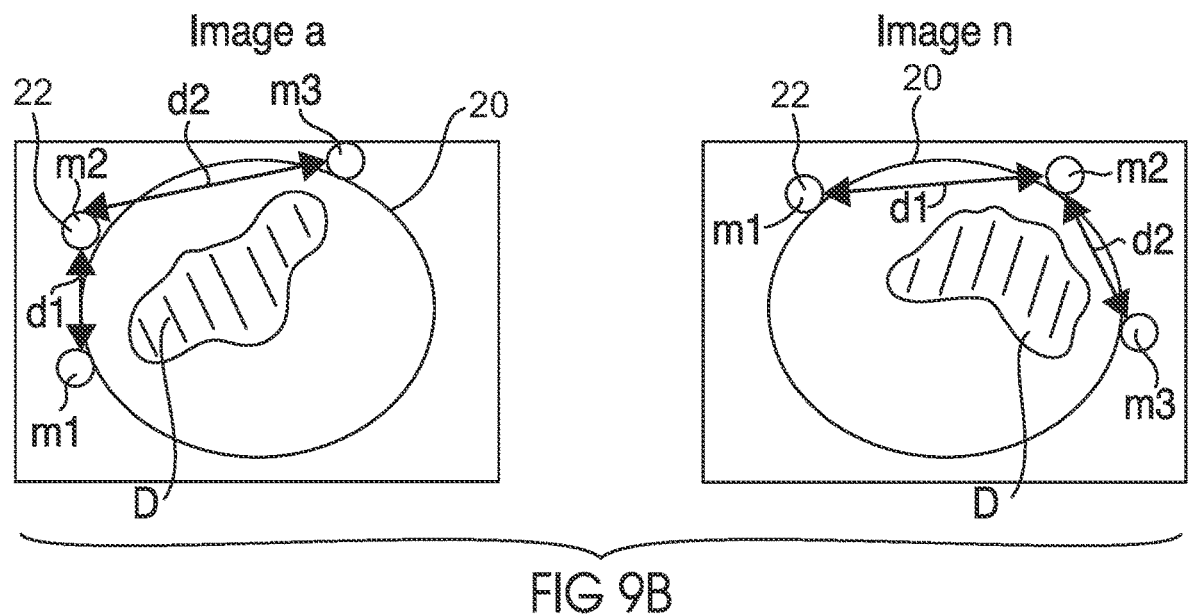
FIG. 9B is a schematic illustrating vector distances from an image dataset according to an embodiment of the invention.

One method of selecting the appropriate image from the population of pre-procedural images 402, 404 is to execute an algorithm that sums all of the distances a1 through a6 and then search for and match this sum to an image containing a sum of all of the distances d1 through d6 obtained pre-procedurally from the image data that is equal to the sum of the distances a1 through a6. When the difference between these sums is equal to zero, the relative position and orientation of the anatomy or dynamic body D during the medical procedure will substantially match the position and orientation of the anatomy in the particular image. The image associated with distances d1 through d6 that match or closely approximate the distances a1 through a6 may then be selected and displayed. For example, FIG. 9B illustrates examples of pre-procedural images, Image a and Image n, of a dynamic body D that correspond to the distances a1 through a6 and n1 through n6, respectively. An example of an algorithm for determining a match is as follows:

Does $\Sigma$ ai=$\Sigma$ di (i=1 to 6 in this example) OR
Does $\Sigma$ (ai−di)=0 (i=1 to 6 in this example).

If yes to either of these, then the image is a match to the vector or distance data obtained during the medical procedure.

Figure 10:
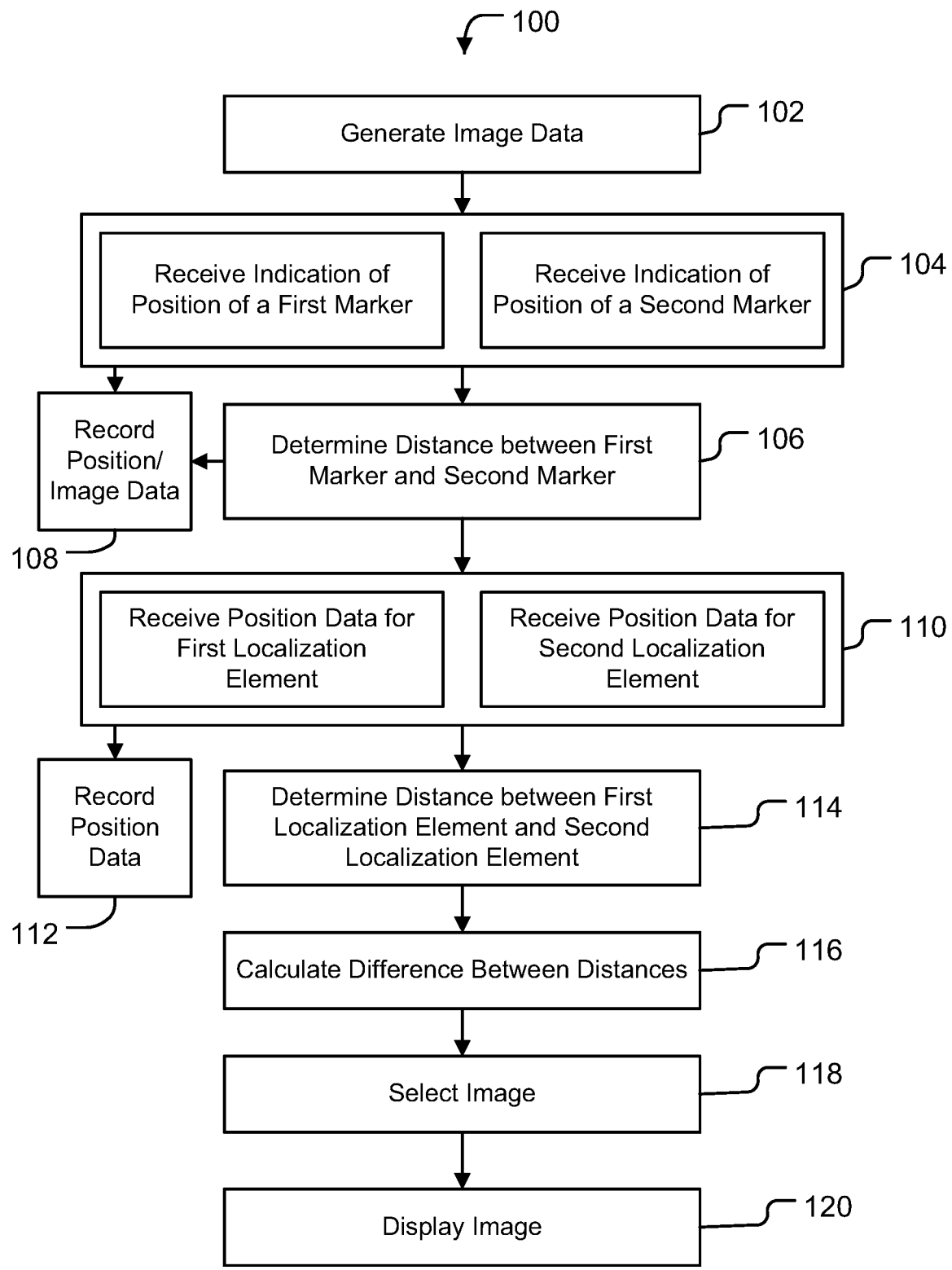
FIG. 10 is a flowchart illustrating a method according to an embodiment of the invention.

FIG. 10 is a flowchart illustrating a method according to an embodiment of the invention. A method 100 includes at step 102 generating image data during a pre-procedural or first time interval. As discussed above, a population of images are generated of a dynamic body, such as patient 10, using imaging device 40 (e.g., CT Scan, MRI, etc.). The image data is associated with one or more images generated of PTD 20 coupled to a dynamic body, where PTD 20 includes two or more markers 22. In other words, the image data of the dynamic body is correlated with image data related to PTD 20. The one or more images may be generated using a variety of different imaging devices as described previously. The image data include an indication of a position of a first marker and an indication of a position of a second marker, as illustrated at step 104. The image data include position data for multiple positions of the markers during a range or path of motion of the dynamic body over a selected time interval. As described above, the image data include position data associated with multiple markers, however, only two are described here for simplicity. A distance between the position of the first marker and the position of the second marker is determined for multiple instants in time during the first time interval, at step 106. As also described above, the determination may include determining the distance based on the observable distance between the markers on a given image. The image data, including all of the images received during the first time interval, the position, and the distance data is recorded in a memory component at step 108.

Then at step 110, during a second time interval, while performing a medical procedure on patient 10 with PTD 20 positioned on patient 10 at substantially the same location, position data is received for a first localization element and a second localization element. Localization elements 24 of PTD 20 are proximate markers 22, such that the position data associated with localization elements 24 is used to determine the relative position of markers 22 in real-time during the medical procedure. The position data of localization elements 24 are recorded in a memory component at step 112.

A distance between the first and second localization elements is determined at step 114. Although only two localization elements 24 are described, as with the markers, position data associated with more than two localization elements may be received and the distances between the additional localization elements may be determined.

The next step is to determine which image from the population of images taken during the first time interval represents the relative position and/or orientation of the dynamic body at a given instant in time during the second time interval or during the medical procedure. To determine this, at step 116, the distance between the positions of the first and second localization elements at a given instant in time during the second time interval determined in step 114 are compared to the distance(s) determined in step 106 between the positions of the first and second markers obtained with the image data during the first time interval.

An image is selected from the first time interval that best represents the same position and orientation of the dynamic body at a given instant in time during the medical procedure. To do this, the difference between the distance between a given pair of localization elements during the second time interval is used to select the image that contains the same distance between the same given pair of markers from the image data received during the first time interval. This is accomplished, for example, by executing an algorithm to perform the calculations. When there are multiple pairs of markers and localization elements, the algorithm may sum the distances between all of the selected pairs of elements for a given instant in time during the second time interval and sum the distances between all of the associated selected pairs of markers for each instant in time during the first time interval when the pre-procedural image data was received.

When an image is found that provides the sum of distances for the selected pairs of markers that is substantially the same as the sum of the distances between the localization elements during the second time interval, then that image is selected at step 118. The selected image is then displayed at step 120. The physician or other healthcare professional may then observe the image during the medical procedure. Thus, during the medical procedure, the above process may be continuously executed such that multiple images are displayed and images corresponding to real-time positions of the dynamic body may be viewed.

In addition to tracking the location of PTD 20, navigation system 70 (see FIG. 3) may also track any type of device which includes one or more localization elements. The localization elements in the medical devices may be substantially similar or identical to localization elements 24 of PTD 20. The devices preferably include medical devices, including, but not limited to, steerable catheters, needles, stents, ablation probes, biopsy devices, guide wires, forceps devices, brushes, stylets, pointer probes, radioactive seeds, implants, endoscopes, energy delivery devices, therapy delivery devices, delivery of energy activated substances (e.g., porfimer sodium) and energy devices, radiofrequency (RF) energy devices, cryotherapy devices, laser devices, microwave devices, diffuse infrared laser devices, etc. In certain embodiments, the location of these devices is tracked in relation to PTD 20. In other embodiments, for example, these devices are tracked in relation to electromagnetic field generator 62, 82. It is also envisioned that at least some of these medical devices may be wireless or have wireless communications links. It is also envisioned that the medical devices may encompass medical devices which are used for exploratory purposes, testing purposes or other types of medical procedures. Tracked or navigated devices can be used to supplement segmentation information, as described herein below.

Figure 11:
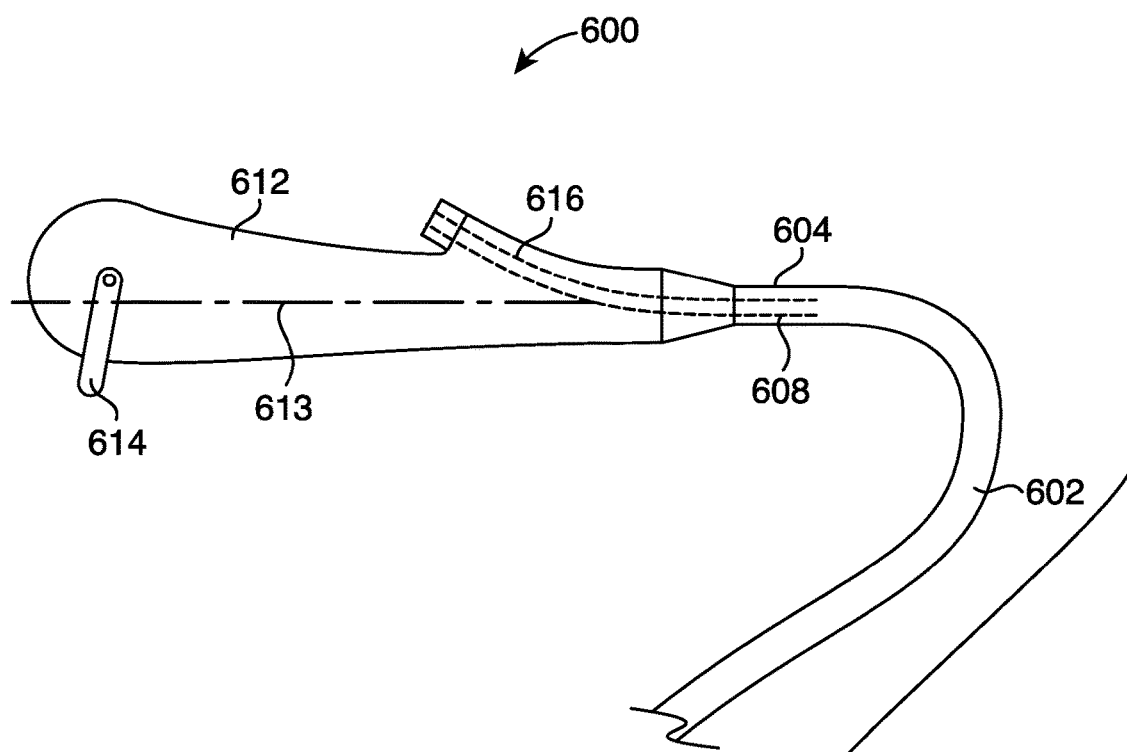
FIG. 11 is a left side view of a steerable catheter according to an embodiment of the invention.
Figure 11A:
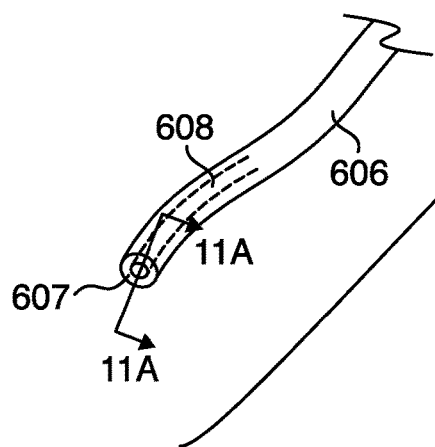
FIG. 11A is a left partial section view of a steerable catheter according to an embodiment of the invention.
Figure 11A:
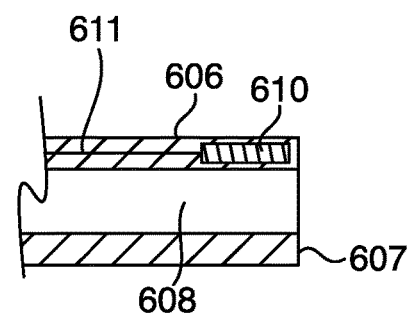

One embodiment of a medical device which may be tracked by navigation system 70 is illustrated in FIGS. 11 and 11A. In one embodiment of the present invention, a navigated surgical catheter that is steerable 600 (referred herein to as "steerable catheter") may be used to gain access to, manipulate, remove, sample or otherwise treat tissue within the body including, but not limited to, for example, heart or lung tissue. Steerable catheter 600 comprises an elongate flexible shaft 602 having a proximal end portion 604, a distal end portion 606 terminating in tip 607, and one or more working channels 608 extending from proximal end portion 604 to tip 607. As shown in FIG. 11A, one or more localization elements 610 that are detectable by navigation system 70 are disposed proximate the distal end portion 606 of elongate flexible shaft 602. Accordingly, the position and orientation (POSE) of localization elements 610 are tracked by localization device 76 of navigation system 70. The one or more localization elements 610 are connected by wire 611 to navigation system 70; in alternative embodiments, the one or more localization elements 610 may be wirelessly connected to navigation system 70. In certain embodiments, localization elements 610 comprise six (6) degree of freedom (6 DOF) electromagnetic coil sensors. In other embodiments, localization elements 610 comprise five (5) degree of freedom (5 DOF) electromagnetic coil sensors. In other embodiments, localization elements 610 comprise other localization devices such as radiopaque markers that are visible via fluoroscopic imaging and echogenic patterns that are visible via ultrasonic imaging. In yet other embodiments, localization elements 610 may be, for example, infrared light emitting diodes, and/or optical passive reflective markers. Localization elements 610 may also be, or be integrated with, one or more fiber optic localization (FDL) devices. Accordingly, in certain embodiments, localization elements 610 may be substantially similar or identical to localization elements 24 of PTD 20. In other embodiments the steerable catheter may be non-navigated, such that it does not include any localization elements.

Steerable catheter 600 further comprises handle 612 attached to the proximal end portion 604 of elongate flexible shaft 602. Handle 612 of steerable catheter 600 includes steering actuator 614 wherein distal end portion 606 is moved "up" and "down" relative to proximal end portion 604 by manipulating steering actuator 614 "up" and "down," respectively. Additionally, distal end portion 606 is moved "left" and "right" relative to proximal end portion 604 by rotating handle 612 "left" and "right," respectively, about handle longitudinal axis 613. It will be understood that steering actuator 614 and handle 612 are connected to a steering mechanism (not shown) on the inside of steerable catheter 600 which is connected to distal end portion 606 of elongate flexible shaft 602 for causing the deflection in distal end portion 606. Port 616, disposed on handle 612, provides access to working channel(s) 608 in elongate flexible shaft 602 of steerable catheter 600, such that a medical device may be inserted into working channel(s) 608 through port 616.

Figure 12A:
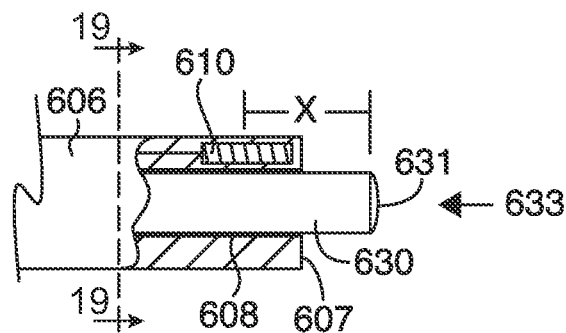
FIG. 12A is a left partial cut away view of a steerable catheter according to an embodiment of the invention.
Figure 12B:
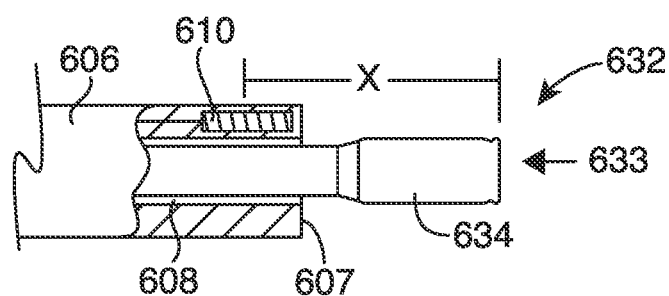
FIG. 12B is a left partial cut away view of a steerable catheter according to an embodiment of the invention.

As shown in FIGS. 12A and 12B, any number of medical devices or therapies may be inserted into working channel(s) 608 and/or extended out of tip 607 to deliver the medical devices or therapies to a target tissue. The medical devices may include, but are not limited to, imaging devices 633, tissue sensing devices 632, biopsy devices, therapy devices, steerable catheters, endoscopes, bronchoscopes, percutaneous devices, percutaneous needles, pointer probes, implants, stents, guide wires, stylets, etc. In certain embodiments, imaging devices 633 include, but are not limited to, bronchoscopic video cameras 630, endobronchial ultrasound (EBUS) devices 634, optical coherence tomography (OCT) devices, probe based Confocal Laser Endomicroscopy (pCLE) devices, or any known imaging device insertable into working channel 608 of steerable catheter 600. Tissue sensing device 632 may be any type of device which may be used to determine the presence of a target tissue in patient 10. In certain embodiments, tissue sensing device 632 may include, but is not limited to, imaging device 633, a cell analysis device, a cancer detecting device, an exhaled breath condensate analyzer, a physiological characteristic sensor, a chemical analysis device, an aromatic hydrocarbon detection device, vacuum collection device, etc. The sensitivity of certain of the tissue sampling devices, such as aromatic hydrocarbon detection devices are dependent upon the density of the sample collected. Thus, by navigating steerable catheter 600 near the desired target tissue a sample of higher density may be captured and analyzed. Additionally, a vacuum collection device may be navigated using steerable catheter 600 to near the desired target tissue and/or an airway branch within one or two segments of the desired target tissue, and an air sample may be captured. In certain embodiments, therapy devices include, but are not limited to, ablation probes, energy delivery devices, radioactive seeds, delivery of energy activated substances (e.g., porfimer sodium) and energy devices, radiofrequency (RF) energy devices, cryotherapy devices, laser devices, microwave devices, diffuse infrared laser devices, fluids, drugs, combinations thereof, or the like). In certain embodiments, biopsy devices include, but are not limited to, needles, forceps devices, brushes, etc. In certain embodiments, steerable catheter 600 may also include a suction capability.

As illustrated in FIG. 12A, for example, in certain embodiments, imaging device 633 is a bronchoscopic video camera 630. Bronchoscopic video camera 630 may be inserted into working channel 608 and/or extended out distal end portion 606 of navigated steerable catheter 600. By inserting bronchoscopic video camera 630 into working channel 608 of steerable catheter 600, steerable catheter 600 may be used like a typical steerable bronchoscope, as described more fully elsewhere herein.

As shown in FIG. 12B, tissue sensing device 632 may be an imaging device 633, wherein imaging device 633 is an endobronchial ultrasound (EBUS) device 634; however, as described above, it will be understood that imaging device 633 may include, but is not limited to, bronchoscopic video camera 630, an optical coherence tomography (OCT) device, a probe based Confocal Laser Endomicroscopy (pCLE) device, or any known imaging device insertable into working channel 608 of steerable catheter 600.

In embodiments, where tissue sensing device 632 is imaging device 633, imaging device 633 may be able to generate a population of images of the target tissue(s), wherein the target tissue(s) may be in the airway, on the wall of the airway, in the wall of the airway, and/or beyond the wall of the airway. That is, the imaging device(s) may be able to generate images of target tissue(s) not only inside the airway but may generate images of target tissue(s) and other anatomical structures inside and/or beyond the wall of the airway. Thus, in certain embodiments, sub-surface target tissue may be imaged using the imaging device(s). Accordingly, using endobronchial ultrasound (EBUS) device 634, an optical coherence tomography (OCT) device, a probe based Confocal Laser Endomicroscopy (pCLE) device, etc. while tracking the position and orientation (POSE) of localization element 610 of steerable catheter 600, as described herein, multiple 3D volumes of image data regarding target tissue(s) and other anatomical structures inside and/or beyond the wall of the airway may be collected and a larger 3D volume of collected data may be constructed. Knowing the 3D location and orientation of the multiple 3D volumes will allow the physician or other healthcare professional to view a more robust image of, for example, pre-cancerous changes of target tissue(s) in patient 10. This data may also be correlated to pre-acquired or intra-procedurally acquired image dataset 400 to provide additional information.

Additionally, in certain embodiments wherein steerable catheter 600 includes multiple working channels 608, multiple medical devices may be inserted into the multiple working channels 608. For example, bronchoscopic video camera 630 may be inserted into one working channel and a medical device such as a needle, forceps device or a brush may be inserted into a second working channel. Accordingly, a real-time image feed from bronchoscopic video camera 630 may be used to view the operation of the medical device. Although a steerable catheter has been described, it will be understood that any type of steerable medical device may be used in accordance with the methods described herein, including, but not limited to, endoscopes, bronchoscopes, etc. without departing from the scope of the invention. It is understood that other medical devices may be tracked by navigation system 70, such as a percutaneous needle or other device, such as described in U.S. Ser. No. 15/290,822, for example, the entirety of which is incorporated herein by reference.

In various embodiments, any of the medical devices described herein that may be inserted into working channel(s) 608, 658 of steerable catheter 600 and/or other medical devices may be tracked individually with an integrated localization element (e.g., an electromagnetic (EM) sensor). Accordingly, the medical devices may be tip tracked. Additionally, wherein the inserted medical device is an ablation probe, ablation models may be displayed to assist in optimal placement of the ablation probe for treatment. It will be understood that the medical devices may be delivered endobronchially, percutaneously, and/or endobronchially and percutaneously simultaneously.

Referring again to navigation system 70, navigation system 70 may display on display 80 multiple images which may assist a physician or other healthcare professional in conducting the methods described herein. Image dataset 400 generated during the first time interval may be registered to patient 10 using PTD 20. As described above, localization elements 24 of PTD 20 are proximate markers 22 and because one or more markers 22 of PTD 20 are visible in image dataset 400 and localization elements 24 corresponding to the one or more markers 22 are tracked by navigation system 70, image dataset 400 may be registered to patient 10. This registration may be manually accomplished or may be automatically accomplished by navigation system 70.

In addition to or alternative to registration using PTD 20, registration may be completed by different known techniques. First, point-to-point registration may be accomplished by identifying points in an image space and then touching the same points in patient space. These points are generally anatomical landmarks that are easily identifiable on the patient. Second, lumen registration may be accomplished by generating a point cloud within the airways of patient 10 and matching the shape of the generated point cloud to an inspiration 3D airway model 410, an expiration 3D airway model 412, and/or a hybrid "Inspiration-Expiration" 3D airway model 414. Using four-dimensional tracking (4D) the point cloud may be generated at the appropriate respiration cycle to match inspiration 3D airway model 410, an expiration 3D airway model 412, and/or a hybrid "Inspiration-Expiration" 3D airway model 414. Generation of a point cloud is more fully described in U.S. Ser. No. 13/773,984, entitled "Systems, Methods and Devices for Forming Respiratory-Gated Point Cloud for Four Dimensional Soft Tissue Navigation," filed on Feb. 22, 2013, which is hereby incorporated by reference. Third, surface registration may involve the generation of a surface in patient 10 space by either selecting multiple points or scanning, and then accepting the best fit to that surface in image space by iteratively calculating with processor 72 until a surface match is identified. Fourth, repeat fixation devices entail repeatedly removing and replacing a device (i.e., dynamic reference frame, etc.) in known relation to patient 10 or image fiducials of patient 10. Fifth, two-dimensional (2D) image datasets may be registered to three-dimensional (3D) image datasets wherein, the two dimensional image datasets may include, but are not limited to, fluoroscopic images, ultrasound images, etc. and the three-dimensional (3D) image datasets may include, but are not limited, to computed tomography (CT) images, fused computed tomography—positron emission tomography (CT/PET) images, magnetic resonance imaging (MRI) images. Sixth, automatic registration may be accomplished by first attaching a dynamic reference frame to patient 10 prior to acquiring image data. It is envisioned that other known registration procedures are also within the scope of the present invention, such as that disclosed in U.S. Pat. No. 6,470,207, entitled Navigational Guidance via Computer-Assisted Fluoroscopic Imaging", filed on Mar. 23, 1999, which is hereby incorporated by reference.

Figure 13:
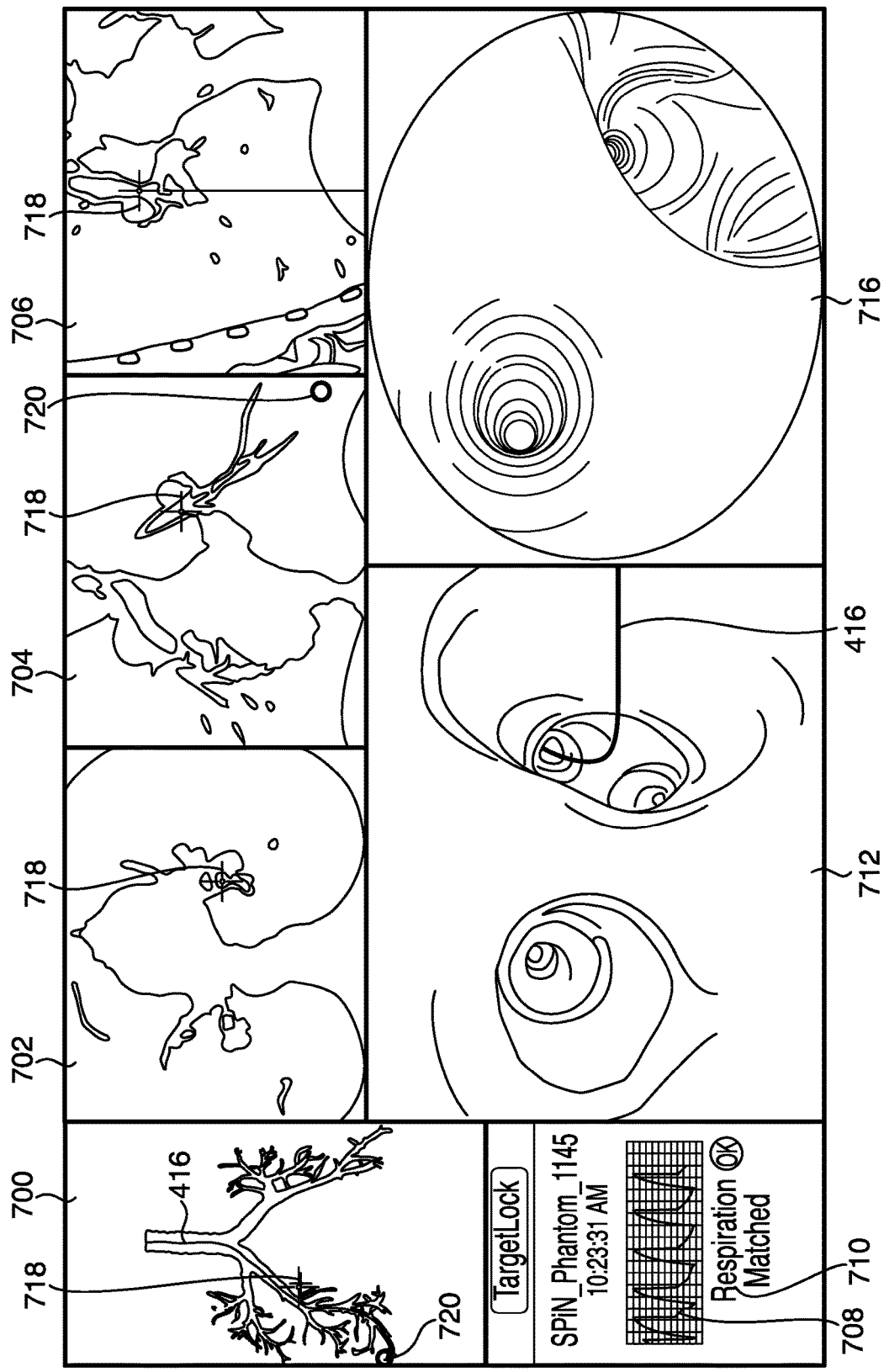
FIG. 13 illustrates a population of images which may be displayed on a display of a navigation system according to an embodiment of the invention.

After image dataset 400 is registered to patient 10, navigation system 70 displays on display 80 a variety of images as illustrated in FIG. 13. For example, as shown in panel 700, hybrid "Inspiration-Expiration" 3D airway model 414 may be displayed. Additionally, as shown in panel 700, an indicia 718 (shown as a crosshair) of the location of steerable catheter 600 is displayed. In certain embodiments, for example, indicia 718 indicates the location of distal end portion 606 of steerable catheter 600. In other embodiments, for example, indicia 718 indicates the location of localization element 610 of steerable catheter 600. In yet other embodiments, for example, indicia 718 indicates the location of tip 607 of steerable catheter 600. That is, navigation system 70 may be able to display an indicia indicating the location of a portion of steerable catheter 600 based on the tracked location of localization element 610. For example, if localization element 610 is disposed 5 mm from tip 607 of steerable catheter 600, the 5 mm distance may be taken into account by navigation system 70 and the indicia of tip 607 indicating the location of tip 607 may be displayed and not the location of localization element 610. An indicia 720 (shown as a circle) of an initial target tissue location may also be displayed on display 80 by navigation system 70 as shown in panel 700. Indicia 718, 720 are shown as a crosshair and circle, respectively; however, it is envisioned that other indicia may be used to indicate the location of steerable catheter 600, initial target tissue location, confirmed target tissue location, location of a percutaneous needle, and/or any other target tissue or medical device. For example, indicia may have different shapes, colors, sizes, line weights and/or styles, etc. without departing from the scope of the invention.

Furthermore, navigation system 70 may be able to simulate and display axial, coronal and oblique images based on the position and orientation (POSE) of localization element 610 of steerable catheter 600, as shown in panels 702, 704, and 706. To simulate these views, navigation system 70 may modify one or more images from image dataset 400 using known image manipulation techniques. Additionally, navigation system 70 may simulate and/or display orthogonal image slices, oblique or off-axis image slices, volume rendered images, segmented images, fused modality images, maximum intensity projection (MIPS) images, video, and video enhanced images. As shown, indicia of 718 of steerable catheter 600 and/or an indicia 720 of an initial target tissue location may also be displayed, as shown in panels 702, 704, and 706.

In various embodiments as shown in panel 712, navigation system 70 also simulates a virtual volumetric scene within the body of patient 10, such as the airways of patient 10, from a point of view of a medical device, such as steerable catheter 600, as it is being navigated into and/or through patient 10. This virtual volumetric scene is a computer-generated visualization of a bronchoscopy procedure and simulates what would be viewed by a bronchoscopic video camera inserted into the airways. To simulate the virtual volumetric scene, navigation system 70 modifies one or more images from image dataset 400 using known image manipulation techniques. For example, navigation system 70 may be able to simulate the virtual volumetric scene using inspiration 3D airway model 410, expiration 3D airway model 412, and/or hybrid "Inspiration-Expiration" 3D airway model 414. Accordingly, navigation system 70 renders an internal view of 3D airway model(s) 410, 412, and/or 414 based on a virtual bronchoscope video camera position, for example, by applying certain surface properties (e.g., Lambertian), diffuse shading model(s), and perspective projection camera model(s). Virtual lighting and shading may be applied to the rendered view to further enhance the virtual volumetric scene. The field of view (FOV) may be changed to match the field of view of bronchoscopic video camera 630 (see FIG. 12A). The point of view may be adjusted to match bronchoscopic video camera 630 or to display a virtual volumetric scene from different points along the airway or outside the airway. Navigation system 70 may also be able to display a navigation pathway 416 in the virtual volumetric scene. Accordingly, the virtual volumetric scene may allow a physician or other healthcare professional to review the navigation pathway 416 prior to inserting steerable catheter 600 and/or other medical device into patient 10. Additionally, in certain embodiments, an indicia of the location of localization element 610 of steerable catheter 600 and/or an indicia of an initial target tissue location may also be displayed.

Additionally, in various embodiments as shown in panel 716, navigation system 70 also displays a real-time image feed from bronchoscopic video camera 630 inserted into working channel 608 of steerable catheter 600. The real-time image feed may be static images or moving video. The real-time image feed may assist the physician or other healthcare professional in navigating steerable catheter 600 to proximate the initial location of the target tissue. Thus, by inserting bronchoscopic video camera 630 into working channel 608 of steerable catheter 600 (see FIG. 12A), steerable catheter 600 may be used like a typical steerable bronchoscope. Typical steerable bronchoscopes are used to visually inspect the airways of a patient and have a fixed bronchoscopic video camera in addition to one or more working channels. Typical steerable bronchoscopes may have steering actuators and steering mechanisms that permit them to be steered much like steerable catheter 600. Because the bronchoscopic video camera of a typical steerable bronchoscope is fixed during manufacture of the steerable bronchoscope, the "up" orientation of the image feed from the bronchoscopic video camera as displayed to the physician or other healthcare professional is aligned with the "up" direction of the steering actuator of the typical steerable bronchoscope. However, it may be desirable to use steerable catheter 600 which may have a smaller outside diameter than the typical steerable bronchoscope. The image feed from bronchoscopic video camera 630 inserted into the working channel of the steerable catheter 600 can be oriented and aligned with the physician's view, as shown and described in U.S. Ser. No. 15/290,822, the entirety of which is incorporated herein by reference. As further described in U.S. Ser. No. 15/290,822, the real-time image feed from the bronchoscopic video camera 630 can be registered to the steerable catheter 600 and displayed by the navigation system 70.

Returning to FIG. 13, navigation system 70 may also display a graphical representation 708 of the respiratory cycle of patient 10 monitored using PTD 20. In certain embodiments, one or more of the images and/or indicia displayed in panels 700, 702, 704, 706, 712 and 716 are displayed as a function of the monitored respiratory state. That is, images in image dataset 400 and/or generated from image dataset 400 are displayed on display 80 that depict the anatomy of patient 10 at the monitored respiratory state. For example, when the patient is at expiration as monitored by PTD 20, images of the anatomy of the patient depicting the anatomy at expiration are displayed. Accordingly, when the patient is at inspiration as monitored by PTD 20, images of the anatomy of patient 10 depicting the anatomy at inspiration are displayed. In other embodiments, one or more of the images displayed in panels 700, 702, 704, 706, 712 and 716 may not be displayed as a function of the monitored respiratory state. That is, images in image dataset 400 and/or generated from image dataset 400 are displayed on display 80 that depict the anatomy of patient 10 at one respiratory state. For example, when the patient is at expiration and inspiration as monitored by PTD 20, images of the anatomy of patient 10 depicting the anatomy at expiration are displayed. In embodiments where images are not displayed according to the monitored respiratory state, an indication 710 of whether the displayed images match the monitored respiratory state may be shown (e.g., "Respiration Matched", "Respiration out of Sync").

Additionally, the display of indicia of the locations of the target tissue and/or indicia of the location of various medical devices may be synchronized or gated with an anatomical function, such as the cardiac or respiratory cycle, of patient 10. That is, in certain embodiments, the indicia are displayed on display 80 as a function of the monitored respiratory state. In certain instances, the cardiac or respiratory cycle of patient 10 may cause the indicia to flutter or jitter within patient 10. In these instances, the indicia will likewise flutter or jitter on the image(s) displayed on display 80.

To eliminate the flutter of the indicia on the displayed image(s), the position and orientation (POSE) of localization elements 610, 660 is acquired at a repetitive point within each cycle of either the cardiac cycle or the respiratory cycle of patient 10. To synchronize the acquisition of position data for localization elements 610, 660, navigation system 70 may use a timing signal (e.g., respiratory phase signal) generated by PTD 20; however one skilled in the art will readily recognize other techniques for deriving a timing signal that correlate to at least one of the cardiac or respiratory cycle or other anatomical cycle of the patient.

As described above, the indicia indicate the location of steerable catheter 600 based on the location of localization element 610 tracked by navigation system 70 as steerable catheter is navigated by the physician or other healthcare profession on and/or within patient 10. Rather than display the indicia on a real-time basis, the display of the indicia may be periodically updated based on the timing signal from PTD 20. In various embodiments, PTD 20 may be connected to navigation system 70. Navigation system 70 may then track localization elements 610, 660 in response to a timing signal received from PTD 20. The position of the indicia may then be updated on display 80. It is readily understood that other techniques for synchronizing the display of an indicia based on the timing signal are within the scope of the present invention, thereby eliminating any flutter or jitter which may appear on the displayed image(s). It is also envisioned that a path (or projected path) of steerable catheter 600, a percutaneous needle, and/or other medical devices may also be illustrated on the displayed image(s). The location of a target in the lung of a patient can be confirmed endobronchially utilizing the devices, systems, and/or methods described herein and as set forth in U.S. Ser. No. 15/290,822, the entirety of which is incorporated herein by reference.

As described above, the processor 52 of the image analysis system 50 and/or the processor 72 of the navigation system 70 utilize image processing and segmentation techniques to identify components in an image, multiple images, or one or more image datasets (e.g., image datasets from different time periods). The segmentations are used during the navigation methods as described above.

Existing methods for segmentation of anatomical treelike structures (e.g., airways, pulmonary vasculature), vary in degree of accuracy and processing time. Spillage occurs when voxels in an image are denoted as part of the segmentation which should not be included. To avoid spillage, many segmentation methods conservatively assess portions of the segmentation where spillage likely occurred, especially several generations deep in the treelike structure, and err on the side of excluding those portions. As a result, many high generation branches on the periphery of the treelike structure fail to be included in the resulting segmentation. However, for many segmentation uses (e.g., in image-guided pulmonary biopsies or other procedures), it can be clinically detrimental to be missing high generation branches on the periphery of the treelike structure (e.g., airway tree) near a target area. The best route to navigate to the target area may include pathways along branches not included in the segmentation. If these high generation branches on the periphery of the treelike structure are not included in the segmentation, navigation systems cannot utilize those branches to plan the optimal path to the target area. Extended segmentation that includes as many high generation branches as possible will provide improved clinical yields and more effective procedures and navigation to target areas.

Referring to FIGS. 14-17, segmentation algorithms and methods are shown and described, including methods for providing segmentation of the lung airways, vasculature and lobes. The segmentation methods according to the present disclosure can be used in conjunction with the image analysis system 50, the navigation system 70, and/or the tracked medical devices (e.g., steerable catheter 600) described above to enhance the segmentation of the image(s) or image dataset(s) (e.g., to increase the accuracy and optimize the navigated pathway 416 to reach target tissue 420, for example). In some embodiments, the image processing methods and algorithms described in FIGS. 14-17 may be utilized to image the lung anatomy for potential diagnostic purposes, wherein the resulting segmentations are displayed to a practitioner on a display 80 separately from navigation system 70.

Figure 14:
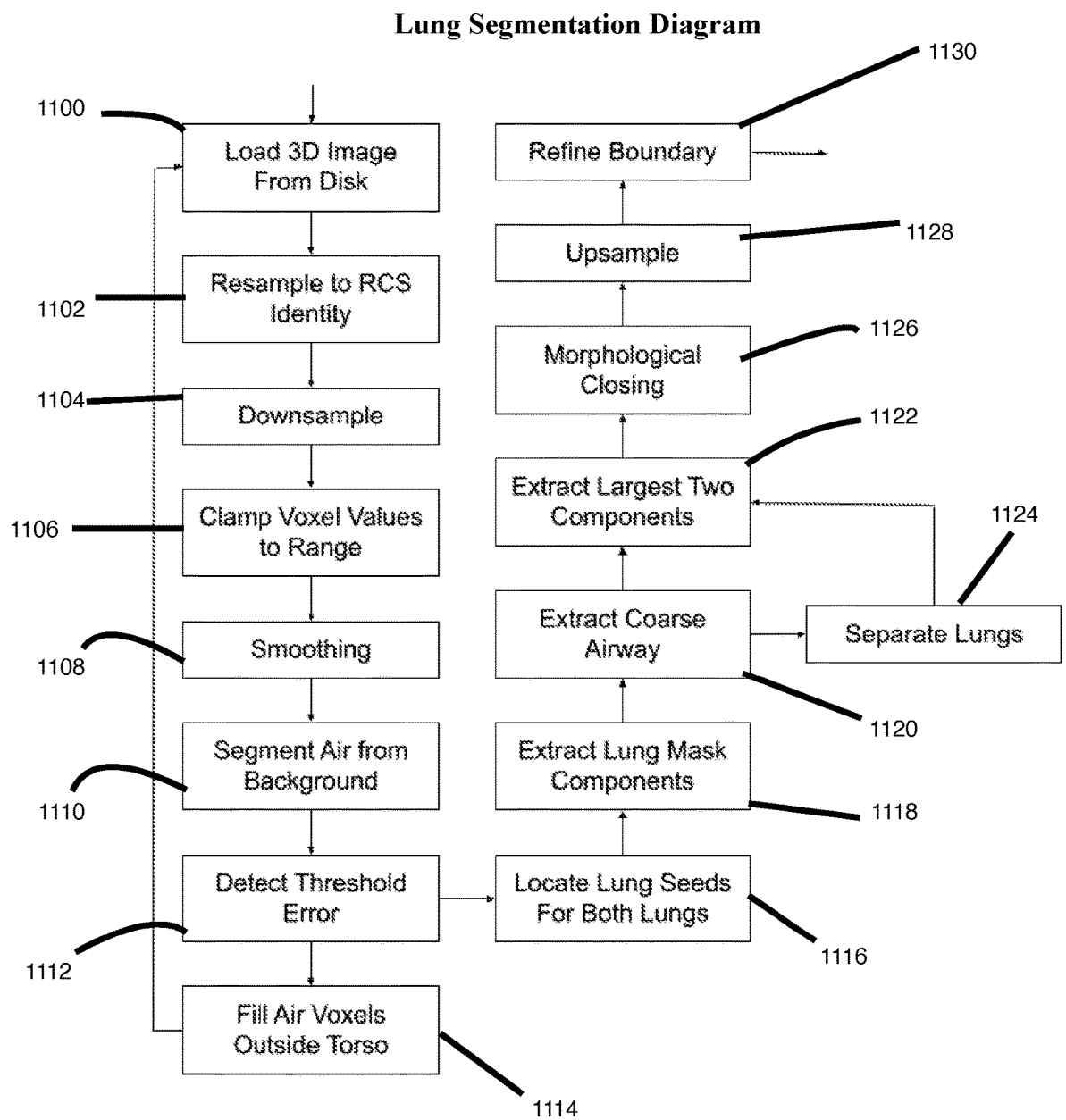
FIG. 14 is a flowchart illustrating a method of anatomical segmentation according to an embodiment.

FIG. 14 illustrates a method sequence for lung segmentation, which includes steps that reduce processing time and overcome failure conditions that can occur with existing segmentation methods in clinical settings. First, at step 1100, 3D image data is received, for example loaded into a memory component 54 from a disk or directly from an imaging device (e.g., imaging device 40 of the system described above). The 3D image data includes specified reference coordinates system (RCS) coordinates. In one embodiment, the 3D image data includes a high resolution CT scan with determined HU values (i.e. an HU image).

At step 1102, the 3D image data is resampled so that the direction of the RCS coordinates correspond to the identity matrix. Step 1102 is optional to simplify subsequent steps of the method, and it is understood that resampling the image may be omitted within the scope of the present invention. For example, other steps in the disclosed method could account for non-identity directions if the image is not resampled to correspond to the identity matrix.

At step 1104, to significantly reduce processing time the 3D image is down-sampled. As an example of the processing time reductions that down sampling may provide, in at least one embodiment, when step 1104 is followed the processing time for the entire lung segmentation process takes about 3-4 seconds, whereas if step 1004 is skipped or left out, the process can take up to 30 seconds or more. Down-sampling can be done here because for the general segmentation of the lungs, finely detailed structures are of less importance to the final result than say for the airway, vasculature or lobe segmentations (described in further detail below), except at the boundary of the lungs, which is accounted for with the final step.

At step 1106 voxel values are clamped to a specific range. In the current implementation HU values on CT data are clamped to the range [−3024 to 20000] because in a clinical setting spurious values outside this range can occur and impact subsequent steps of the algorithm. This step improves the overall robustness of the algorithm across many datasets.

At step 1108 the image is smoothed. In at least one embodiment, the smoothing step 1108 uses discrete Gaussian smoothing to remove small scale image noise.

At step 1110 air is segmented from the image background. In some embodiments, the air segmentation step 1110 may be implemented using the histogram thresholding approach as disclosed by Huang (L. K. Huang and M. J. J. Wang. Image thresholding by minimizing the measures of fuzziness. Pattern recognition, 28(1):41-51, 1995. 1, 2.1, the entire contents of which is incorporated herein by reference) as implemented in the Insight Segmentation and registration Tool kit (ITK) image library. If any error is introduced at step 1110, at step 1112, the error may be detected by evaluating the computed threshold and either 1) by filling air voxels outside the torso in the original image with an HU value higher that air at step 1114 and return to step 1100 at restart the process with the modified image, or 2) continue to step 1116.

Steps 1112 and 1114 can overcome instances routinely seen in a clinical setting where the image contains more or less air voxels than occur in a typical supine CT chest dataset, for instance lateral datasets or poorly cropped scans. In some embodiments, the error may be detected that results from step 1110 by having a final HU threshold outside a determined range. For example, if the condition of the threshold error determined at step 1112 is outside the range of −800 HU to −100 HU, the voxels that are less than −800 HU are thresholded into a binary mask and connected components are extracted from the mask. Components having voxels near any of the eight corners of the image are taken to contain the air outside the torso and all voxels in these components are set to −25. The algorithm is then restarted with this augmented image. In practice, this approach is especially adept at overcoming histogram thresholding failures for lateral datasets.

At step 1116 lung seed voxels are located in the histogram threshold segmentation using anatomical knowledge. With a robust result from step 1112 or 1114, the resulting segmentation mask typically will have two or three large components: one corresponding to the air outside the torso, and one or two corresponding to either the merged lungs via the airway, or two separate lungs. Step 1116 determines which components correspond to the lungs and the airway.

This is accomplished by first morphologically closing and then eroding the histogram thresholded segmentation. This overcomes the lung components of interest not being quite all the way connected (with closing) and also prevents unwanted merging of the lung components with the outside (with erosion). Next, the bounds of the torso are computed by the following steps:

1. Downsample and threshold the image into a binary mask using the HU range [−950 to 16383] (thresholding all voxels that have a little density to the maximum value).
2. For each of the unit vectors (1, 0, 0), (−1, 0, 0), (0, 1, 0), (0, −1, 0), (0, 0, 1) and (0, 0, −1) in RCS coordinates the binary mask is traversed from one side to the other and for each slice, the number of voxels assigned the mask value is computed and the maximum for all slices for each direction is retained.
3. The slices are iterated again for each direction, but this time, when a slice is reached that has a mask value voxel count that is 40% of the maximum for that direction, the iterations for the direction stop. The six planes defined by these stopping slices roughly define a bounding box for the torso.

In at least one embodiment, an estimate for a left lung voxel is generated as that which lies 40% of the way along the torso bounding box's extent in the sagittal direction, and 50% of the way along it's extent coronally and axially. Similarly, an estimate for a right lung voxel is generated as that which lies 60% of the way along the torso bounding box's extent in the sagittal direction, and 50% of the way along it's extent coronally and axially.

At step 1118 mask components are extracted near the lung seed voxels. In at least one example, for each component in the closed and eroded histogram threshold segmentation from step 1116, the 40 nearest voxels and their distances in RCS coordinates to the left and right lung seed estimates from step 1116 are computed and the components are ranked from least to greatest by the average of the 40 distances. In other embodiments, the number of voxels adjacent the components that are selected and distance computed may vary. The voxels that are in the best left or best right (via best fit calculation, proximity analysis, visual comparison or other form of analysis) component and also in the histogram segmentation (before morphological operations) are used to region grow to all other voxels that are 6-connected in the original histogram threshold segmentation.

At step 1120 the course airway is extracted from the result of step 1118. Specifically, as the component(s) containing the lungs have been isolated in step 1118, it is not uncommon for the two lungs to be merged via the airway. For these cases, the voxels corresponding to the first few generations of the airway are removed to ensure the left and right lungs are separated. This is accomplished by locating a trachea seed voxel as follows:

1. Downsample the binary image resulting from step 9 to improve processing time, and also because finer details of the mask are unimportant for subsequent steps.
2. Extract slices of the image in the decreasing axial direction (top to bottom) and for each slice extract the contours for that slice (in this case using ITK)
3. Collect all contours that lie fully between 25% and 75% of the way along the image's sagittal extent, and that have an area between 100 and 1000 mm$^2$, and compute their centroids. These values are determined empirically and are roughly dictated by the fact the trachea typically has an inner radius of about 10 mm and thus an area of roughly 300 mm². The wide range accounts for anatomical variations.

4. If contours are generated on a certain number of successive slices that are compatible in the sense of having centroids that are within a certain distance of each other and areas that are within a certain tolerance of each other, the trachea point is taken to be the centroid for the middle of these successive slices.

If no trachea seed point is found, then the lungs are already separated into two components. If one is found, a spillage constrained region grower is used that grows to mask voxels 6-connected to the trachea seed point voxel that stops growing if the front for an iteration reaches a certain size or if beyond a certain number of iterations the front grows beyond a certain amount as a percentage of the previous iteration's front size.

If the result from step 1120 contains two components, the segmentation process continues to step 1122. If not, the single component is separated into two components at step 1124. For cases where the lungs are still connected after coarse airway extraction, typically due to a very thin pleura separating the lungs, additional steps must be taken to have a separated left and right lung. The lung separation algorithm is performed by extracting the middle two thirds of the unseparated mask with respect to the sagittal axis, eroding the cropped mask with varying structuring radii and searching the eroded region for bright plate like structures using a multiscale Hessian and a plate response function such as has been described in: Luca Antiga (2007), Generalizing vesselness with respect to dimensionality and shape, The Insight Journal, vol. 3, pp. 1-14; the entire contents of which are incorporated herein by reference, and removing these voxels from the mask. The width of the search image is increased, if necessary, until a separation occurs.

The two largest components from step 1120 or step 1124 are extracted at step 1122. Then, at step 1126, each component is morphologically closed independently. To ensure the two components (lungs) have not merged after closing, any voxels in one lung that are 6-connected to those in the other lung are removed. Removal will typically only apply to a small number of voxels. In at least one embodiment between 1-5 voxels will be removed.

At step 1128, if it is necessary to improve the visualization of the image from step 1126 the image is upsampled to the original image dimensions.

In the final step 1130, the boundary of the lungs is refined by using the upsampled mask and the original image. To do this each lung is extracted from the upsampled lung mask and for voxels on the boundary, determined via a distance map, sets the voxel to the mask value in the mask if the corresponding voxel in the image is less than or equal to −500, or else sets it to zero. As a final beautification step for visualization, an iterative hole filter is applied which sets each voxel in the mask to the mask value if more than half of its 26-connected neighbors are set to the mask value, and repeats this process for a number of iterations. To ensure the two lungs have not merged after this step, any voxels in one lung that are 6-connected to those in the other lung are removed. Typically if this has occurred, it is only for a small number of voxels, such as between 1-200 voxels.

Figure 15:
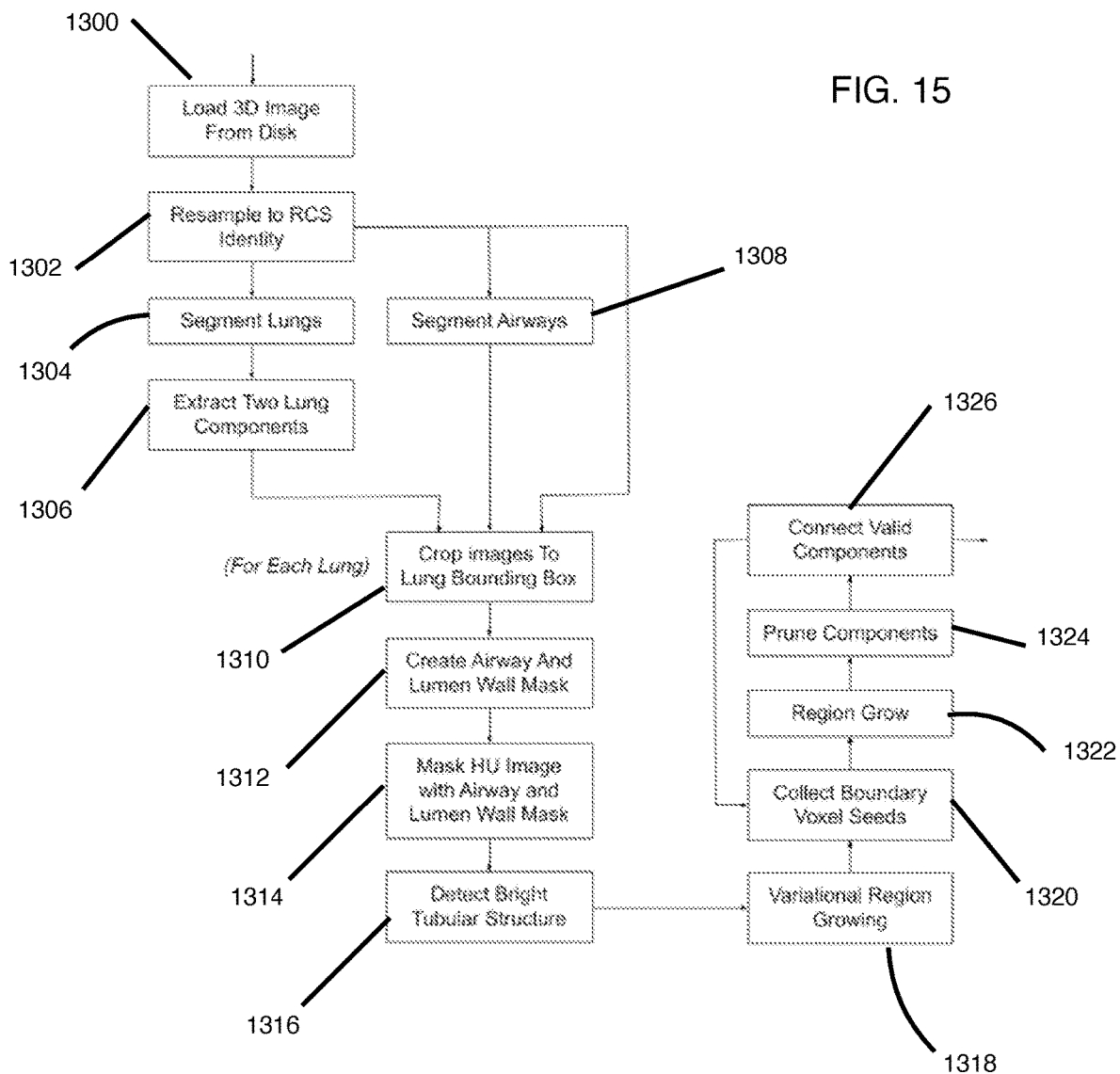
FIG. 15 is a flowchart illustrating a method of lung vasculature segmentation according to an embodiment.

We turn now to a segmentation algorithm for the segmentation of the lung vasculature, of which an embodiment of the segmentation process is presented in the flow-chart of FIG. 15.

As with the lung segmentation process shown in FIG. 14, the vasculature segmentation process begins with receipt of 3D image data at step 1300. Image data is, for example loaded into a memory component 54 from a disk or directly from an imaging device (e.g., imaging device 40 of the system described above. Image data may be provided by various imaging modalities such as from a CT, MRI or other types of scans, with best results being achieved with scans of higher resolution.

At step 1302 the image is re-sampled so that the direction of the image corresponds to the identity matrix. Step 1302 is optional to simplify subsequent steps of the method, and it is understood that resampling the image may be omitted within the scope of the present invention. For example, other steps in the disclosed method could account for non-identity directions if the image is not resampled to correspond to the identity matrix.

At step 1304 a segmentation of the lungs is undertaken. In at least some embodiments, the lung segmentation is obtained by following the process shown in FIG. 14 and described above. In some embodiments, alternative algorithms and/or processing methods may be utilized to obtain the lung segmentation. Though it is not strictly necessary to provide the lung segmentation as part of the vasculature segmentation process, failing to do so will greatly increase processing time of the vasculature segmentation process and reduce the robustness of the results.

Since the lung segmentation process guarantees separation of the lungs into the left and right lungs, a connected components filter is applied at step 1306. In accordance with the lung segmentation step 1304 this step is also not strictly necessary, but if omitted the processing time for the remaining steps is increased.

At step 1308, segmentation of the lung airway is performed. In some embodiments, this step is performed using an algorithm that first finds a trachea seed point in the manner described above (see step 1200 of the lung segmentation algorithm of FIG. 14). The algorithm then performs threshold based region growing for increasingly less constrained HU ranges until a range of values results in a segmentation with at least a specified volume. The HU range that resulted in the greatest increase in volume from its predecessor is then taken to be the range which resulted in leakage, and the predecessor range is used to obtain an initial segmentation of the larger bronchi. The region growing result is then checked for leaks by checking for structures which are connected to the trachea through paths that are much thinner than their local size. These components are removed and a post-processing step is applied to fill holes and ensure the result is 6-connected. This is the coarse airway segmentation. The distance map of this result is then subtracted from the original CT image and the same region growing step as described above is applied both to the distance map incorporated image and the distance map incorporated image with Gaussian smoothing applied. This yields conservative and aggressive airway segmentations.

The final result is obtained by merging the coarse segmentation with the intersection of the conservative and aggressive segmentations and then merging components that remain in either the conservative or aggressive airway masks that that are likely to be part of the final mask based on analysis of the centerlines of the components.

The subsequent steps 1310-1316 are run on each lung image. First, at step 1310, the original image and the airway mask are cropped to the bounding box of the lung airway mask.

At step 1312, within each lung, an airway and lumen wall mask is produced. The thickness of the lumen walls generally decreases as the generation of the airway branch increases, so to ensure the mask accurately reflects the lumen wall thickness for all the airway generations in the airway segmentation, the airway is morphologically opened and the dilated with multiple structuring radii, where a higher structuring radius captures lower generation airway branches. The results of the morphological operations at varying radii are then merged into one mask to capture the airways and lumen walls for several branch generations.

At step 1314, the cropped image of step 1308 is masked with the airway and lumen wall mask of step 1312.

At step 1316, voxels which correspond to bright tubular structures in the cropped and masked image are detected and extracted. Voxels within bright tubular structures are extracted from the image based on a multiscale Hessian analysis of the image. The eigenvalues and eigenvectors of the Hessian, computed discretely at different scales, are computed for each pixel and this information is used to assign each pixel a metric value based on how tubular it is. The function of the eigenvalues that computes the metric follows the function such as is described in the already cited to publication: Luca Antiga (2007), Generalizing vesselness with respect to dimensionality and shape, The Insight Journal, vol. 3, pp. 1-14. Once this vesselness score is assigned to each voxel, a thresholder is applied that thresholds all voxels that achieve above a certain score into a binary mask. Connected components are then extracted and components that are less than 3 voxels in size are discarded. The voxel in each component with the maximum vessel score is then found and these voxels are ordered by:

$$\text{sgn}(H)\ln(\sqrt{|H|})*V$$

Where H is the Hounsfield density at the voxel and V is the vessel response score. This allows voxels with a lower HU value than is typically seen in pulmonary vasculature to be included butto have a lower priority in the next step of the algorithm.

Using the voxels found in step 1316, region growing is performed at step 1318. A variational region growing algorithm is known from: M. Orkisz, M. Hernández Hoyos, V. Pérez Romanello, C. Pérez Romanello, J. C. Prieto, C. Revol-Muller, (2014). Segmentation of the pulmonary vascular trees in 3D CT images using variational region-growing. IRBM, Volume 35, Issue 1, Pages 11-19; the entire contents of which is incorporated herein by reference. Step 1318 follows such a variational region growing algorithm.

At step 1318, the algorithm tracks an "inside" binary image consisting of the current segmentation and an "outside" binary image consisting of its complement. The "inside" image is initialized with the voxels resulting from step 1316. The mean vesselness response and the mean HU value of voxels in the inside image and the outside image are computed based on this initialization, where the vessel and HU values are both normalized to be in the range [0 1]. Then, for each voxel in the result from step 1316, iterated in an order based on score as described in step 1316, 6-connected region growing is performed where inclusion in the "inside" image is determined by the condition:

$$w_v(|v-v_{in\_mean}|-|v-v_{out\_mean}|)+w_h(|h-h_{in\_mean}|-|h-h_{out\_mean}|)<0$$

Where $w_v$ and $w_h$ are optional importance weights that in the current implementation are 2 and 1 respectively, v is the normalized vessel response value for the candidate voxel, h is the normalized Hounsfield value for the voxel and $v_{in\_mean}$ and $h_{in\_mean}$ are the mean vessel and Hounsfield values for the current inside image and $v_{out\_mean}$ and $h_{out\_mean}$ are the mean vessel and Hounsfield values for the current outside image. The means are recomputed as voxels are added to the inside image.

This condition will be satisfied when the voxel is more similar in terms of vessel response and Hounsfield value to what's already been segmented than not. Initializing the inside image with voxels that have a high probability of being vessels as described in step 1316, and also region growing in the order described ensures the inside image quickly becomes characterized by voxels with the properties that are more likely to be vasculature.

To further reduce the potential for blowout, where the vessel segmentation spills into non-vessel structures like nodules or lobe fissures, the region grower proceeds as follows for each voxel in the list from step 1316:

1. If the voxel is already in the segmentation from a previous region grow, do nothing. Else, test all of the 6-connected neighbors of the voxel for inclusion. The list of included voxels is made the first element in an initial list of fronts.
2. If the list of fronts is not empty test all of the 6-connected neighbors of every voxel in the first front of the list for inclusion and create a list of included voxels.
3. Convert this list to a list of points in image space corresponding to the voxels and check for instances of the front splitting into two clusters of voxels that are separated by a geometric distance in RCS coordinates.
4. If a split did not occur, retain the list of valid voxels as the first front in the list. If the front did split create a new front for each cluster and put it at the beginning of the list and for each store the size of the front that split on the iteration before it split. This value will be used to limit the amount the new split fronts will be allowed to grow.
5. Go to step 2.

Since the seed voxels will typically be at the center of vessels this region growing algorithm will, by the constraint placed on front growth in addition to the variational region growing condition, grow to all child vessels of the seed and not spread to larger objects like nodules, lobe fissures or parent vessels. If the vessel response step picks up a robust set of seed points this step has a good chance of growing a robust tree with a low number of false positives.

At step 1320, voxels are collected on the boundary of the result from step 1318 that satisfy geometric and imaging criteria. For this step an image is computed by taking the cropped HU image (derived from the original 3D image data) from step 1312 and setting voxels that are in the results from step 1318 (the current segmentation) to a very low HU value (−900 in the current implementation). Then, the distance map of the result from step 1318 is computed and any voxels that touch the boundary of the mask and are within a prescribed Hounsfield range in the augmented HU image are collected as seed points for the next step.

At step 1322, a 6-connected region grower uses the seeds collected in step 1320 to grow to neighboring voxels in a prescribed range of HU units within the augmented HU image.

At step 1324, the new connected components resulting from the region growing of step 1322 are analyzed and then depending on if they meet geometric and imaging criteria such as in the manner described in step 1312, they will be discarded or, at step 1326, merged with the starting segmentation.

If desired to provide a fuller segmentation steps 1320-1324 may be iteratively repeated with changes to the HU ranges and pruning criteria on successive iterations.

Figure 16:
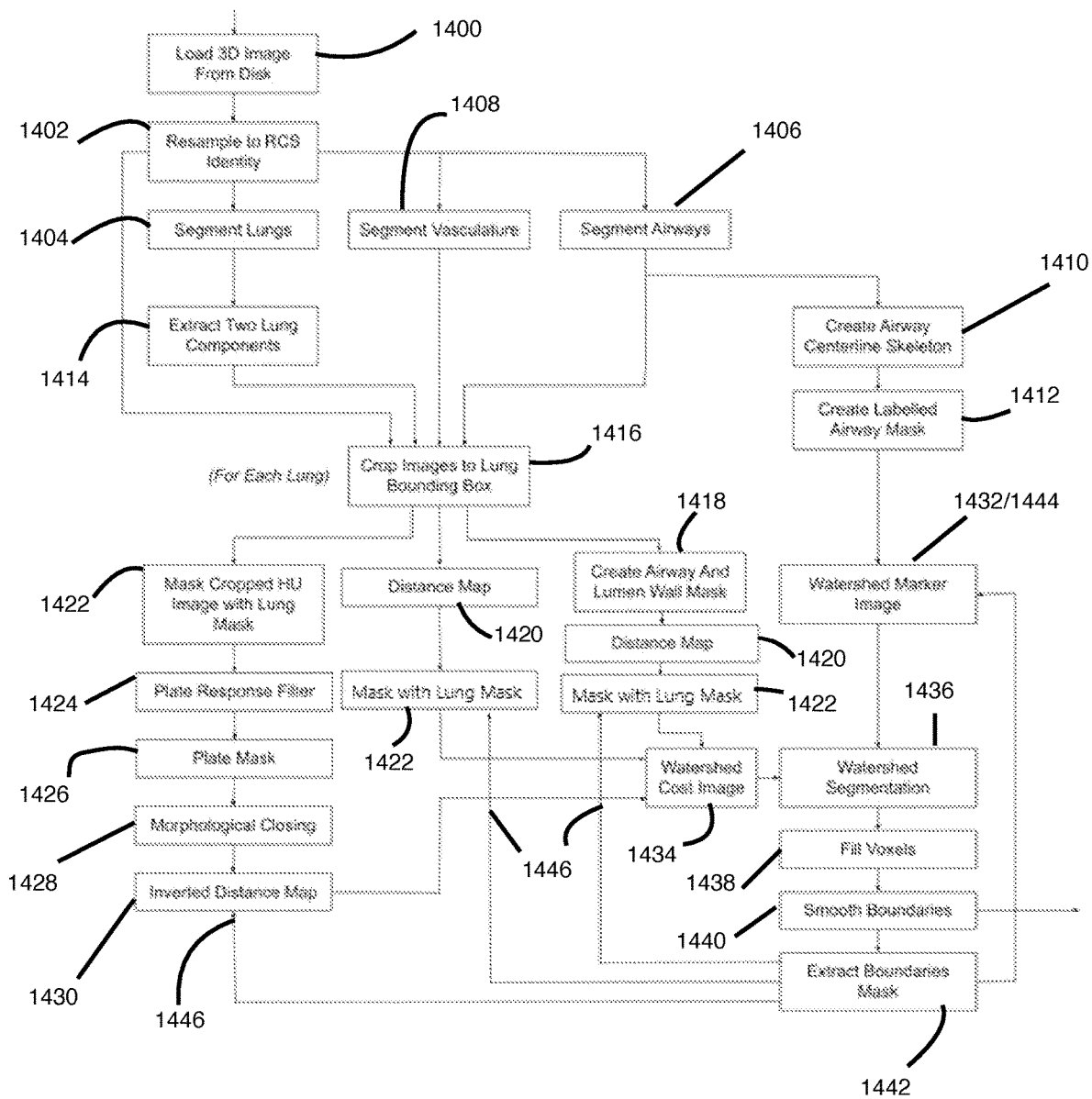
FIG. 16 is a flowchart illustrating a method of lung lobe segmentation according to an embodiment.

Turning now to a lung lobe segmentation algorithm and process, and embodiment of this process is illustrated in FIG. 16.

As with the other processes, the first step 1400 is to load a 3D image with specified RCS coordinates into the memory component 54. The image may be obtained from an imaging modality such as CT, MRI, etc. scan, though high resolution CT scan images are preferred.

As in other processes described herein, the next step 1402, is the optional image resampling step, wherein the image is re-sampled so that the direction of the image corresponds to the identity matrix. This step simplifies subsequent steps but is not required.

At step 1404, lung segmentation is performed in the same manner as previously described above and shown in FIG. 14.

At step 1406, a segmentation of the lung airway is performed, such as in the same manner as described above and shown at step 1308 of FIG. 15. In at least one embodiment airway segmentation is performed using an algorithm that first finds a trachea seed point in a manner similar to that described for the lung segmentation algorithm detailed above. It then performs threshold based region growing for increasingly less constrained HU ranges until a range of values results in a segmentation with at least a specified volume. The HU range that resulted in the greatest increase in volume from its predecessor is then taken to be the range which resulted in leakage, and the predecessor range is used to obtain an initial segmentation of the larger bronchi. The region growing result is then checked for leaks by checking for structures which are connected to the trachea through paths that are much thinner than their local size. These components are removed and a post-processing step is applied to fill holes and ensure the result is 6-connected. This is the coarse airway segmentation.

The distance map of this result is then subtracted from the original CT image and the same region growing step as described above is applied both to the distance map incorporated image and the distance map incorporated image with Gaussian smoothing applied. This yields conservative and aggressive airway segmentations.

The final result is obtained by merging the coarse segmentation with the intersection of the conservative and aggressive segmentations and then merging components that remain in either the conservative or aggressive airway masks that that are likely to be part of the final mask based on analysis of the centerlines of the components.

At step, 1408 lung vasculature segmentation is performed such as in the manner described above.

Steps 1406 and 1408 are both optional, but their omission will reduce the robustness of the final lob segmentation, especially for datasets with incomplete fissures.

After the initial segmentation is extracted, at step 1410 a centerline skeleton is created from the initial segmentation. The centerline skeleton is topologically treelike (i.e., n bifurcation points with n−1 centerlines connecting the bifurcation points). The centerline skeleton may include a number of "branches" (or edges) corresponding to an ordered list of 3D points (center points) that comprise a simple path with no loops or bifurcations. For example, a branch or edge may include several center points that are connected to form the edge (see FIG. 18 and the discussion below for additional details).

At step 1412, each voxel in the initial segmentation is assigned to an edge in the centerline skeleton (i.e., mask labeling each voxel by the "tree" edges). In this mask labeling step, each voxel is assigned to an edge such that the Euclidean distance between the corresponding geometric point of the voxel and the minimum distance to the centerline of the edge is minimized. Each edge will correspond to a generally cylindrical and convex mask containing the center points of the edge.

Since the lung segmentation process guarantees separation of the lungs into the left and right lungs, a connected components filter (i.e. a lung mask a binary mask for an individual lung) is applied at step 1414.

At step 1416, the original image, the airway mask, and the vasculature mask are cropped to the bounding box of each individual lung.

At step 1418, an airway and lumen wall mask within the lung is created. The approach used here follows that which was described previously by Krissian K, Malandain G, Ayache N, Vaillant R, Trousset Y (2000). Model based detection of tubular structures in 3D images. Comp Vis Image Understand. 80:130-171; the entire contents of which is incorporated herein by reference. The lumen wall thickness generally decreases as the generation of the airway branch increases, so to ensure the mask accurately reflects the lumen wall thickness for all the airway generations in the airway segmentation, the airway is morphologically opened and the dilated with multiple structuring radii, where a higher structuring radius captures lower generation airway branches. The results of the morphological operations at varying radii are then merged into one mask to capture the airways and lumen walls for several branch generations. Since the airway segmentation does not typically include the lumen walls, and the lumen walls should not be near the lobar boundaries, this step can slightly improve the overall robustness of the results, but may be left out of the process in some embodiments.

At step 1420, distance maps are calculated for the airway and lumen wall mask and cropped vasculature mask provided in step 1416. This step computes the Euclidian distance map using a CUDA implementation of the algorithm such as in the manner described in Meijster A., Roerdink J. B. T. M., Hesselink W. H. (2002) A General Algorithm for Computing Distance Transforms in Linear Time. In: Goutsias J., Vincent L., Bloomberg D. S. (eds) Mathematical Morphology and its Applications to Image and Signal Processing, Computational Imaging and Vision, vol 1; the entire contents of which are incorporated herein by reference.

At step 1422, the cropped HU image and the distance maps of step 1420 are masked with the lung mask. At this step there is no information that informs the lobe segmentation outside of the lung volume. Thus, this step can improve the robustness of subsequent steps, but in some embodiments may be omitted from the process.

At step 1424, a bright plate response image is computed using the cropped masked HU image and the cropped vasculature of step 1422. Voxels that have a good chance of being bright plate like structures are extracted using a multiscale Hessian and a plate response function like that described in: Bianca Lassen, Eva M van Rikxoort, Michael Schmidt, Sjoerd Kerkstra and Bram van Ginneken and Jan-Martin Kuhnigk (2013), Automatic segmentation of the pulmonary lobes from chest CT scans based on fissures, vessels, and bronchi. IEEE Trans Med Imaging. vol. 32, 2; the entire contents of which are incorporated herein by reference. Also from this, the eigenvector corresponding to the eigenvalue with the greatest modulus is retained for each voxel as this corresponds to the direction of greatest curvature. For plate-like voxels this is the normal to the plate's surface. Also, similarly, the number of false positives in the result is reduced by:

1. Thresholding the voxels that have a plate response score of 0.1 or greater and an HU value less than or equal to the mean of the HU values in the vasculature mask into a binary mask.
2. Extracting connected components from the mask where voxels in a component are connected if they are 6-connected and their plate surface normal vectors are within a certain angle of each other. In the case of the current implementation this is a dot product of 0.99 or greater.
3. Components are discarded that have a volume of less than 400 mL. This threshold was determined empirically to leave very few false positives in the final set of voxels.
4. Finally the plate response image is masked with a mask containing all the voxels in the components present from step 3.

At step 1426, a plate mask is created. This step simply thresholds non-zero voxels from plate mask into a binary mask.

At step 1428, the system morphologically closes the plate mask by closing gaps in the plate mask to provide better results in the next step.

At step 1430, an inverted plate map of the closed plate mask is calculated by:

1. The distance map is computed on the morphologically closed plate mask.
2. Values outside the lung are set to zero
3. Values inside the closed plate mask are set to zero
4. The maximum value of the image resulting from step 3 is computed
5. All values in the image resulting from step 3 are subtracted from the value computed in step 4.

At step 1432, a watershed marker image is created, using the extracted lung component, the centerline skeletonization of the airway mask and the labeled airway mask. To create the watershed marker image as one input to the watershed segmentation algorithm, first, all the voxels outside the lung are assigned a marker label of 255. Next, depending on if the left or right lung is being processed, a segment in the airway tree belonging to each lobe is estimated. This is accomplished by collecting all terminal segments (segments with no children) from the tree and then for those that are within the left lung determining:

1. The segment which has a distal point with the greatest axial RCS coordinate. This corresponds to a segment in the left superior lobe.
2. The segment which has a distal point with the least axial RCS coordinate. This corresponds to a segment in the left inferior lobe.

For those terminal segments within the right lung it is determined:

1. The segment which is farthest along a plane with normal vector $$\left(0, \frac{1}{\sqrt{2}}, -\frac{1}{\sqrt{2}}\right)$$

as it passes through the image. This corresponds to a segment in the right inferior lobe.

2. The segment which has a distal point with the greatest axial RCS coordinate. This corresponds to a segment in the right superior lobe.

With segments in the right inferior and right superior lobe extracted, subtrees containing these segments are extracted and the terminal segments in the right lung are processed again. This time the terminal segment in the right lung that has a distal point with the least coronal coordinate is found. This corresponds to a segment in the right middle lobe.

With airway segments in each lobe identified, a subtree is identified for each lobe, an empty mask image is created with the same geometric properties as the marker image and the following steps are performed:

1. Voxels corresponding to distal points in segments are set to the mask value in the mask image.
2. Rays of voxels are filled starting from the voxels identified in step 1 and extending to either to the lung boundary or extending to a certain distance according to the following strategies:

Along rays parallel to the expected direction for the lobe. These are unit vectors that are determined experimentally to correspond to the average of fissure normals extending into the lobe projected onto the coronal-axial plane for all fissures bounding the lobe of interest. For the left lung this corresponds to the vector (0, −3, 2) normalized for the left inferior lobe and the vector (0, 3, −2) normalized for the left superior lobe. For the right lung this corresponds to the vectors (0, 1, −1), (0, −5, −2) and (0, −2, 3), all normalized for the right inferior, right middle and right superior lobes respectively.

Along rays given by the direction of the segments. To ensure this doesn't result in rays that cross interlobar boundaries, this strategy is only employed for segments for which the direction projected onto the coronal-axial plane is within a lobe specific angle to the expected direction for the lobe. For the current implementation the angles are $$\frac{\pi}{3}, \frac{\pi}{3}, \frac{\pi}{6}, \frac{\pi}{12} \text{ and } \frac{\pi}{3}$$

for the left interior, left superior, right inferior, right middle and right superior lobes respectively.

Along rays given by the direction of the segments projected onto the coronal-axial plane. To ensure this doesn't result in rays that cross interlobar boundaries the same constraints as above are applied.

Along rays that lie on the surface of cones whose apexes are at the distal points of the segments and that extend in the expected direction for the lobe. The angle of the cone is determined by the lobe and how far into the lobe along the expected direction the segment is. For segments that are farther into the lobe along the expected direction it is safe to use a wider cone angle without fear of the rays crossing an interlobar boundary. For the current implementation the angle ranges for the cones are $$\left[\frac{\pi}{4}, \frac{\pi}{3}\right], \left[\frac{\pi}{4}, \frac{\pi}{3}\right], \left[\frac{\pi}{9}, \frac{5\pi}{18}\right], \left[\frac{\pi}{18}, \frac{\pi}{9}\right] \text{ and } \left[\frac{\pi}{6}, \frac{\pi}{3}\right]$$

for the left inferior, left superior, right inferior, right middle and right superior lobes respectively.

After all the applicable voxel rays are populated the mask image is morphologically closed and dilated and then copied into the marker image with the mask value being translated to a unique marker number for the lobe.

At step 1434, a watershed cost image is constructed from the lung segmentation mask of step 1414, the cropped masked HU image of step 1422, the vasculature and airway distance maps of step 1422 and the inverted plate distance map of step 1430. This is accomplished by first creating an augmented image by thresholding the masked HU image so that voxel values in a range of interest (in one embodiment [−880 50]) have a fixed number added to them that is at least the lower bound in the range to ensure the values are non-negative and values outside the range are set to zero. The value of each voxel i in the cost image is then given by:

$$c_i = \begin{cases} h_i + w_a \dfrac{a_i}{a_{max}} + w_v \dfrac{v_i}{v_{max}} + w_p \dfrac{p_i}{p_{max}} & i \in L \\ w_a + w_v + w_p + h_{max} + 1000 & i \notin L \end{cases}$$

Where $h_i$ is the value of the voxel in the augmented HU image, $a_i$ is the airway distance map value at the voxel, $v_i$ is the vasculature distance map value at the voxel, $p_i$ is the inverted plate distance map value at the voxel, $a_{max}$, $v_{max}$, $p_{max}$, and $h_{max}$ are the maximum values in the airway, vasculature, inverted plate distance map and augmented HU image respectively, $w_a$, $w_v$, and $w_p$ are weights that are given to influence the importance of each term and L is the set of voxels in the lung mask.

At step 1436, a watershed segmentation is performed, using the watershed cost and watershed marker images. In at least one embodiment, the step is performed using a morphological watershed from marker images filter. With this algorithm the sets of voxels corresponding to each unique label in the marker image are treated as distinct regions that grow to voxels of increasing intensity in the watershed cost image that lie on their boundaries. This region growth continues until either all of the regions meet and completely partition the image or each region is completely surrounded by a set of high intensity values in the watershed cost image, also known as watershed lines.

At step, 1438, voxels that are present in the extracted lung component but not in any of the lung lobe masks after step 1436 are assigned. So as to ensure all voxels in the lung mask are assigned to one of the lobes, the distance map of each lobe is computed, and each voxel that is in the lung mask but not in any of the lobes, is assigned to the nearest lobe.

At step 1440, the boundaries between each pair of lobes in the extracted lung component are smoothed. At this point the segmented lobar boundaries are typically close to the true lobar boundaries, but can have a level of curvature that is not plausible or acceptable from a clinical standpoint, especially for sections of the boundary that lie on visible fissures. Given that lobar boundaries in reality have a low amount of curvature, in some embodiments it may be beneficial to the process to smooth the results. Many approaches may be employed, but in at least one embodiments, the following alternative methods may be used:

1. Extracting each lobe in turn as a mask, morphologically closing it and then copying it back into the segmentation within the lung mask and with the lobe marker value.
2. Extracting each lobe in turn as a mask, applying an iterative hole filling filter to it which consists of counting the number of voxels in a box of a given size in voxels centered at each voxel that are the mask value, and if the voxel value is zero, assigning the voxel the mask value if the number of mask value voxels in the box is above a certain threshold, repeating this for each voxel for a number of iterations and then copying the result back into the segmentation with the lobe marker value.
3. Extracting each lobe in turn as a mask, morphologically opening it and then copying it back into the segmentation with the lobe marker value. Since the opening is typically not larger than the original mask, step 20 is performed after this smoothing approach.
4. Extracting a small region around each boundary (each corresponding to a pair of lobes) using distance maps and then:
    converting it to a mesh using an approach such as marching cubes
    decimating the mesh
    smoothing the mesh using Laplacian smoothing or any mesh curvature reduction or fairing technique
    creating a bsp tree from the mesh to allow for fast intersections
    for each voxel in the watershed segmentation in a slightly larger region around each lobar boundary, computing the intersection with the smoothed boundary mesh along a ray extending in a direction corresponding to the lobe's expected normal or it's reciprocal, depending on which lobe voxel is being tested for recategorization. For instance, for the lobe boundary between the right middle and right superior lobes, the expected lobe normal should be roughly (0, 0, 1) or (0, 0, −1) depending on if the normal is extending into the superior or middle lobe respectively. So if a candidate voxel is currently assigned the middle lobe marker value, the intersection test would use the (0, 0, 1) expected normal and if the number of intersections is positive and divisible by 2, the voxel is still on the correct side of the boundary and does not need recategorization. However, if the number of intersections is zero, then that voxel is now on the other side of the lobar boundary and needs to be recategorized as a right superior lobe voxel. Voxels inside the smoothed boundary are set to zero and then step 20 is performed to fill these unassigned voxels.

At step 1442, a boundary region is extracted around the boundary between each pair of lobes in the lung and aggregated into a mask representing voxels within a certain distance of lobar boundaries. In this step each pair of lobes is extracted and distance maps are used to extract each boundary mask. Finally the union of the boundary masks is constructed.

At step 1444, a new marker image is created using the current watershed segmentation that is outside the boundaries mask combined with the original marker image. In at least one embodiment, the watershed segmentation with the boundaries mask unfilled is combined with the original markers image.

At step 1446, the masked cropped HU image, the airway and lumen wall distance map, the vasculature distance map or the inverted plate distance map are masked, with potentially varying parameters for voxels inside the boundaries mask, with the boundaries mask 1434 using the modified inputs.

Now that a far more precise marker image has been constructed, the images informing the cost image of step 1434 can be masked with the boundaries mask to exclude regions that have already been determined to belong to the correct lobes with a high degree of certainty and prevent their influence on the cost image and subsequent watershed segmentations.

This iterative approach allows for flexibility in choosing such parameters as the watershed cost weights described in step 1434 (perhaps even setting a subset of them to zero to eliminate the influence of a specific image), or the width of the boundary masks used to construct the boundaries mask, or smoothing parameters like morphological structuring radii, iterative hole fill box voxel length or mesh smoothing parameters differently for successive iterations.

The step is not required but it can improve the final result from a clinical, accuracy and visualization standpoint.

Figure 18:
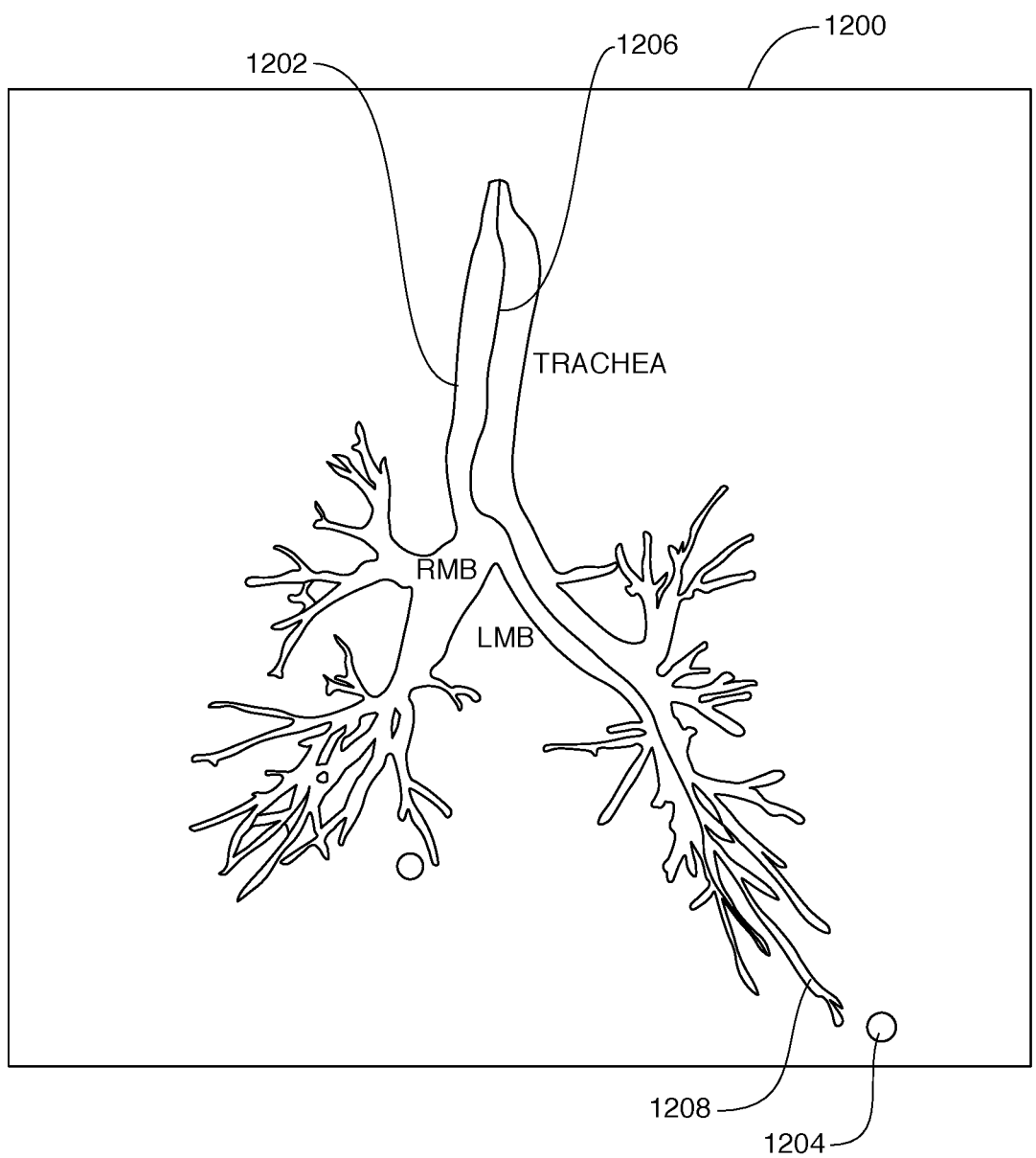
FIG. 18 is an image for navigating to a target, illustrating an initial path to a target based on an initial segmentation.
Figure 19:
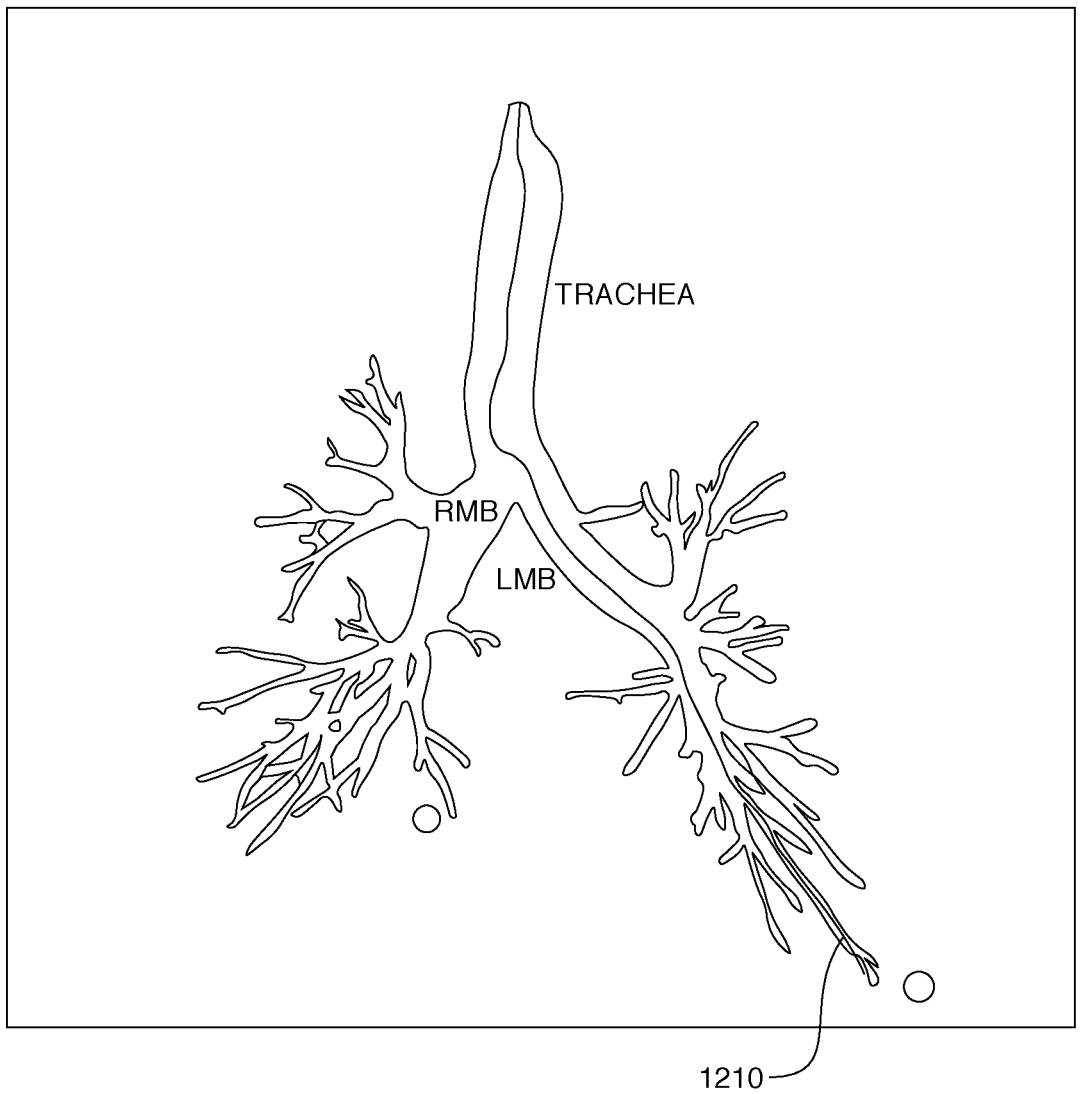
FIG. 19 is an image for navigating to a target, illustrating a revised path to a target based on an extended segmentation.

The lobe segmentation algorithm presented above, and illustrated in FIG. 18, relies heavily on an airway and vasculature segmentation, so if the results of those two algorithms are not robust it will have a significant impact on the quality of the lobe segmentation. Unfortunately, expiration datasets tend to yield much lower quality airway and vasculature segmentations. The lung segmentation itself however, is typically of just as high a quality as for the corresponding inspiration CT scan, since it relies on fairly coarse details in the scan.

Additionally, it is possible to compute a non-linear deformation that maps an inspiration CT to its corresponding expiration CT. The result is a vector field that takes each voxel from the inspiration CT into a point by which a voxel in the expiration CT scan can be obtained. The deformation typically lacks the accuracy to map visible fissures accurately between the two scans, but for the vasculature and airway the mapping does not need to be extremely precise to give much better inputs to the watershed marker and cost image creation than the corresponding expiration segmentations. Also, the fissures can still be detected, although with diminished accuracy due to the usually higher density of parenchyma in expiration scans, with the plate response filter described in the previous section on the expiration CT.

Figure 17:
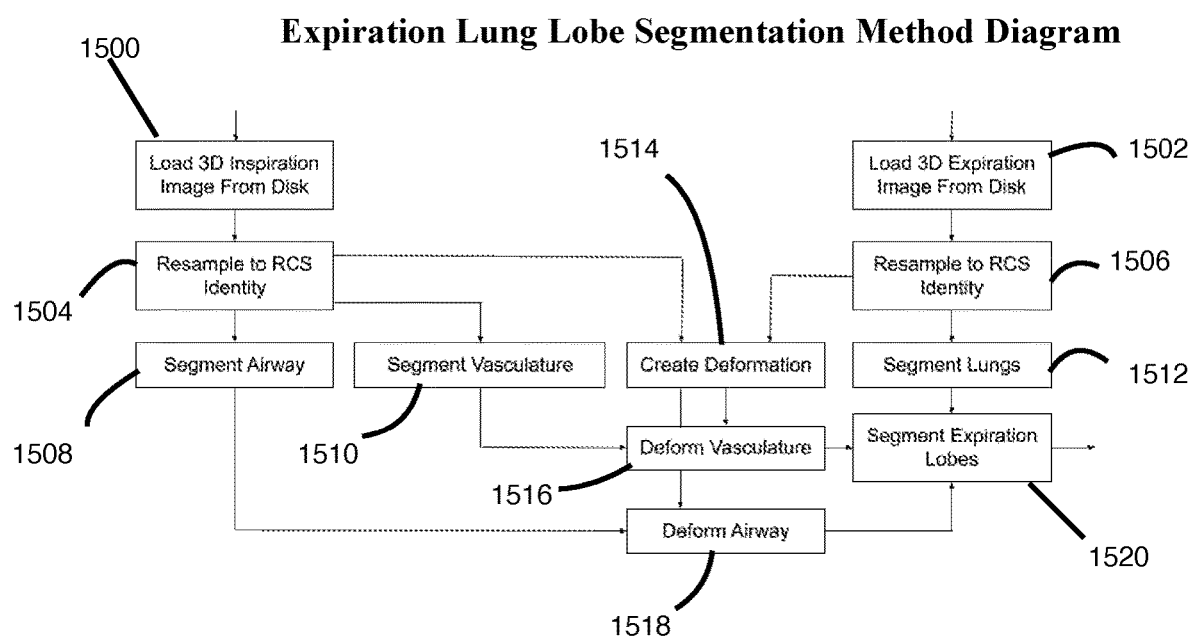
FIG. 17 is a flowchart illustrating a method of expiration lung lobe segmentation according to an embodiment.

This means it is possible to map robust airway and vasculature segmentations obtained from the inspiration scan into the expiration scan. These objects can then be used along with the expiration lung segmentation to perform lobe segmentation on the expiration dataset with a higher level of accuracy than using only segmentation on the expiration data or non-linearly mapping the lobes or fissures directly. Such a lobe segmentation and the process for achieving it is shown in FIG. 17.

At step 1500 a 3D inspiration image with specified RCS coordinates is loaded into the memory component 54, and at step 1502, a 3D expiration image with specified RCS coordinates is loaded into the memory component 54. The images may be obtained from an imaging modality such as CT, MRI, etc. scan, though high resolution CT scan images are preferred.

At steps 1504 and 1506, the images are respectively re-sampled to so that the direction of the image corresponds to the identity matrix.

At step 1508, the lung airways are segmented from the resampled inspiration images in the manner described above.

At step 1510, the lung vasculature is segmented from the resampled inspiration images in the manner described above.

At step 1512, the lungs are segmented from the resampled expiration image in the manner previously described.

At step 1514, the deformation is computed from the inspiration image to the corresponding expiration image.

At step 1516 the vasculature is deformed, and at step 1518 the airway is deformed, these deformations are applied to the lung segmentations, to perform the expiration lobe segmentation at step 1520.

Clinical Applications

Fissure Integrity Analysis

The lobe segmentation process described above forms a complete partition of each lung into either 2 or 3 lobes, even for datasets where the fissure is not detected by the plate response filter or by Hounsfield values. A possible fissure integrity metric can therefore be derived as follows:

1. Use the distance maps for a pair of lobes to extract a mask representing the lobar boundary.
2. For each voxel in the mask assign it a score based on the value of the corresponding voxel in the plate response image and the value in the HU image.
3. Count the number of voxels achieving above a certain score, $v_s$
4. Count the total number of voxels in the boundary mask $v_t$ The value $$\frac{v_s}{v_t}$$

will be in the range [0, 1] and can be used to measure the completeness of the fissure between a pair of lobes. Other criteria, such as the curvature of the boundary at the voxel, which can be obtained via a mesh representation of the boundary mask as detailed in step 23 of the previous section, could be incorporated into the calculation of the score in step 2, with lower curvature producing a higher score. Also, a mask representation of the voxels achieving above the score threshold could be morphologically closed with a small structuring radius or an iterative hole filling operation could be performed with a small box to fill in small holes to improve the accuracy, which is justified by the fact that incomplete sections of the fissure are usually of a larger extent than a few voxels.

Planning of Image-Guided EM Tracked Navigation to Lung Nodules

Given a system in which an EM tracked sensor location is registered to the image space of a CT scan on which the lobe segmentation above is performed, navigation to a pulmonary nodule for biopsy can be achieved via navigation through the lung airways or via the insertion of a needle into some percutaneous location on the torso.

For the first case, an airway planning path may be constructed that, starting at the trachea, traverses airway lumens to a point in the airway centerlines that is closest to the nodule, at which point an instrument housing the sensor penetrates the lumen wall to reach the nodule. It is entirely possible that this approach results in a path that crosses an interlobar boundary.

For the percutaneous case penetrating the pleura surround the lung is unavoidable, but depending on the percutaneous entry point selected it is also possible to additionally puncture a lobar boundary within the lung.

In both cases the lobe segmentation algorithm described above can indicate that the interlobar boundaries will be crossed and provide a warning or even be used as input to an automated algorithm for selecting a better airway path or percutaneous entry point. The fissure integrity analysis described above could also be isolated to just the region of the lobar boundary that would be punctured to inform the severity of the warning or quantify the need to recompute the path or entry point.

Automatic Identification of Lymph Node Regions, Identification of Suspicious Lymph Nodes and Lymph Node Planning As a byproduct of the lung and lobe segmentation algorithms combined with the airway segmentation and skeletonization described above, bronchi which supply each lobe, their descendants in the airway tree and the hilum can all be identified. This information could be used in conjunction with a lymph node map like the IASLC lymph node map to identify regions in the CT scan where lymph nodes would be expected to appear, like the Hilar, Lobar and Subsegmental lymph nodes. The ROI for these regions in the CT scan could thus be automatically identified as a byproduct of this work. The ROI could also be used as a starting point for the automatic segmentation of lymph nodes and their classification as problematic or not. The automated planning techniques described in the previous sub-section could then be applied.

Determining Change in Lobe Volume from Inspiration to Expiration

With the segmentation of the lobes for the inspiration and expiration scans as described above, the volume for each lobe in each scan can be calculated trivially as the number of voxels comprising a lobe multiplied by the volume of a voxel for the scan. This can enable many aspects of lobe based quantitative disease assessment, including general lobe function.

For example, FIG. 18 illustrates an initial segmentation 1200 of an airway tree (see step 1410 described above). The initial segmentation 1200 includes the initial treelike structure 1202 and a nodule or target 1204 (such as the target tissue 420 described above). In order to access the target 1204, the navigation system 70 can determine the pathway 1206 (e.g., an initial navigation pathway such as pathway 416 described above) through the airway tree to reach the target. After a region of interest is identified (e.g., automatically or manually based on user input such as through I/O component 78) and the disclosed processes are performed on the initial segmentation 1200, new sub-tree components 1208 are identified and connected back to the initial treelike structure 1202. Based on these new components, the navigation pathway to the target 1204 is changed, because the local extension method found airways offering a more direct or shorter pathway 1210 to the target (see FIG. 19).

In some embodiments, additional information collected during navigation can be used to enhance the segmentation methods described herein. For example, as described above with reference to steps 1100, 1300, 1400, 1500, and 1502 image data (e.g., 3D image data such as data from CT image(s)) is received, and where applicable, the image data is segmented to create an initial segmentation. During a navigated procedure, such as those described above, extension of the segmentation can be enhanced using at least one of navigation data and navigated image data. Navigation data includes data from a 3D localizer or localization element using an EM sensor (e.g., data from a device or instrument tracked by navigation system 70, as described in detail above). The navigation data includes point(s) or a point cloud, such as points corresponding to a traveled path of the navigated device or instrument, the current location of the navigated device or instrument, and/or a projected trajectory of the navigated device or instrument. Navigated image data includes 2D or 3D data from a navigated imaging device (e.g., navigated ultrasound). The navigated image data includes 2D or 3D image data (e.g., image(s), image dataset(s)). Points or a point cloud can be identified in the navigated image data. The segmentation methods disclosed herein utilize the different sources of information as parameters to determine if the point(s) or point cloud from navigation data and navigated image data should be added to the initial segmentation of the airway structure (such as by modifying the pruning constraints), as described in further detail below.

In one embodiment, the target area for use in extracting the region of interest for extension of the segmentation can be defined using the registered location of a localized medical device tracked by the navigation system 70 (e.g., steerable catheter 600 or other navigated medical device). After the initial segmentation is performed and the navigated pathway 416 or 1206 is determined, an instrument tracked by the navigation system 70 is inserted into the airway and navigated to a location in the airway. The position of the localized instrument is registered to image space and can be displayed by the navigation system 70 as described above. Based on this registered location, a region of interest can be defined to extend the initial segmentation as described with reference to FIGS. 14-19. For example, a user can manually initiate an extension of the segmentation based on the current location of the navigated instrument. Alternatively, the extension of the initial segmentation can be automatically initiated, for example based on the instrument approaching a terminal segment of the initial segmented airway, based on the instrument being positioned in a terminal segment of the initial segmented airway for a number of consecutive frames, or based on any other indication that the currently navigated region is of clinical interest. The region of interest can be centered around the navigated instrument (e.g., the tip of the navigated instrument), or can be weighted to extend toward a target area or tissue. In this embodiment, there is no dependence on a target tissue or nodule; rather, the region of interest or target area is identified based on the position of a localized instrument. In one embodiment, the segmentation extension methods can be used during a procedure to define a likelihood that an airway is in front of a navigated instrument. For example, the current trajectory of a navigated instrument can be used at the end of an initially segmented airway to define a region of interest, and the methods of FIGS. 14-19 performed to determine if it is likely that airway structure extends beyond the initial segmentation. Thus, a pathway of airway structure can be "built" in front of the navigated instrument as a procedure is performed.

The segmentation methods as shown and described offer many benefits over existing image processing methodologies and improve the operation of image processing software. The described method searches for and segments components (e.g., candidate sub-trees) that may be disconnected from the initial treelike structure in a region of interest, and connects the new segments to the previously segmented treelike structure based on geometric criteria and morphological properties of the candidate sub-tree. For example, the described method will detect potential sub-trees and infer a connection even if there is a mucus cap or motion artifact, which previous segmentation methods cannot do. Previous segmentation methods for finding airways in an image assume that no bronchi can be detected where no vessels are found. However, the disclosed method does not make this assumption, and therefore searches regions that may contain airway lumens that previous segmentation methods would fail to search. For example, finer vessels my fail to survive thresholding after down sampling or due to motion or imaging artifacts, and previous segmentation methods would fail to search these areas, for example to limit the time and memory necessary for the segmentation, and therefore fail to find airways that the current method would find. The disclosed method extends the segmentation in a region of interest, and therefore reduces the time and processing that may otherwise be required for segmentation, although the disclosed method can be applied iteratively to a coarse airway segmentation to give a more general segmentation method. As shown and described, the disclosed method region grows at detected seed points and then determines whether to discard components based on morphological and shape analysis criteria. These components are not necessarily connected to the initial segmentation, as in previous segmentation techniques that may involve pruning components already attached to region grow results. The disclosed method connects components that may or may not directly connect to the prior segmentation based on region growing alone. The method uses not only centerline orientation, but also distance and radius estimates, because the components may not connect directly to the prior segmentation. As distinct from previous techniques, the current method does no merging of masks, and only operates on a small sub-region of the image at a time, and therefore has much lesser memory requirements. The region grows are based on several seed points at once obtained through Hessian analysis of a bilaterally smoothed and contrast-enhanced sub-image, as opposed to grow regions based on one seed point alone (e.g., an estimated point in the trachea). Components are connected back to the initial segmentation that may not connect directly through region growing. The Hessian analysis utilized in the method imparts information about the orientation of the components, which information is usable in later steps of the method while also being used to discard seed points based on voxel radius estimates.

The segmentation methods described herein can be performed on image(s); image data; image dataset(s); at inspiration, expiration, or other respiratory or anatomical time period; on inspiration image data; on expiration image data; on fused inspiration-expiration image data; or any other suitable image or image data as may be useful for the particular application. For example, if a region of interest is identified during expiration, the method can be performed on the expiration image data, or alternatively can be performed on the associated inspiration image data (e.g., by deforming the region of interest back to the inspiration location, performing the method, and then deforming back to expiration for further use in navigation). The segmentation methods can be performed on image data before it is used for navigation, or on the image data during navigation. Although described herein with reference to airway structure and navigation in the airway structure, it is understood that the segmentation methods can be applied to other anatomical treelike structures within the scope of the present invention.

It is noted that the terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. Thus, a method, an apparatus, or a system that "comprises," "has," "contains," or "includes" one or more items possesses at least those one or more items, but is not limited to possessing only those one or more items. Individual elements or steps of the present methods, apparatuses, and systems are to be treated in the same manner.

The terms "a" and "an" are defined as one or more than one. The term "another" is defined as at least a second or more. The term "coupled" encompasses both direct and indirect connections, and is not limited to mechanical connections.

Those of skill in the art will appreciate that in the detailed description above, certain well known components and assembly techniques have been omitted so that the present methods, apparatuses, and systems are not obscured in unnecessary detail.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. Any feature of a disclosed embodiment can be combined with any other feature of any disclosed embodiment within the scope of the present invention.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention.

What is claimed is:

1. A method for providing an anatomical segmentation of a displayed patient anatomy for visualization by a user, comprising the following steps:

loading a 3D image of at least a region of a patient's lungs with specified reference coordinates system (RCS) coordinates into a memory component of an image analysis system;

applying histogram thresholding to the 3D image to segment air from background in the 3D image to provide a computed threshold;

thresholding voxels of a specified range into a binary mask based on the computed threshold, wherein connected components are extracted from the binary mask, resulting in a histogram threshold segmentation comprised of a plurality of components;

determining which of the plurality of components correspond to the lungs by morphologically closing and then eroding the histogram threshold segmentation to provide a closed and eroded histogram threshold segmentation comprised of lung seed voxels that are best left or best right of the connected components, wherein for each component nearest 10 to 40 voxels and their distances in RCS coordinates to a left lung seed estimate and a right lung seed estimate are computed, and the components are ranked from least to greatest by an average of the 10 to 40 voxel distances, the voxels that are above the average being the best left and best right lung seed voxels, identifying a plurality of voxels nearest individual components in the closed and eroded histogram threshold segmentation, lung seed voxels that are best left or best right of the connected components and also in the histogram threshold segmentation being used to region grow all other voxels that are 6-connected to the lung seed voxels in the histogram threshold segmentation, resulting in a binary 3D image;

extracting contours for individual successive slices of the binary 3D image in a decreasing axial direction;

computing centroids for a subset of the contours that lie a predetermined percentage of a way along a sagittal extent of the binary 3D image and that have an excepted area;

determining a trachea seed point by comparing the centroids on a predetermined number of the individual successive slices that are within a predetermined distance of one another, and having areas within a predetermined acceptable tolerance of one another, the trachea seed point being the centroid for a middle of the successive slices;

extracting, from the plurality of components, a first largest component and a second largest component by removing individual voxels in the first extracted component that are 6-connected to those of the second extracted component, the first extracted component representing a first lung and the second extracted component representing a second lung; and providing a lung vasculature segmentation comprising:
extracting voxels from within bright tubular structures of the 3D image by application of multiscale Hessian analysis of the 3D image;

assigning a metric value to each pixel based on how tubular the pixel is to provide a vesselness score for each extracted voxel;

thresholding the extracted voxels that meet a threshold vesselness score to create a vessel response image comprising a vasculature binary mask of connected components and unconnected components;

extracting the connected components from the vasculature binary mask;

discarding components that are less than 3 voxels in size;

ordering remaining voxels in each component with a maximum vessel score to establish vasculature seed voxels using the following equation:

$$sgn(H)\ln(\sqrt{|H|})*V;$$

where H is the Hounsfield density at the voxel and V is the vessel response score, wherein the ordered voxels are the vasculature seed voxels;

applying a region growing algorithm to the vessel response image using the vasculature seed voxels to create an inside binary image and a complementary outside binary image, the vasculature seed voxels having a mean vesselness response score and a mean HU value;

inserting the vasculature seed voxels into the inside binary image;

performing 6-connected region growing to the vasculature seed voxels to determine voxel inclusion into the inside binary image; and repeating the 6-connected region growing step iteratively so as to include all 6-connected neighboring voxels present in the vessel response image.

2. The method of claim 1, wherein the binary 3D image is down sampled prior to the step of extracting successive slices of the binary 3D image.

3. The method of claim 1, wherein the predetermined percentage is between about 25% and about 75% of the way along the sagittal extent of the binary 3D image.

4. The method of claim 1, wherein the excepted area is between 100 mm² and 1000 mm².

5. The method of claim 1, wherein in the step of inserting seed voxels into the inside binary image, is done according to the equation.

6. The method of claim 1, wherein in the step of performing 6-connected region growing, voxel inclusion in the inside binary image is determined by a condition:

$$w_v(|v-v_{in\_mean}|-|v-v_{out\_mean}|)+w_h(|h-h_{in\_mean}|-|h-h_{out\_mean}|)<0$$

wherein, $W_v$ and $w_n$ are 2 and 1 respectively, v is a normalized vessel response value for a candidate 6-connected voxel, h is a normalized Hounsfield value for a candidate 6-connected voxel and $V_{in\_mean}$ and $h_{in\_mean}$ are the mean vessel and Hounsfield values for the inside binary image, and $V_{out\_mean}$ and $h_{out\_mean}$ are the mean vessel and Hounsfield values for the outside binary image.

7. The method of claim 1, further comprising the steps for providing an airway segmentation mask, the steps for providing the airway segmentation mask comprising:

performing a segmentation of the lung airway using the trachea seed point to provide a coarse airway segmentation;

subtracting a distance map of the course airway segmentation from the 3D image;

performing region growing to a distance map incorporated image, and a distance map incorporated image with Gaussian smoothing applied, to provide conservative airway segmentations and aggressive airway segmentations;

and merging the coarse airway segmentation with the conservative airway segmentations and the aggressive airway segmentations.

8. The method of claim 1, further comprising the steps for providing a lung lobe segmentation mask, the steps for providing the lung lobe segmentation mask comprising:

identifying all of the voxels outside of the at least a region of the lung shown in the 3D image, the voxels outside of the at least a region of the lung shown in the 3D image being outside voxels;

assigning each of the outside voxels a marker value, the marker value being a number other than zero, to create a marker image;

estimating a segment of an airway tree belonging to each lobe, for each lung by collecting all terminal segments from the airway tree;

determining from those terminal segments in the left lung, a segment which has a distal point with the greatest axial RCS coordinate, this segment corresponds to a segment in the left superior lobe of the lung, determining from those terminal segments in the left lung a segment which has a distal point with the least axial RCS coordinate, this segment corresponds to a segment in the left inferior lobe of the lung, determining from those terminal segments in the right lung a segment which is farthest along a plane with a normal vector $$\left(0, \frac{1}{\sqrt{2}}, -\frac{1}{\sqrt{2}}\right)$$

as it passes through the 3D image, this segment corresponds to a segment in the right inferior lobe of the lung, determining from those terminal segments in the right lung a segment which has a distal point with the greatest axial RCS coordinate, this segment corresponds to a segment in the right superior lobe of the lung;
identifying a subtree for each lobe;
creating an empty mask image having geometric properties that are the same as the marker image;
identifying voxels corresponding to distal points in lobe airway segments, the voxels corresponding to distal points in lobe airway segments being lobe airway segment voxels,
assigning a mask value to each of the lobe airway segment voxels, the mask value being unique to each lung lobe segment, each lung lobe segment having anatomical characteristics that are unique;
filling voxels along rays whose geometric properties correspond to the unique anatomical characteristic of a given lung lobe segment to populate the empty mask image with filled rays of voxels;
morphologically closing and dilating the filled mask image;
copying the filled mask image into the marker image with the mask value being translated to a unique marker number for each lobe;
constructing a watershed cost image;
performing a watershed segmentation using a morphological watershed from a markers image filter.

9. The method of claim 8, wherein in the step of constructing a watershed cost image is done by:
thresholding the 3D image to create an augmented image so that voxel values in a range of interest have a fixed number added to them that is at least the lower bound in the range to ensure the values are non-negative and values outside the range are set to zero, the value of each voxel i in the watershed cost image is given by a cost equation:

$$\begin{cases} h_i + w_a \dfrac{a_i}{a_{max}} + w_v \dfrac{v_i}{v_{max}} + w_p \dfrac{p_i}{p_{max}} & i \in L \\ w_a + w_v + w_p + h_{max} + 1000 & i \notin L \end{cases}$$

where $h_i$ is the value of the voxel in the augmented image,
$a_i$ is an airway distance map value at the voxel,
$v_i$ is a vasculature distance map value at the voxel,
$P_i$ is an inverted plate distance map value at the voxel,
$a_{max}$, $v_{max}$, $p_{max}$ and $h_{max}$ are the maximum values in the airway, vasculature, inverted plate distance map and augmented image respectively,
$W_a$, $W_v$ and $W_p$ are weights that are given to influence the importance of each term, and
L is the set of voxels in the lung mask.

10. The method of claim 8, wherein in the step of filling voxels along rays, the empty mask image has an mask value and is populated with the filled rays of voxels according to the following steps:
the voxels corresponding to distal points in the lung lobe segments are set to the mask value in the mask image;
filling in rays of voxels starting with the voxels corresponding to distal points in the lung lobe segments and extending to a predetermined distance along rays parallel to an expected lobe direction.

11. The method of claim 10, wherein the predetermined distance is determined by the lung boundary.

12. A method for providing an anatomical segmentation of a displayed patient anatomy for visualization by a user, comprising the following steps:
receiving a 3D binary image that has been generated based on a non-binary 3D image of at least a region of a patient's lungs with specified reference coordinates system (RCS), wherein the non-binary 3D image is comprised of voxels and includes bright tubular structures;
extracting contours for individual successive slices of the 3D binary image in a decreasing axial direction;
computing centroids for a subset of the contours that lie a predetermined percentage of a way along a sagittal extent of the binary 3D image and that have an excepted area;
determining a trachea seed point by comparing the centroids on a predetermined number of the individual successive slices that are within a predetermined distance of one another, and having areas within a predetermined acceptable tolerance of one another, the trachea seed point being the centroid for a middle of the successive slices;
extracting a first largest component and a second largest component by removing individual voxels in the first extracted component that are 6-connected to those of the second extracted component, the first extracted component representing a first lung and the second extracted component representing a second lung;
extracting voxels from within the bright tubular structures of the non-binary 3D image by application of multi-scale Hessian analysis of the non-binary 3D image;
assigning a metric value to each voxel based on how tubular the voxel is to provide a vesselness score for each extracted voxel;
thresholding the extracted voxels that meet a threshold vesselness score to create a vessel response image comprising a vasculature binary mask of connected components and unconnected components;
extracting connected components from the vasculature binary mask;
discarding components that are less than 3 voxels in size;
ordering remaining voxels in each component with a maximum vessel score to establish vasculature seed voxels according to the following equation:

$\text{sgn}(H)\ln(\sqrt{|H|})*V;$ where H is the Hounsfield density at the voxel and V is the vessel response score, wherein the ordered voxels are the vasculature seed voxels;
applying a region growing algorithm to the vessel response image using the vasculature seed voxels to create an inside binary image and a complementary outside binary image, the vasculature seed voxels having a mean vesselness response score and a mean HU value;
inserting the vasculature seed voxels into the inside binary image;
performing 6-connected region growing to the vasculature seed voxels to determine voxel inclusion into the inside binary image; and
repeating the 6-connected region growing step iteratively so as to include all 6-connected neighboring voxels present in the vessel response image.

* * * * *

UNITED STATES PATENT AND TRADEMARK OFFICE
CERTIFICATE OF CORRECTION

PATENT NO. : 12,380,572 B2
APPLICATION NO. : 17/543472
DATED : August 5, 2025
INVENTOR(S) : Dougherty et al.

Page 1 of 1

It is certified that error appears in the above-identified patent and that said Letters Patent is hereby corrected as shown below:

In the Claims

In Column 48, Lines 5-6, in Claim 6, delete " $w_v(|v-v_{in\_mean}|-|v-v_{out\_mean}|)+w_h(|h-h_{in\_mean}|-|h-h_{out\_mean}|)<0$ " and insert -- $w_v(|v - v_{in_{mean}}| - |v - v_{out_{mean}}|) + w_h(|h - h_{in_{mean}}| - |h - h_{out_{mean}}|) <$ -- therefor In Column 48, Line 7, in Claim 6, delete "$w_n$" and insert --$W_h$-- therefor In Column 48, Line 28, in Claim 7, after "segmentations;", insert --and--

In Column 48, Line 29, in Claim 7, before "merging", delete "and"

Signed and Sealed this
Twenty-first Day of October, 2025

John A. Squires
*Director of the United States Patent and Trademark Office*